(12) United States Patent
Sasaki et al.

(10) Patent No.: US 9,893,293 B2
(45) Date of Patent: Feb. 13, 2018

(54) ORGANIC ELECTROLUMINESCENT DEVICE

(71) Applicant: SAMSUNG DISPLAY CO., LTD., Yongin-si, Gyeonggi-do (KR)

(72) Inventors: Ikuo Sasaki, Yokohama (JP); Xiulan Jin, Yokohama (JP); Masatsugu Ueno, Yokohama (JP); Koushin Matsuoka, Yokohama (JP)

(73) Assignee: SAMSUNG DISPLAY CO., LTD., Yongin-Si, Gyeonggi-Do (KR)

( * ) Notice: Subject to any disclaimer, the term of this patent is extended or adjusted under 35 U.S.C. 154(b) by 132 days.

(21) Appl. No.: 14/937,314

(22) Filed: Nov. 10, 2015

(65) Prior Publication Data

US 2016/0155943 A1 Jun. 2, 2016

(30) Foreign Application Priority Data

Dec. 2, 2014 (JP) .................................. 2014-244485
Dec. 2, 2014 (JP) .................................. 2014-244490

(51) Int. Cl.
*C09K 11/00* (2006.01)
*H01L 51/00* (2006.01)
(Continued)

(52) U.S. Cl.
CPC .......... *H01L 51/006* (2013.01); *C07C 211/43* (2013.01); *C07C 211/44* (2013.01);
(Continued)

(58) Field of Classification Search
CPC ............... H01L 51/006; H01L 51/0067; H01L 51/0072; H01L 51/0058; H01L 51/0052;
(Continued)

(56) References Cited

U.S. PATENT DOCUMENTS 9,224,969 B2   12/2015  Song et al.
9,472,767 B2   10/2016  Im et al.
(Continued)

FOREIGN PATENT DOCUMENTS

EP    2365555 A2    9/2011
JP    2002-241352 A  8/2002
(Continued)

OTHER PUBLICATIONS

European Search Report dated May 13, 2016.
(Continued)

*Primary Examiner* — Amanda C Walke
(74) *Attorney, Agent, or Firm* — Lee & Morse, P.C.

(57) ABSTRACT

An organic EL device including an anode; an emission layer; an anode-side hole transport layer between the anode and the emission layer, the anode-side hole transport layer including an anode-side hole transport material and being doped with an electron accepting material; an intermediate hole transport layer between the anode-side hole transport layer and the emission layer, the intermediate hole transport layer including an intermediate hole transport material; and an emission layer-side hole transport layer between the intermediate hole transport layer and the emission layer, the (Continued)

emission layer-side hole transport layer being adjacent to the emission layer, wherein the emission layer-side hole transport layer includes an emission layer-side hole transport material represented by the following Formula 1:

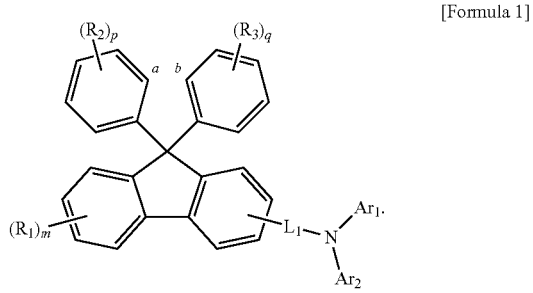

[Formula 1]

13 Claims, 1 Drawing Sheet

(51) Int. Cl.
C09K 11/02 (2006.01)
C07D 403/10 (2006.01)
C07D 401/14 (2006.01)
C07C 211/44 (2006.01)
C07C 211/61 (2006.01)
C07C 211/43 (2006.01)
C07C 211/49 (2006.01)
C09K 11/06 (2006.01)
H01L 51/50 (2006.01)

(52) U.S. Cl.
CPC .......... *C07C 211/49* (2013.01); *C07C 211/61* (2013.01); *C07D 401/14* (2013.01); *C07D 403/10* (2013.01); *C09K 11/025* (2013.01); *C09K 11/06* (2013.01); *H01L 51/0058* (2013.01); *H01L 51/0061* (2013.01); *H01L 51/0072* (2013.01); *H01L 51/5064* (2013.01); C09K 2211/1014 (2013.01); C09K 2211/1088 (2013.01); *H01L 51/0054* (2013.01); *H01L 51/0073* (2013.01); *H01L 51/0074* (2013.01); *H01L 51/506* (2013.01); *H01L 51/5012* (2013.01); *H01L 2251/308* (2013.01); *H01L 2251/552* (2013.01)

(58) Field of Classification Search
CPC ............ H01L 51/0074; H01L 51/0054; C09K 11/025; C07D 401/14; C07D 403/10; C07C 211/61; C07C 211/43; C07C 211/44; C07C 211/49
USPC .......................... 564/426, 431; 428/690, 917
See application file for complete search history.

(56) References Cited

U.S. PATENT DOCUMENTS

| | | | | |
|---|---|---|---|---|
| 2007/0082226 A1* | 4/2007 | Yu | .......................... | H01L 51/006 428/690 |
| 2007/0092753 A1* | 4/2007 | Begley | ................ | H01L 51/0052 428/690 |
| 2011/0278551 A1* | 11/2011 | Yabunouchi | .......... | C07D 405/12 257/40 |
| 2011/0278558 A1* | 11/2011 | Hamada | .............. | H01L 51/5088 257/40 |
| 2012/0302762 A1* | 11/2012 | Osaka | .................. | C07D 209/88 548/442 |
| 2014/0061630 A1* | 3/2014 | Yabunouchi | .......... | C07D 307/91 257/40 |
| 2015/0270506 A1* | 9/2015 | Voges | ................... | H01L 51/506 257/40 |
| 2016/0118597 A1* | 4/2016 | Itoi | ..................... | H01L 51/0073 257/40 |

FOREIGN PATENT DOCUMENTS

| | | |
|---|---|---|
| JP | 2011-187959 A | 9/2011 |
| JP | 2013-234169 A | 11/2013 |
| KR | 10-2011-0101418 A | 9/2011 |
| KR | 10-2013-0007159 A | 1/2013 |
| KR | 10-2013-0028813 A | 3/2013 |
| KR | 10-2013-0106255 A | 9/2013 |
| WO | WO 2007/105906 A1 | 9/2007 |
| WO | WO 2013/135352 A1 | 9/2013 |
| WO | WO 2014/034791 A1 | 3/2014 |
| WO | WO 2014/056565 A1 | 4/2014 |
| WO | WO 2014/073306 A1 | 5/2014 |

OTHER PUBLICATIONS

Padmaperuma; Substituted Molecular p-Dopants: A Theoretical Study; Advances in Materials Physics and Chemistry, 2, pp. 163-172(2012).

* cited by examiner

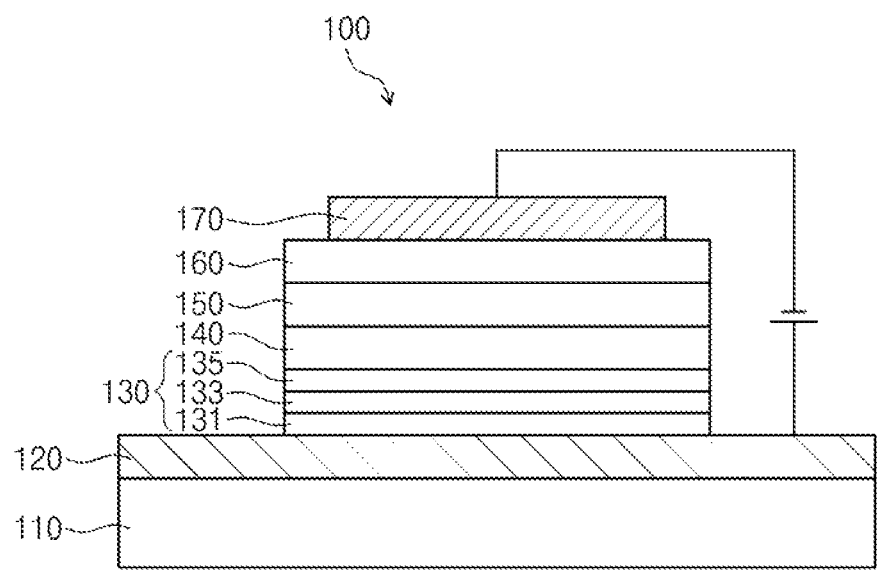

ORGANIC ELECTROLUMINESCENT DEVICE

CROSS-REFERENCE TO RELATED APPLICATIONS

Japanese Patent Application Nos. 2014-244485, filed on Dec. 2, 2014, and 2014-244490, filed on Dec. 2, 2014, in the Japanese Patent Office, and entitled: "Organic Electroluminescent Device," are incorporated by reference herein in its entirety.

BACKGROUND

1. Field

Embodiments relate to an organic electroluminescent device.

2. Description of the Related Art

Recently, development of organic electroluminescent (EL) displays is being actively conducted. Also, development of organic EL devices (which are self luminescent type emitting devices used in the organic EL displays) is being actively conducted.

The organic EL device may have a stacked structure of, e.g., an anode, a hole transport layer, an emission layer, an electron transport layer, and a cathode in order.

In such organic EL devices, holes and electrons injected from the anode and the cathode may recombine in an emission layer to generate excitons. The emission of light may be realized via the transition of the excitons generated to a ground state.

SUMMARY

Embodiments are directed to an organic electroluminescent device.

The embodiments may be realized by providing an organic EL device including an anode; an emission layer; an anode-side hole transport layer between the anode and the emission layer, the anode-side hole transport layer including an anode-side hole transport material and being doped with an electron accepting material; an intermediate hole transport layer between the anode-side hole transport layer and the emission layer, the intermediate hole transport layer including an intermediate hole transport material; and an emission layer-side hole transport layer between the intermediate hole transport layer and the emission layer, the emission layer-side hole transport layer being adjacent to the emission layer, wherein the emission layer-side hole transport layer includes an emission layer-side hole transport material represented by the following Formula 1:

[Formula 1]

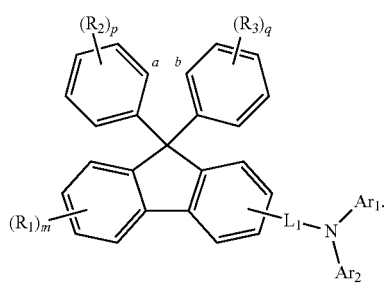

wherein, in Formula 1, $Ar_1$ and $Ar_2$ are each independently a substituted or unsubstituted aryl group having 6 to 50 ring carbon atoms or a substituted or unsubstituted heteroaryl group having 5 to 50 ring carbon atoms, $R_1$ to $R_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of $R_1$ to $R_3$ being separate or bound to form a ring, m is an integer of 0 to 4, p and q are each independently an integer of 0 to 5, $L_1$ is a direct linkage, a substituted or unsubstituted arylene group having 6 to 18 ring carbon atoms, or a substituted or unsubstituted heteroarylene group having 5 to 15 ring carbon atoms, and carbon atoms a and b are separate or are combined via a direct linkage.

The intermediate hole transport material may include a compound represented by the following Formula 2:

[Formula 2]

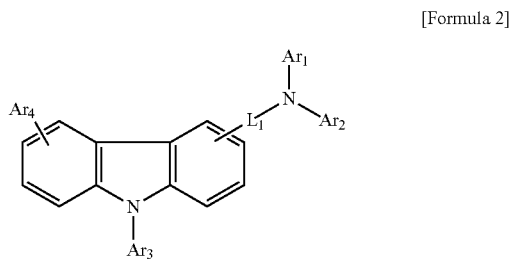

wherein, in Formula 2, $Ar_1$ to $Ar_3$ may each independently be a substituted or unsubstituted aryl group having 6 to 50 ring carbon atoms or a substituted or unsubstituted heteroaryl group having 5 to 50 ring carbon atoms, $Ar_4$ may be a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms, and $L_1$ may be a direct linkage, a substituted or unsubstituted arylene group having 6 to 18 ring carbon atoms, or a substituted or unsubstituted heteroarylene group having 5 to 15 ring carbon atoms.

The anode-side hole transport material may include the compound represented by Formula 2.

The electron accepting material may have a lowest unoccupied molecular orbital (LUMO) level of about −9.0 eV to about −4.0 eV.

The anode-side hole transport layer may be adjacent to the anode.

The emission layer may include a compound represented by the following Formula 3:

[Formula 3]

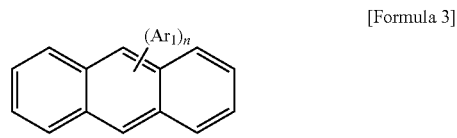

wherein, in Formula 3, each $Ar_1$ may independently be a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a substituted or unsubstituted heteroaryl group having 5 to 50 ring carbon atoms, a substituted or unsubstituted silyl group, a carboxyl group, a halogen atom, a cyano group, a nitro group, or a hydroxyl group, and n may be an integer of 1 to 10.

The embodiments may be realized by providing an organic EL device including an anode; an emission layer; an anode-side hole transport layer between the anode and the emission layer, the anode-side hole transport layer mainly including an electron accepting material; an intermediate hole transport layer between the anode-side hole transport layer and the emission layer, the intermediate hole transport layer including an intermediate hole transport material; and an emission layer-side hole transport layer between the intermediate hole transport layer and the emission layer, the emission layer-side hole transport layer being adjacent to the emission layer, wherein the emission layer-side hole transport layer includes an emission layer-side hole transport material represented by the following Formula 1:

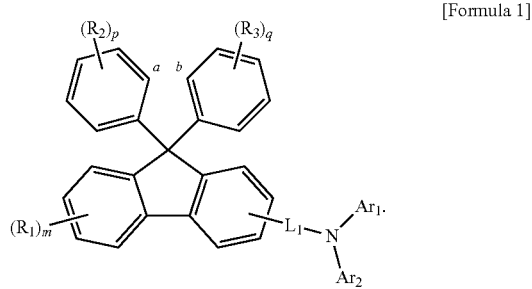

[Formula 1]

wherein, in Formula 1, $Ar_1$ and $Ar_2$ are each independently a substituted or unsubstituted aryl group having 6 to 50 ring carbon atoms or a substituted or unsubstituted heteroaryl group having 5 to 50 ring carbon atoms, $R_1$ to $R_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of $R_1$ to $R_3$ being separate or bound to form a ring, m is an integer of 0 to 4, p and q are each independently an integer of 0 to 5, $L_1$ is a direct linkage, a substituted or unsubstituted arylene group having 6 to 18 ring carbon atoms, or a substituted or unsubstituted heteroarylene group having 5 to 15 ring carbon atoms, and carbon atoms a and b are separate or are combined via a direct linkage.

The intermediate hole transport material may include a compound represented by the following Formula 2:

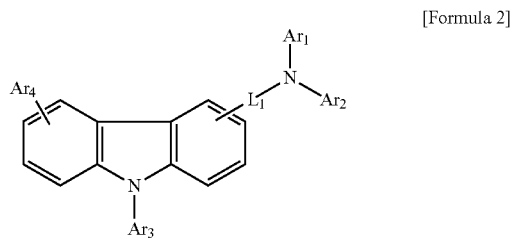

[Formula 2]

wherein, in Formula 2, $Ar_1$ to $Ar_3$ may each independently be a substituted or unsubstituted aryl group having 6 to 50 ring carbon atoms or a substituted or unsubstituted heteroaryl group having 5 to 50 ring carbon atoms, $Ar_4$ may be a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms, and $L_1$ may be a direct linkage, a substituted or unsubstituted arylene group having 6 to 18 ring carbon atoms, or a substituted or unsubstituted heteroarylene group having 5 to 15 ring carbon atoms.

The electron accepting material may have a lowest unoccupied molecular orbital (LUMO) level of about −9.0 eV to about −4.0 eV.

The anode-side hole transport layer may be adjacent to the anode.

The emission layer may include a compound represented by the following Formula 3:

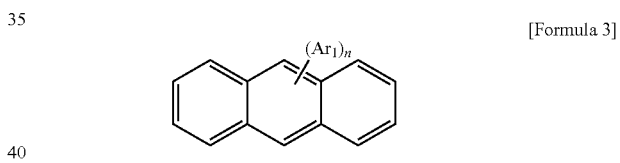

[Formula 3]

wherein, in Formula 3, each $Ar_1$ may independently be a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a substituted or unsubstituted heteroaryl group having 5 to 50 ring carbon atoms, a substituted or unsubstituted silyl group, a carboxyl group, a halogen atom, a cyano group, a nitro group, or a hydroxyl group, and n may be an integer of 1 to 10.

BRIEF DESCRIPTION OF THE DRAWING

Features will be apparent to those of ordinary skill in the art by describing in detail exemplary embodiments with reference to the attached drawing in which:

FIG. 1 illustrates a diagram of an organic EL device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. It will also be understood that when a layer or element is referred to as being "on" another layer or element, it can be directly on the other layer or element, or intervening elements may also be present. In addition, it will also be understood that when an element is referred to as being "between" two elements, it can be the only element between the two elements, or one or more intervening elements may also be present. Like reference numerals refer to like elements throughout.

<1-1. Configuration of Organic EL Device>

(1-1-1. Whole Configuration)

First, on the basis of FIG. 1, the whole configuration of an organic EL device 100 according to an embodiment will be described.

As shown in FIG. 1, an organic EL device 100 according to an embodiment may include, e.g., a substrate 110, a first electrode 120 on the substrate 110, a hole transport layer 130 on the first electrode 120, an emission layer 140 on the hole transport layer 130, an electron transport layer 150 on the emission layer 140, an electron injection layer 160 on the electron transport layer 150, and a second electrode 170 on the electron injection layer 160. In an implementation, the hole transport layer 130 may be formed to have a multi layer structure composed of a plurality of layers 131, 133 and 135.

(1-1-2. Configuration of Substrate)

The substrate 110 may be a suitable substrate used in an organic EL device. For example, the substrate 110 may be a glass substrate, a semiconductor substrate, or a transparent plastic substrate.

(1-1-3. Configuration of First Electrode)

The first electrode 120 may be, e.g., an anode, and may be formed on the substrate 110 by an evaporation method, a sputtering method, etc. For example, the first electrode 120 may be formed as a transmission type electrode using a metal, an alloy, a conductive compound, etc. having high work function. The first electrode 120 may be formed using, e.g., indium tin oxide ($In_2O_3$—$SnO_2$: ITO), indium zinc oxide ($In_2O_3$—ZnO: IZO), tin oxide ($SnO_2$), zinc oxide (ZnO), etc. having good transparency and conductivity. In an implementation, the first electrode 120 may be formed as a reflection type electrode formed by stacking magnesium (Mg), aluminum (Al), etc.

(1-1-4. Configuration of Hole Transport Layer)

The hole transport layer 130 may include a hole transport material and may have a hole transporting function. The hole transport layer 130 may be formed, e.g., on the first electrode 120 to a layer thickness (e.g., total layer thickness of a multi layer structure) of about 10 nm to about 150 nm.

The hole transport layer 130 of the organic EL device 100 according to an embodiment may be formed as a multi layer by stacking (from the first electrode 120) an anode-side hole transport layer 131, an intermediate hole transport layer 133, and an emission layer-side hole transport layer 135 one by one.

(1-1-4-1. Configuration of Anode-Side Hole Transport Layer)

The anode-side hole transport layer 131 may be a layer including an anode-side hole transport material and may be doped with an electron accepting material. For example, the anode-side hole transport layer 131 may be formed on (e.g., directly on) the first electrode 120.

The anode-side hole transport layer 131 may be doped with the electron accepting material, and hole injection property from the first electrode 120 may be improved. In an implementation, the anode-side hole transport layer 131 may be provided near the first electrode 120, e.g., may be provided adjacent to (e.g., directly adjacent to or directly contacting) the first electrode 120.

The anode-side hole transport material included in the anode-side hole transport layer 131 may include a suitable hole transport material. Examples of the anode-side hole transport material included in the anode-side hole transport layer 131 may include 1,1-bis[(di-4-tolylamino)phenyl]cyclohexane (TAPC), a carbazole derivative such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), etc.

The electron accepting material included in the anode-side hole transport layer 131 may include a suitable electron accepting material. In an implementation, the electron accepting material included in the anode-side hole transport layer 131 may have a LUMO level of about −9.0 eV to about −4.0 eV, e.g., about −6.0 eV to about −4.0 eV.

Examples of the electron accepting material having the LUMO level of about −9.0 eV to about −4.0 eV may include compounds represented by the following Formulae 4-1 to 4-14.

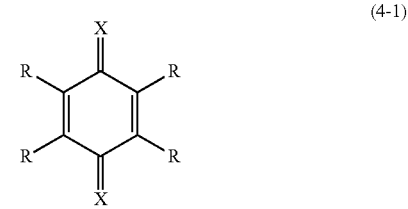

(4-1)

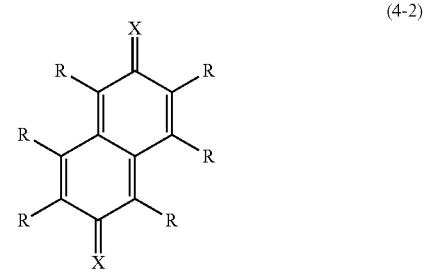

(4-2)

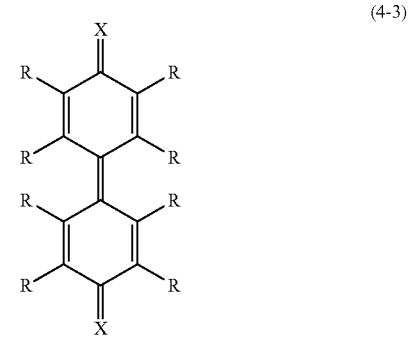

(4-3)

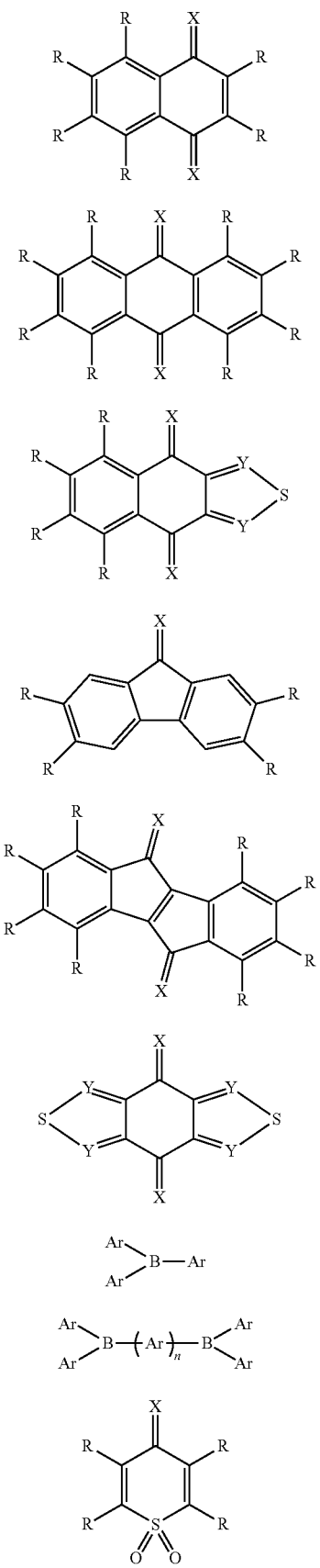

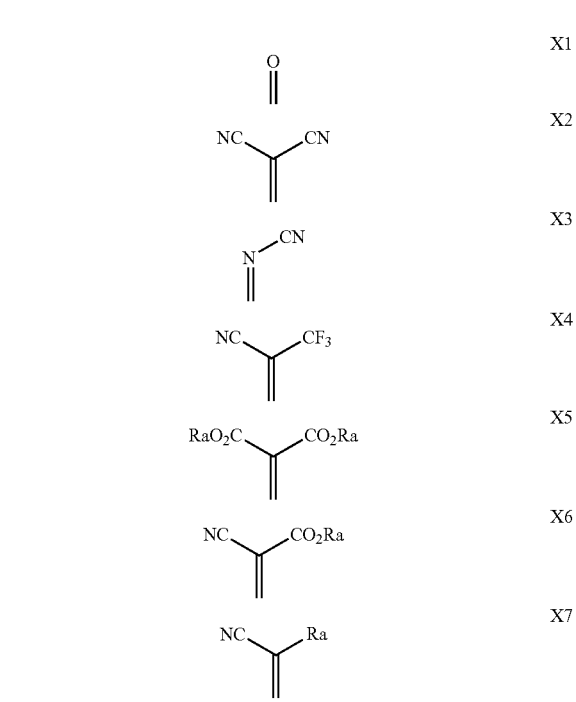

In the above Formulae 4-1 to 4-14, each R may independently be or include, e.g., a hydrogen atom, a deuterium atom, a halogen atom, a fluoroalkyl group having 1 to 50 carbon atoms, a cyano group, an alkoxy group having 1 to 50 carbon atoms, an alkyl group having 1 to 50 carbon atoms, an aryl group having 6 to 50 ring carbon atoms, or a heteroaryl group having 5 to 50 ring carbon atoms.

Each Ar may independently be or include, eg., a substituted aryl group with an electron withdrawing group or an unsubstituted aryl group having 6 to 50 ring carbon atoms or a substituted or unsubstituted heteroaryl group having 5 to 50 ring carbon atoms, each Y may independently be, e.g., a methine group (—CH=) or a nitrogen atom (—N=), each Z may independently be, e.g., a pseudohalogen atom or a sulfur (S) atom, n may be an integer of 10 and less, and each X may independently be a substituent represented by one of the following X1 to X7.

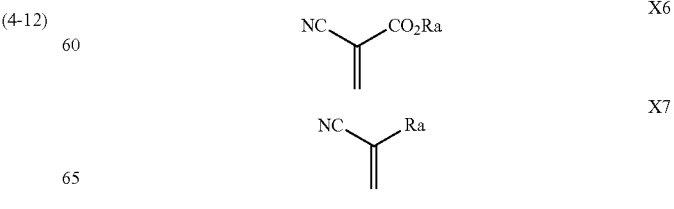

In the above Formulae X1 to X7, each Ra may independently be or include, e.g., a hydrogen atom, a deuterium atom, a halogen atom, a fluoroalkyl group having 1 to 50 carbon atoms, a cyano group, an alkoxy group having 1 to 50 carbon atoms, an alkyl group having 1 to 50 carbon atoms, a substituted or unsubstituted aryl group having 6 to 50 ring carbon atoms, or a substituted or unsubstituted heteroaryl group having 5 to 50 ring carbon atoms.

Examples of the substituted or unsubstituted aryl group having 6 to 50 ring carbon atoms represented by R, Ar, and Ra may include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, a m-terphenyl-3-yl group, an m-terphenyl-2-yl group, an o-tolyl group, a m-tolyl group, a p-tolyl group, a p-t-butyl phenyl group, a p-(2-phenylpropyl)phenyl group, a 3-methyl-2-naphthyl group, a 4-methyl-1-naphthyl group, a 4-methyl-1-anthryl group, a 4'-methyl biphenylyl group, a 4"-t-butyl-p-terphenyl-4-yl group, a fluoranthenyl group, a fluorenyl group, etc.

Examples of the substituted or unsubstituted heteroaryl group having 5 to 50 ring carbon atoms represented by R, Ar, and Ra may include a 1-pyrrolyl group, a 2-pyrrolyl group, a 3-pyrrolyl group, a pyridinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, an 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, an 1,7-phenanthroline-2-yl group, an 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, an 1-phenazinyl group, a 2-phenazinyl group, an 1-phenothiazinyl group, a 2-phenothiazinyl group, a 3-phenothiazinyl group, a 4-phenothiazinyl group, a 10-phenothiazinyl group, an 1-phenoxaziny group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, etc.

Examples of the substituted or unsubstituted fluoroalkyl group having 1 to 50 carbon atoms represented by R and Ra may include a perfluoroalkyl group such as a trifluoromethyl group, a pentafluoroethyl group, a heptafluoropropyl group and a heptadecafluorooctane group, a monofluoromethyl group, a difluoromethyl group, a trifluoroethyl group, a tetrafluoropropyl group, an octafluoropentyl group, etc.

Examples of the substituted or unsubstituted alkyl group having 1 to 50 carbon atoms represented by R and Ra may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, an 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, an aminomethyl group, an 1-aminoethyl group, a 2-aminoethyl group, a 2-aminoisobutyl group, an 1,2-diaminoethyl group, an 1,3-diaminoisopropyl group, a 2,3-diamino-t-butyl group, an 1,2,3-triaminopropyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyanopropyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, a cyclopropyl group, a cyclobutyl group, a cyclopentyl group, a cyclohexyl group, a 4-methylcyclohexyl group, an 1-adamantyl group, a 2-adamantyl group, an 1-norbornyl group, a 2-norbornyl group, etc.

The substituted or unsubstituted alkoxy group having 1 to 50 carbon atoms represented by R and Ra may be a group represented by —OY. Examples of Y may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, an 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, an aminomethyl group, an 1-aminoethyl group, a 2-aminoethyl group, a 2-aminoisobutyl group, an 1,2-diaminoethyl group, an 1,3-diaminoisopropyl group, a 2,3-diamino-t-butyl group, an 1,2,3-triaminopropyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyanopropyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, etc.

Examples of the halogen atom represented by R and Ra may include fluorine (F), chlorine (Cl), bromine (Br), iodine (I), etc.

In an implementation, the electron accepting material may include one of the following Compounds 4-15 and 4-16. For example, the LUMO level of Compound 4-15 may be about −4.40 eV, and the LUMO level of Compound 4-16 may be about −5.20 eV.

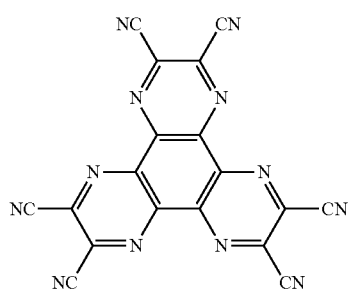

(4-15)

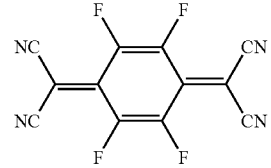

(4-16)

In an implementation, a doping amount of the electron accepting material may be a suitable capable of being doped into the anode-side hole transport layer 131. For example, the doping amount of the electron accepting material may be about 0.1 wt % to about 50 wt %, on the basis of the total amount or weight of the anode-side hole transport material included in the anode-side hole transport layer 131. In an implementation, the doping amount may be about 0.5 wt % to about 5 wt %.

(1-1-4-2. Configuration of Intermediate Hole Transport Layer)

The intermediate hole transport layer 133 may include an intermediate hole transport material. The intermediate hole transport layer 133 may be formed, e.g., on the anode-side hole transport layer 131.

The intermediate hole transport material included in the intermediate hole transport layer 133 may include a suitable hole transport material. For example, the intermediate hole transport material may include the above-mentioned hole transport materials as the anode-side hole transport materials.

In an implementation, the intermediate hole transport material may include a compound represented by the following Formula 2.

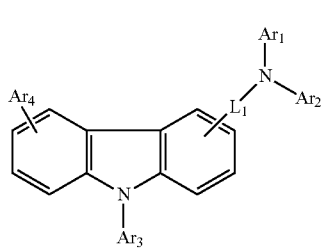

[Formula 2]

In the above Formula 2, $Ar_1$ to $Ar_3$ may each independently be or include, e.g., a substituted or unsubstituted aryl group having 6 to 50 ring carbon atoms or a substituted or unsubstituted heteroaryl group having 5 to 50 ring carbon atoms. $Ar_4$ may be or include, e.g., a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms. $L_1$ may be or may include, e.g., a direct linkage (single bond), a substituted or unsubstituted arylene group having 6 to 18 ring carbon atoms, or a substituted or unsubstituted heteroarylene group having 5 to 15 ring carbon atoms.

Examples of $Ar_1$ to $Ar_3$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzothiazolyl group, a quinoxalyl group, a benzoxazolyl group, a pyrazolyl group, a dibenzofuranyl group, a dibenzothienyl group, etc. In an implementation, $Ar_1$ to $Ar_3$ may include the phenyl group, the biphenyl group, the terphenyl group, the fluorenyl group, the carbazolyl group, the dibenzofuranyl group, etc.

Examples of $Ar_4$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In an implementation, $Ar_4$ may include the phenyl group, the biphenyl group, the terphenyl group, the fluorenyl group, the carbazolyl group, the dibenzofuranyl group, the methyl group, the ethyl group, etc.

Examples of $L_1$ (other than the direct linkage) may include a phenylene group, a biphenylene group, a terphenylene group, a naphthylene group, an anthrylene group, a phenanthrylene group, a fluorenylene group, an indenylene group, a pyrenylene group, an acetonaphthenylene group, a fluoranthenylene group, a triphenylenylene group, a pyridylene group, a furanylene group, a pyranylene group, a thienylene group, a quinolylene group, an isoquinolylene group, a benzofuranylene group, a benzothienylene group, an indolylene group, a carbazolylene group, a benzoxazolylene group, a benzothiazolylene group, a kinokisariren group, a benzoimidazolylene group, a pyrazolylene group, a dibenzofuranylene group, a dibenzothienylene group, etc. In an implementation, $L_1$ may include the direct linkage, the phenylene group, the biphenylene group, the terphenylene group, the fluorenylene group, the carbazolylene group, or the dibenzofuranylene group.

Examples of the compound represented by Formula 2 may include the following Compounds 2-1 to 2-16.

(2-1)

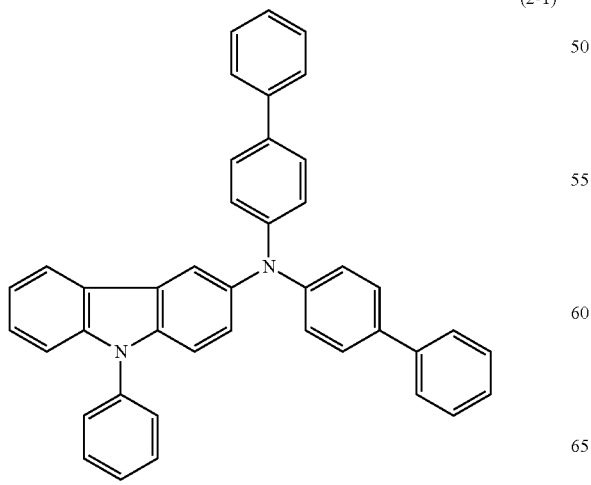

(2-2)

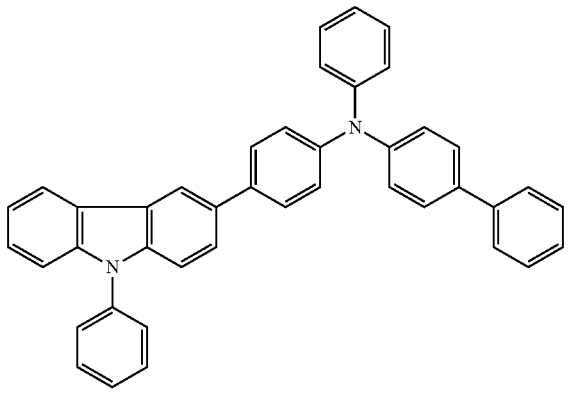

(2-3)

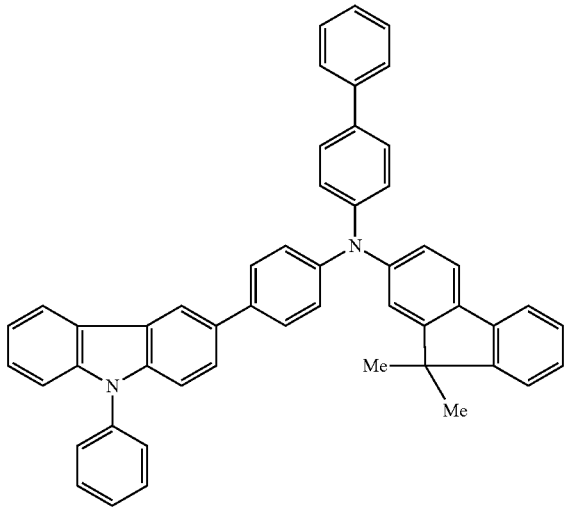

(2-4)

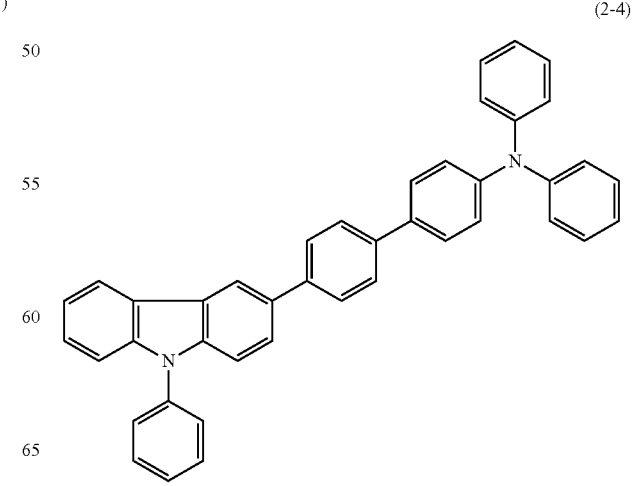

(2-5)
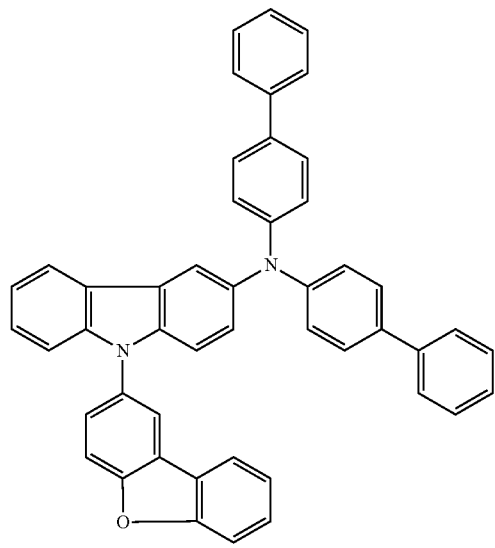
(2-6)
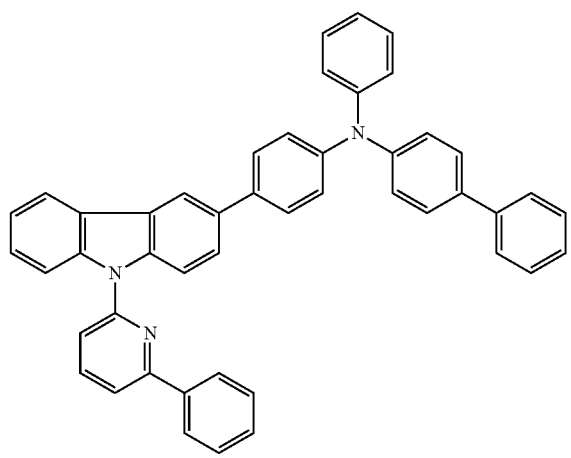
(2-7)
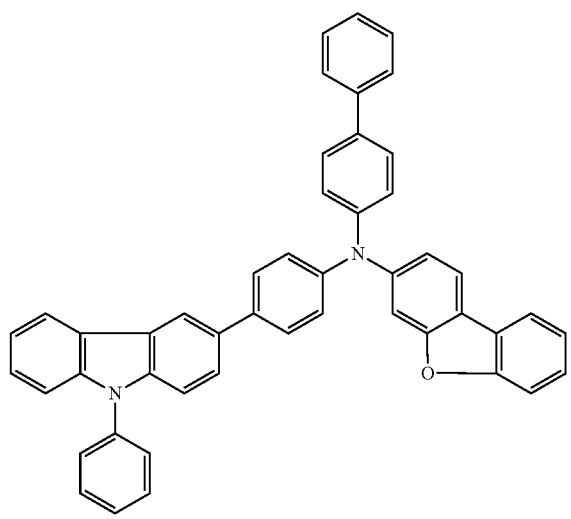
(2-8)
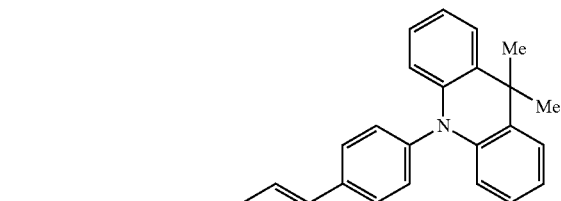
(2-9)
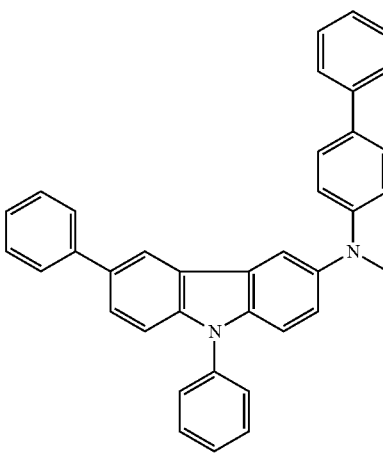
(2-10)
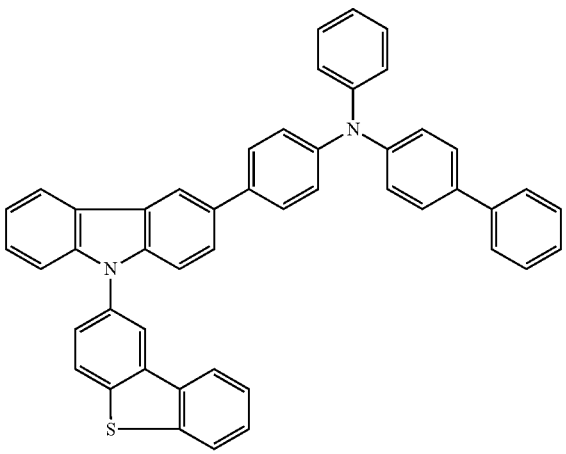

-continued (2-11)
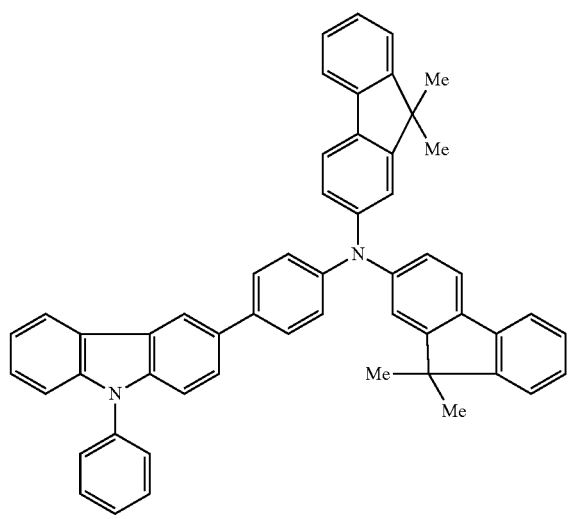

(2-12)
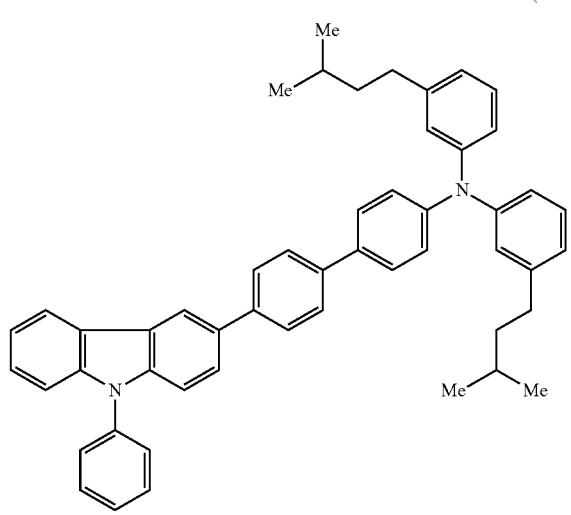

(2-13)
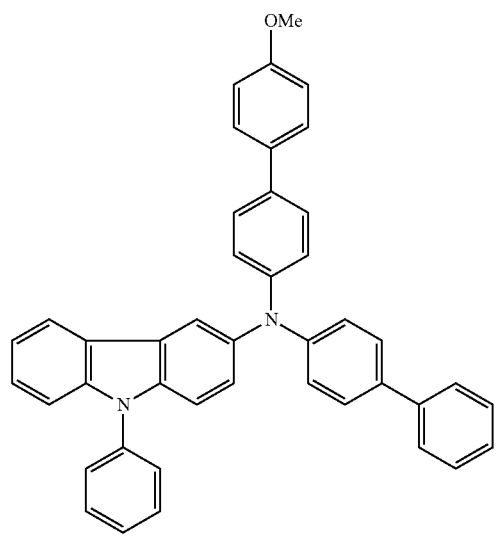

-continued (2-14)
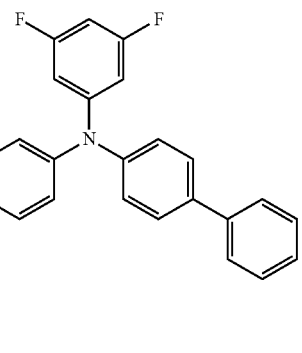

(2-15)
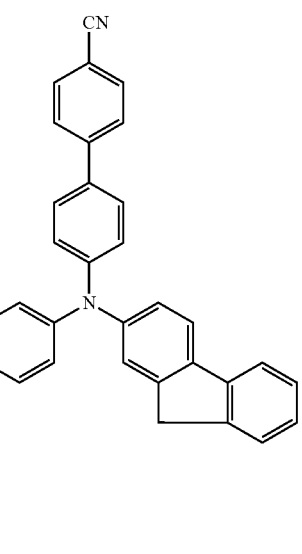

(2-16)
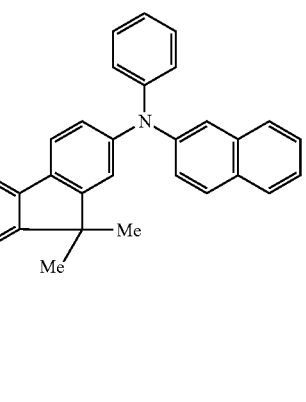

The intermediate hole transport layer 133 may include the compound represented by the above Formula 2 as the intermediate hole transport material and may help improve the hole transporting property of the hole transport layer 130. Thus, the emission efficiency of the organic EL device 100 may be improved.

In an implementation, the compound represented by Formula 2 may be included in the anode-side hole transport layer 131 as the anode-side hole transport material. In the case that the anode-side hole transport layer 131 includes the compound represented by Formula 2 as the anode-side hole transport material, the hole transporting property of the hole transport layer 130 may be improved, and the emission efficiency of the organic EL device 100 may be improved.

In an implementation, in the case that the ratio included of a carbazole derivative (such as the compound represented by Formula 2) is high in the hole transport layer 130, the emission life of the organic EL device 100 may be improved.

The anode-side hole transport layer 131 may further include other hole transport materials as the anode-side hole transport materials in addition to the compound represented by Formula 2.

(1-1-4-3. Configuration of Emission Layer-side Hole Transport Layer)

The emission layer-side hole transport layer 135 may include a compound represented by the following Formula 1. The emission layer-side hole transport layer 135 may be formed, e.g., on the intermediate hole transport layer 133, adjacent to (e.g., directly adjacent to or directly contacting) the emission layer 140.

[Formula 1]

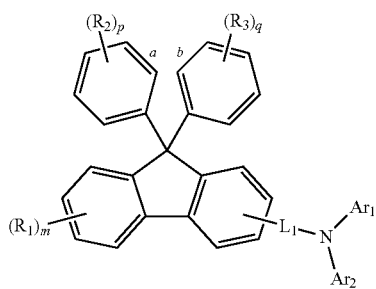

In Formula 1, $Ar_1$ and $Ar_2$ may each independently be or include, e.g., a substituted or unsubstituted aryl group having 6 to 50 ring carbon atoms or a substituted or unsubstituted heteroaryl group having 5 to 50 ring carbon atoms.

$R_1$ to $R_3$ may each independently be or include, e.g., a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms. In an implementation, adjacent ones of $R_1$ to $R_3$ may be separate from one another or may be bound to form a ring.

In addition, m may be an integer of 0 to 4, and p and q may each independently be an integer of 0 to 5. $L_1$ may be or may include, e.g., a direct linkage (e.g., single bond), a substituted or unsubstituted arylene group having 6 to 18 ring carbon atoms, or a substituted or unsubstituted heteroarylene group having 5 to 15 ring carbon atoms. Carbon atoms a and b may be separate from one another or may be bound or combined via a direct linkage.

Examples of $Ar_1$ and $Ar_2$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In an implementation, $Ar_1$ and $Ar_2$ may include the phenyl group, the biphenyl group, the terphenyl group, the fluorenyl group, the carbazolyl group and the dibenzofuranyl group.

Examples of $R_1$ to $R_3$ may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc., other than the particular examples of $Ar_1$ and $Ar_2$.

Substituents of $Ar_1$ and $Ar_2$ and $R_1$ to $R_3$ may include an alkyl group, an alkoxy group, an aryl group and a heteroaryl group. Examples of the aryl group and the heteroaryl group may be the same as described above. Examples of the alkyl group, the aryl group and the heteroaryl group may be the same as described above. Examples of the alkoxy group may include an alkoxy group substituted with the alkyl group.

Examples of $L_1$ (other than the direct linkage/single bond) may include a divalent substituent or version of groups described with respect to $Ar_1$ and $Ar_2$. For example, $L_1$ may include a phenylene group, a biphenylene group, a terphenylene group, a naphthylene group, an anthrylene group, a phenanthrylene group, a fluorirane group, an indanediyl group, a pyrenediyl group, an acenaphthenediyl group, a fluoranthenediyl group, a triphenylenediyl group, a pyridinediyl group, a pyranediyl group, a quinolinediyl group, an isoquinolinediyl group, a benzofurandiyl group, a benzothiophenediyl group, an indolediyl group, a carbazolediyl group, a benzoxazolediyl group, a benzothiazolediyl group, a quinoxalinediyl group, a benzoimidazolediyl group, and a dibenzofurandiyl group. In an implementation, the phenylene group, the terphenylene group, the fluoriranediyl group, the carbazolediyl group and the dibenzofurandiyl group may be used.

In an implementation, the compound represented by Formula 1 may include one of the following Compounds 1 to 12.

1

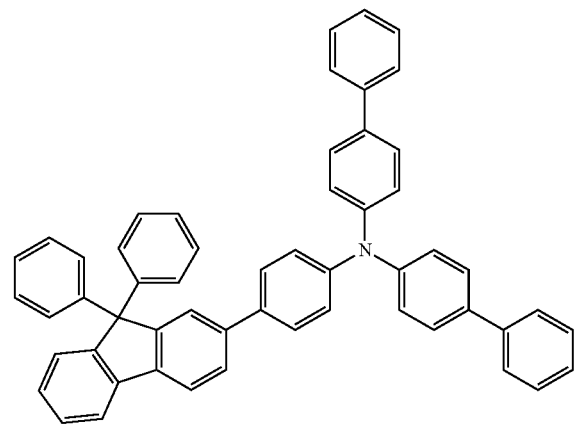

2
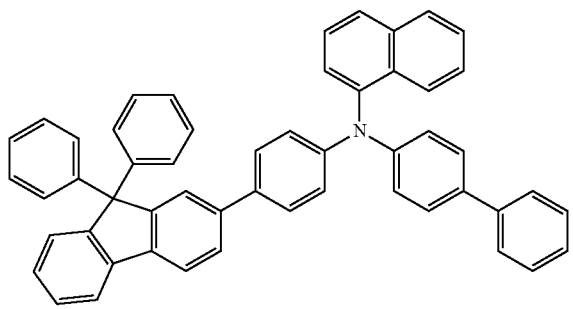
3
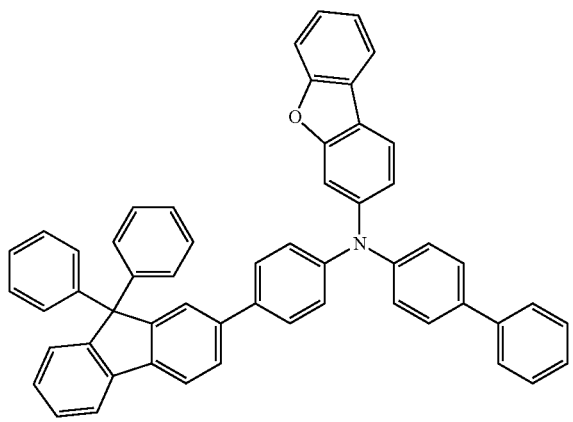
4
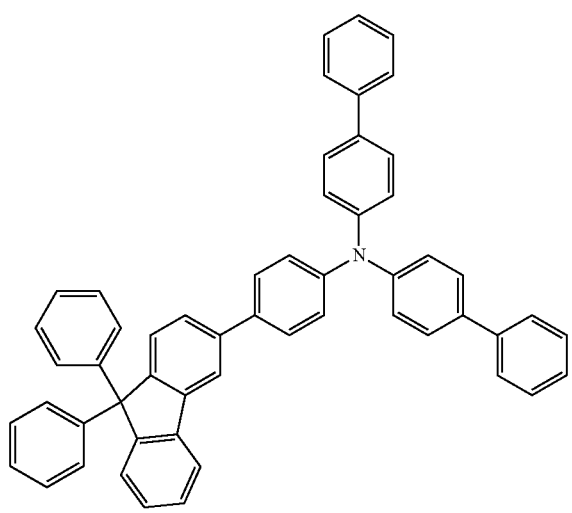
5
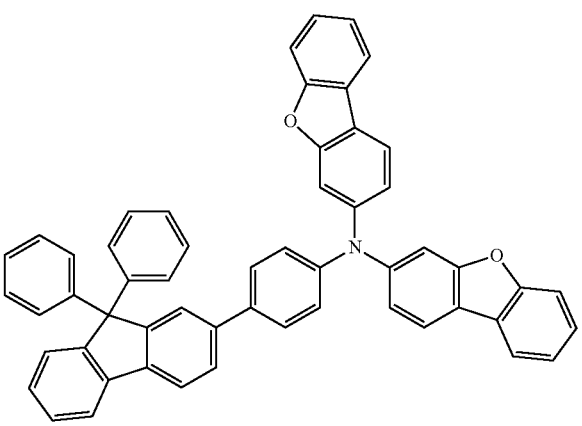
6
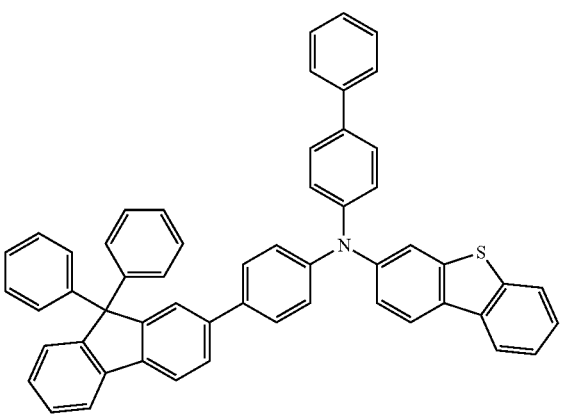
7
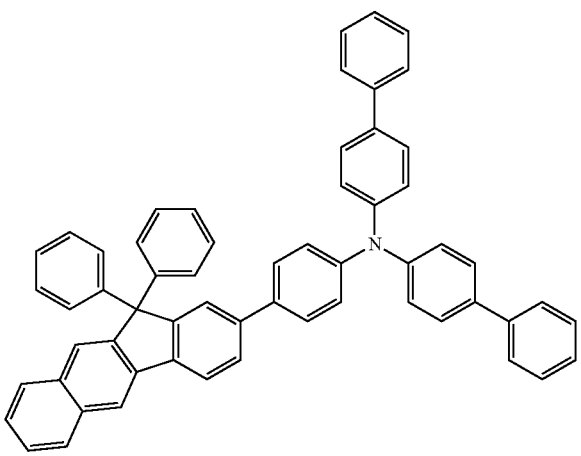

8

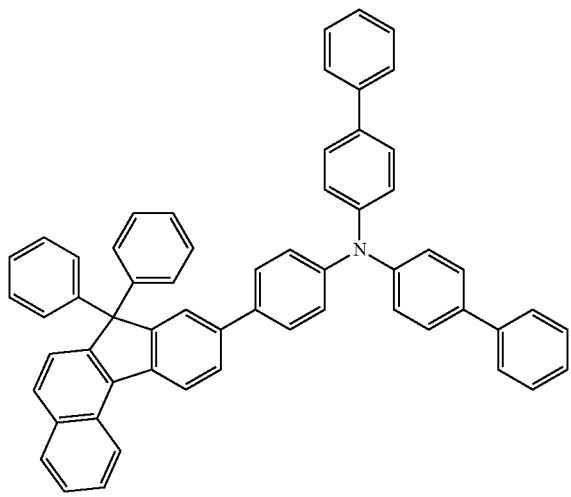

9

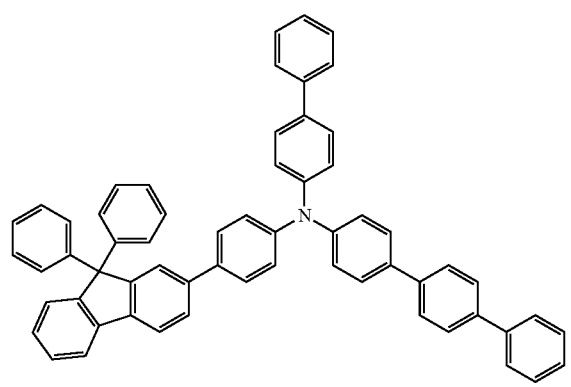

10

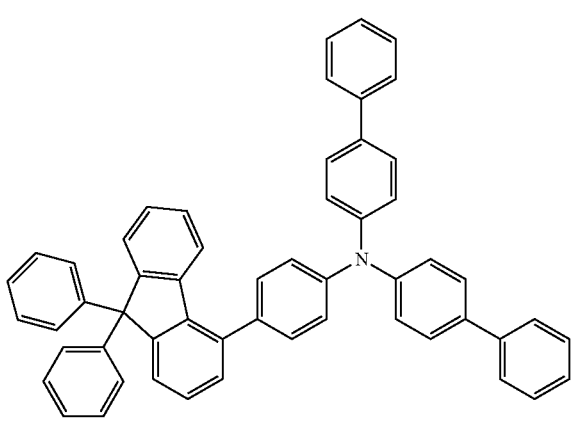

11

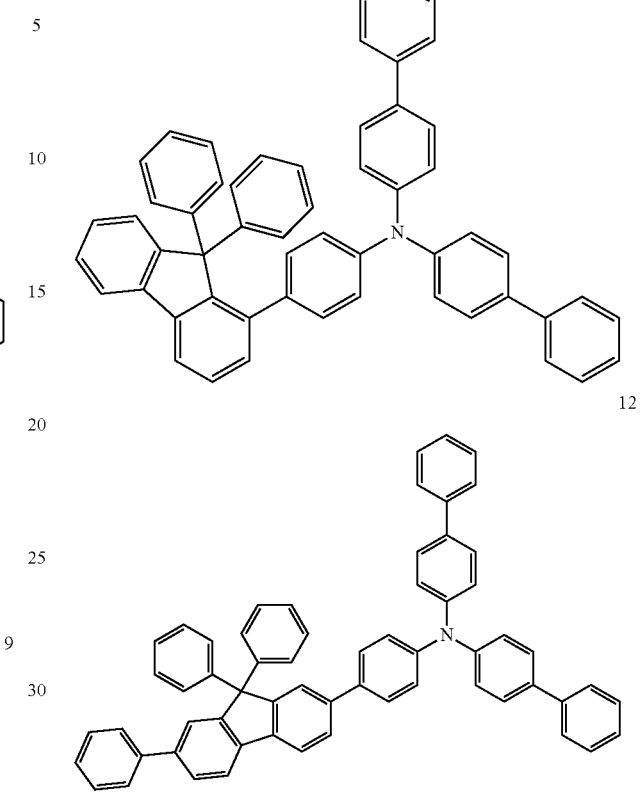

The emission layer-side hole transport layer 135 may include the compound represented by the above Formula 1 as the emission layer-side hole transport material, and may passivate the hole transport layer 130 from electrons not consumed in the emission layer 140. In an implementation, the emission layer-side hole transport layer 135 may include the compound represented by the above Formula 1, and the diffusion of energy in an excited state generated in the emission layer 140 into the hole transport layer 130 may be reduced and/or prevented. Thus, according to this configuration, the emission layer-side hole transport layer 135 may help improve the current flow durability of the hole transport layer 130.

The emission layer-side hole transport layer 135 may be formed near the emission layer 140. For example, the emission layer-side hole transport layer 135 may be formed adjacent to (e.g., directly adjacent to or directly contacting) the emission layer 140 to effectively help prevent the diffusion of the electrons or the energy from the emission layer 140.

The emission layer-side hole transport layer 135 may include the compound represented by the above Formula 1, the charge balance of the whole organic EL device 100 may be controlled, and the diffusion of the electron accepting material doped into the anode-side hole transport layer 131 into the emission layer 140 may be restrained. Accordingly, the emission layer-side hole transport layer 135 may help improve the whole charge transport property of the hole transport layer 130.

In an implementation, the emission layer-side hole transport layer 135 may include the compound represented by the above Formula 1, and the charge transport property and current flow durability of the hole transport layer 130 may be improved. Thus, the emission efficiency and emission life of the organic EL device 100 may be improved.

As described above, the hole transport layer 130 including the anode-side hole transport layer 131, the intermediate hole transport layer 133, and the emission layer-side hole transport layer 135 may help improve the current flow durability and hole transport property of the organic EL device 100. Thus, the organic EL device 100 according to an embodiment may have improved emission efficiency and emission life.

(1-1-5. Configuration of Emission Layer)

The emission layer 140 may include a host material, a dopant material as a luminescent material, etc. and emits light via fluorescence or phosphorescence. The emission layer 140 may be formed, e.g., on the hole transport layer 130 to a layer thickness within a range from about 10 nm to about 60 nm.

The host material and the dopant material included in the emission layer 140 may include suitable host materials and dopant materials. For example, the emission layer 140 may include a fluoranthene derivative, pyrene (and the derivative thereof), an arylacetylene derivative, a fluorene derivative, perylene (and the derivative thereof), a chrysene derivative, a styryl derivative, etc. as the host material or the dopant material. More particularly, the emission layer 140 may include tris(8-quinolinolato)aluminum (Alq3), 4,4'-N,N'-dicarbazole-biphenyl (CBP), poly(n-vinylcarbazole) (PVK), 4,4',4''-tris(N-carbazolyl)triphenylamine (TCTA), 1,3,5-tris(N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dm-CBP), bis(2,2-diphenyl vinyl)-1,1'-biphenyl (DPVBi), 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-(E)-2-(6-((E)-4-(diphenylamino)styryl)naphthalen-2-yl)vinyl)phenyl)-N-phenylbenzenamine (N-BDAVBi), 2,5,8,11-tetra-t-butylperylene (TBPe), 1,1-dipyrene, 1,4-dipyrenylbenzene, 1,4-bis(N,N-diphenylamino)pyrene, etc. as the host material or the dopant material.

In an implementation, the emission layer 140 may include a compound represented by the following Formula 3.

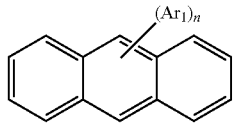

[Formula 3]

In the above Formula 3, each $Ar_1$ may independently be or include, e.g., a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a substituted or unsubstituted heteroaryl group having 5 to 50 ring carbon atoms, a substituted or unsubstituted silyl group, a carboxyl group, a halogen atom, a cyano group, a nitro group or a hydroxyl group, and n may be an integer of 1 to 10.

In an implementation, the compound represented by Formula 3 may include one of the following Compounds 3-1 to 3-12.

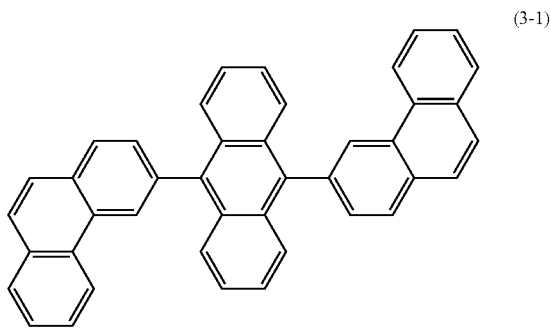

(3-1)

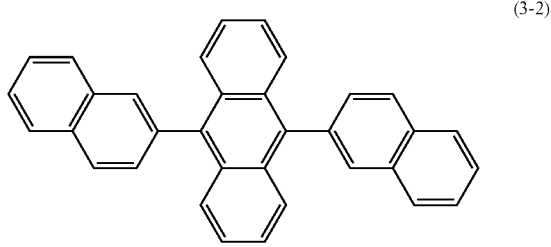

(3-2)

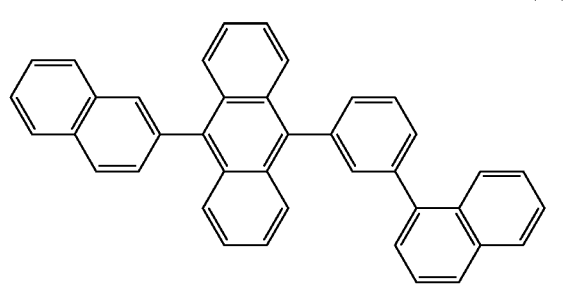

(3-3)

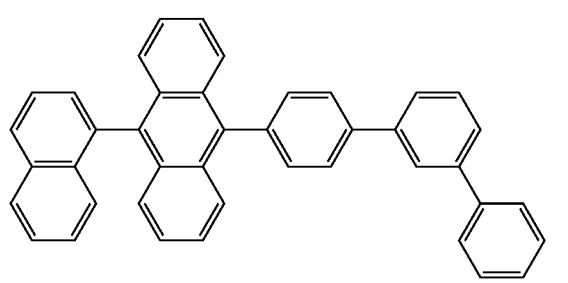

(3-4)

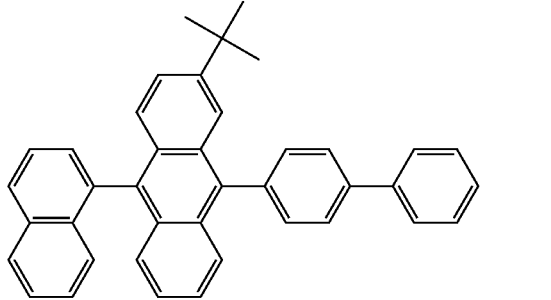

(3-5)

-continued (3-6) 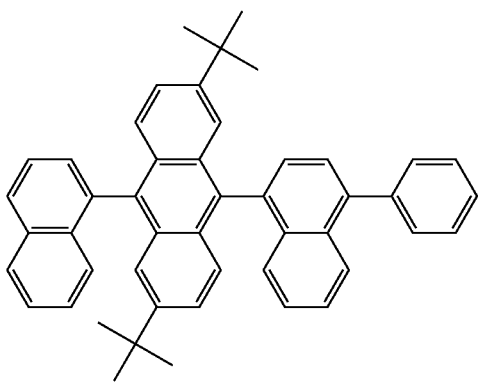

(3-7) 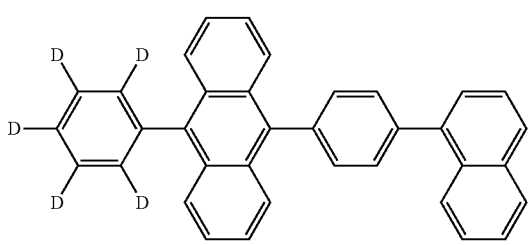

(3-8) 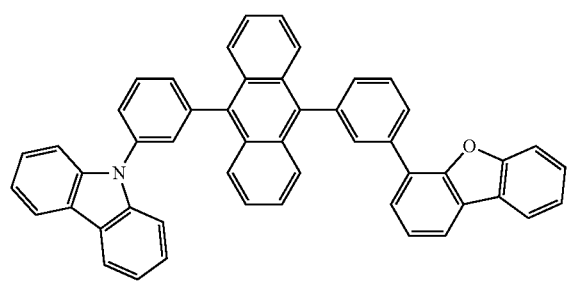

(3-9) 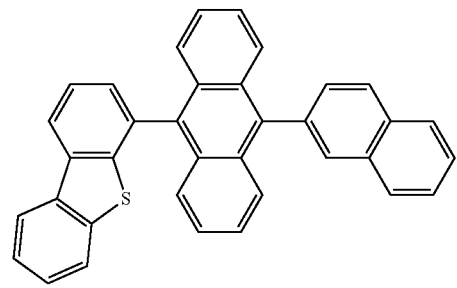

(3-10) 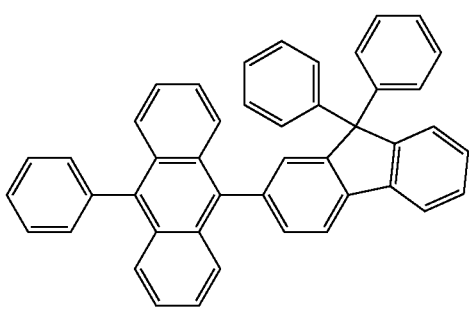

-continued (3-11) 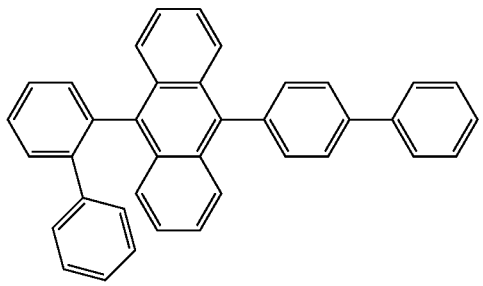

(3-12) 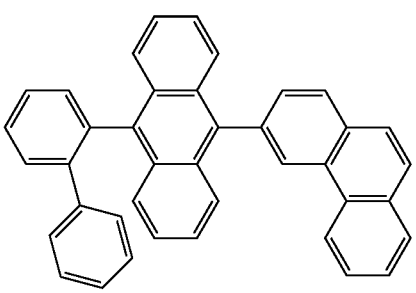

In the case that the emission layer 140 includes the compound represented by Formula 3, the anode-side hole transport layer 131 may help significantly improve the hole injection property from the first electrode 120. Thus, the emission layer 140 may help further improve the emission efficiency and emission life of the organic EL device 100 by including the compound represented by Formula 3.

The emission layer 140 may include the compound represented by Formula 3 as the host material or as the dopant material.

The emission layer 140 may be formed as a layer emitting light with specific color. For example, the emission layer 140 may be formed as a red emitting layer, a green emitting layer, or a blue emitting layer.

In the case that the emission layer 140 is the blue emitting layer, suitable blue dopants may be used. For example, perylene and the derivative thereof, an iridium (Ir) complex such as bis[2-(4,6-difluorophenyl)pyridinate]picolinate iridium(III) (FIrpic) may be used as the blue dopant.

In the case that the emission layer 140 is the red emitting layer, suitable red dopants may be used. For example, rubrene and the derivative thereof, 4-dicyanomethylene-2-(p-dimethylaminostyryl)-6-methyl-4H-pyrane (DCM) and the derivative thereof, an iridium complex such as bis(1-phenylisoquinoline) (acetylacetonate) iridium(III) (Ir(piq)$_2$(acac), an osmium (Os) complex, a platinum complex, etc. may be used as the red dopant.

In the case that the emission layer 140 is the green emitting layer, suitable green dopants may be used. For example, coumarin and the derivative thereof, an iridium complex such as tris(2-phenylpyridine) iridium(III) (Ir(ppy)$_3$), etc. may be used.

(1-1-6. Configuration of Electron Transport Layer)

The electron transport layer 150 is a layer including an electron transport material and having electron transporting function. The electron transport layer 150 may be formed, e.g., on the emission layer 140 to a layer thickness within a range from about 15 nm to about 50 nm. The electron transport material included in the electron transport layer 150 may include suitable electron transport materials. Examples of the electron transport material may include a quinoline derivative such as tris(8-quinolinato)aluminum (Alq3), a 1,2,4-triazole derivative (TAZ), bis(2-methyl-8-quinolinolato)-(p-phenylphenolate)-aluminum (BAlq), berylliumbis(benzoquinolin-10-olate) (BeBq2), a Li complex such as lithium quinolate (LiQ), a nitrogen-containing aromatic ring, etc. Examples of the nitrogen-containing aromatic ring may include a material including a pyridine ring such as 1,3,5-tri[(3-pyridyl)-phen-3-yl]benzene, a material including a triazine ring such as 2,4,6-tris(3'-(pyridin-3-yl)biphenyl-3-yl)-1,3,5-triazine, a material including an imidazole derivative such as 2-(4-(N-phenylbenzoimidazolyl-1-ylphenyl)-9,10-dinaphthylanthracene), etc.

(1-1-7. Configuration of Electron Injection Layer)

The electron injection layer 160 is a layer having function of facilitating injection of electrons from the second electrode 170. The electron injection layer 160 may be formed, e.g., on the electron transport layer 150 to a layer thickness within a range from about 0.3 nm to about 9 nm. The electron injection layer 160 may be formed using suitable materials that may be used as materials for forming the electron injection layer 160. Examples of the material for forming the electron injection layer 160 may include lithium fluoride (LiF), sodium chloride (NaCl), cesium fluoride (CsF), lithium oxide (Li$_2$O), barium oxide (BaO), lithium quinolate (LiQ), etc.

(1-1-8. Configuration of Second Electrode)

The second electrode 170 may be, e.g., a cathode, and may formed on the electron injection layer 160 using an evaporation method or a sputtering method. For example, the second electrode 170 may be formed as a reflection type electrode using a metal, an alloy, a conductive compound, etc. having low work function. The second electrode 170 may be formed using, e.g., lithium (Li), magnesium (Mg), aluminum (Al), silver (Ag), aluminum-lithium (Al—Li), calcium (Ca), magnesium-indium (Mg—In) and magnesium-silver (Mg—Ag). The second electrode 170 may be formed as a thin film of the material, having a thickness of about 20 nm and less and may be formed as a transmission type electrode using ITO, IZO, etc.

(1-1-9. Modification Example of Organic EL Device)

The structure of the organic EL device 100 shown in FIG. 1 is only an illustration. In the organic EL device 100 according to an embodiment, some layers may be formed as a multi layer, or another layer may be additionally formed. In the organic EL device 100 according to an embodiment, at least one of the electron transport layer 150 and the electron injection layer 160 may not be provided.

In an implementation, in the organic EL device 100 according to an embodiment, a hole injection layer may be provided between the first electrode 120 and the hole transport layer 130.

The hole injection layer is a layer having function of facilitating injection of holes from the first electrode 120. The hole injection layer may be formed, e.g., on the first electrode 120 to a layer thickness within a range from about 10 nm to about 150 nm. The hole injection layer may be formed using suitable materials that are materials for forming the hole injection layer. Example of the material for forming the hole injection layer may include a triphenylamine-containing polyether ketone (TPAPEK), 4-isopropyl-4'-methyldiphenyliodonium tetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylamino)triphenylamine (m-MTDATA), N,N'-di(1-naphthyl)-N,N'-diphenylbenzidine (NPB), 4,4',4''-tris{N,N-diamino}triphenylamine (TDATA), 4,4',4''-tris(N,N-2-naphthylphenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA) or polyaniline/poly(4-styrenesulfonate) (PANI/PSS), etc.

(1-1-10. Method of Manufacturing Organic EL Device)

Each layer of the organic EL device 100 according to an embodiment as described above may be formed by selecting an appropriate layer forming method depending on materials used such as vacuum evaporation, sputtering, and various coating methods.

For example, a metal layer (such as the first electrode 120, the second electrode 170, and the electron injection layer 160) may be formed using an evaporation method including an electron beam evaporation method, a hot filament evaporation method and a vacuum evaporation method, a sputtering method, and a plating method such as an electroplating method and an electroless plating method.

An organic layer (such as the hole transport layer 130, the emission layer 140 and the electron transport layer 150) may be formed using a physical vapor deposition (PVD) method such as a vacuum deposition method, a printing method such as a screen printing method and an ink jet printing method, a laser transcription method and a coat method such as a spin coat method.

Hereinabove, an embodiment of the organic EL device 100 according to an embodiment has been explained in detail.

EXAMPLES

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

<1-2. Examples>

Hereinafter, organic EL devices according to exemplary embodiments will be explained in particular referring to examples and comparative examples.

(1-2-1. Synthesis of Compounds)

Synthetic Example 1

Synthesis of Compound 1

Compound 1 was synthesized according to the following reaction scheme.

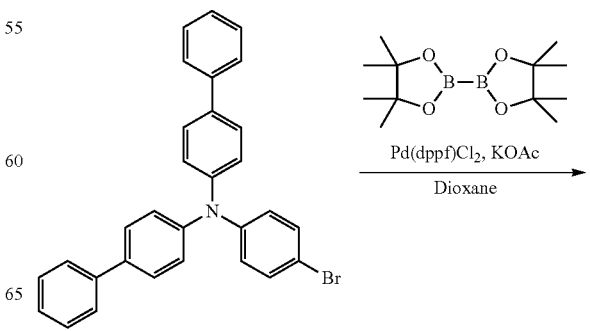

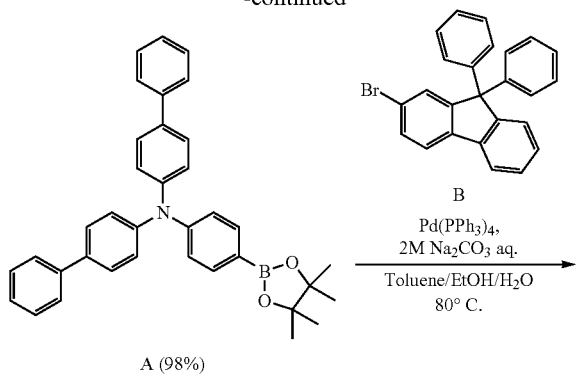

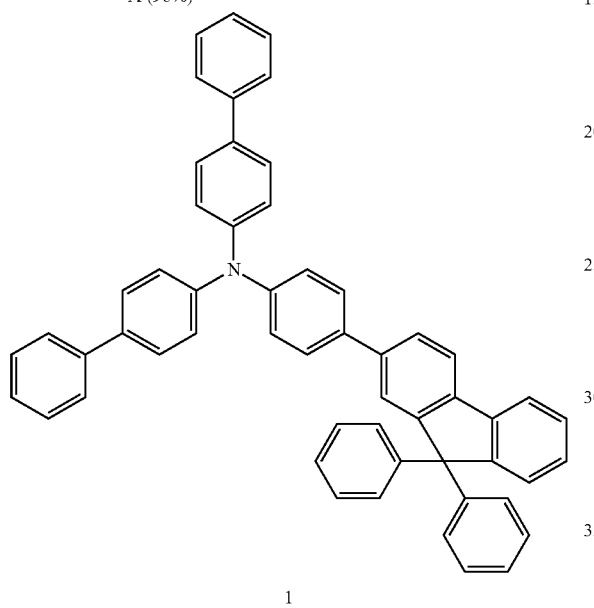

Synthesis of Compound A

Under an Ar atmosphere, 53.8 g of N-[1,1'-biphenyl]-4-yl-N-(4-bromophenyl)-[1,1'-biphenyl]-4-amine, 6.46 g of [1,1'-bis(diphenylphosphino) ferrocene] dichloropalladium·$CH_2Cl_2$ (Pd(dppf)$Cl_2$·$CH_2Cl_2$), 33.3 g of potassium acetate (KOAc) and 33.0 g of bis(pinacolato) diboron were added to a 2 L flask, followed by degassing under vacuum and stirring in 750 mL of a dioxane solvent at about 100° C. for about 12 hours. Then, solvents were distilled, $CH_2Cl_2$ and water were added thereto, an organic phase was separated, magnesium sulfate and activated clay were added thereto, filtering with suction was performed, and the solvents were distilled. The crude product thus obtained was separated by silica gel column chromatography (using a mixed solvent of dichloromethane and hexane) to produce 56.8 g (Yield 98%) of Compound A as a white solid (FAB-MS: $C_{36}H_{34}BNO_2$, measured value 523).

Synthesis of Compound 1

Under an Ar atmosphere, 1.66 g of Compound A, 1.52 g of Compound B, 0.11 g of tetrakis(triphenylphosphine) palladium(0) (Pd(PPh$_3$)$_4$), and 1.1 g of sodium carbonate were added to a 200 mL, three necked flask, followed by heating and stirring in a mixed solvent of 40 mL of toluene, 19 mL of EtOH and 9.0 L of water at about 80° C. for about 2 hours. After air cooling, water was added to the reactant, an organic phase was separated, and the solvents were distilled. The crude product thus obtained was separated by silica gel column chromatography (using a mixed solvent of toluene and hexane) and recrystallized using a mixed solvent of toluene and EtOH to produce 1.96 g (Yield 84%) of Compound 1 as a white solid. The molecular weight of Compound 1 measured by FAB-MS was 713. Chemical shift values (δ) of Compound 1 measured by $^1$H NMR (300 MHz, CDCl$_3$) were 7.82-7.76(m, 2H), 7.62-7.56(m, 6H), 7.53-7.49(m, 5H), 7.47(d, 2H, J=6.0 Hz), 7.45-7.39(m, 4H), 7.37-7.29(m, 3H), 7.27-7.18(m, 17H). Thus, the synthesis of Compound 1 was recognized.

Synthetic Example 2

Synthesis of Compound 5

Compound 5 was synthesized according to the following reaction scheme.

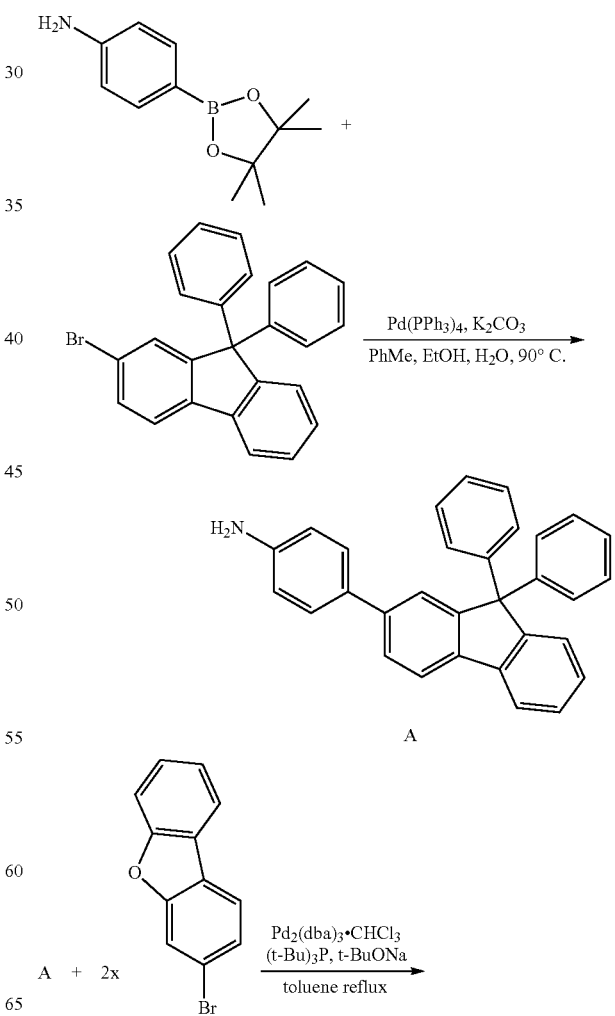

-continued

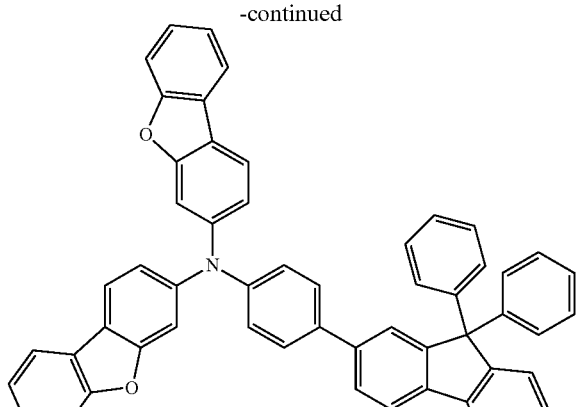

5

Synthesis of Compound A

Under an Ar atmosphere, 2.32 g of 4-(4,4,5,5-tetramethyl-1,3,2-dioxaborolan-2-yl)aniline, 4.00 g of 2-bromo-9,9-diphenylfluorene, 1.04 g of Pd(PPh$_3$)$_4$, 2.79 g of potassium carbonate were added to a 500 mL, three necked flask, followed by heating and stirring in a mixed solvent of 200 mL of toluene, 32 mL of water and 12 mL of ethanol at about 90° C. for about 14 hours. After air cooling, water was added, an organic layer was separated, and the solvents were distilled. The crude product thus obtained was separated by silica gel column chromatography (using a mixed solvent of dichloromethane and hexane) and recrystallized using a mixed solvent of ethyl acetate and hexane to produce 2.18 g (Yield 53%) of Compound A as a white solid (FAB-MS: C$_{31}$H$_{23}$N, measured value 409).

Synthesis of Compound 5

Under an Ar atmosphere, 2.11 g of Compound A, 3.15 g of bromodibenzofuran, 0.384 g of tris(dibenzylideneacetone)dipalladium.CHCl$_3$ ((Pd$_2$(dba)$_3$.CHCl$_3$, and 2.06 g of t-BuONa were added to a 200 mL, three necked flask, and 65 mL of dehydrated toluene and 0.56 mL of 2 M (t-Bu)$_3$P/dehydrated toluene were added, followed by heating and refluxing for about 7 hours. After air cooling, water was added, an organic phase was separated, and the solvents were distilled. The crude product thus obtained was separated by silica gel column chromatography (using a mixed solvent of dichloromethane and hexane) and recrystallized using a mixed solvent of methylene chloride and ethanol to produce 3.30 g (Yield 62%) of Compound 5 as a white solid. The molecular weight of Compound 5 (C$_{55}$H$_{35}$NO$_2$) measured by FAB-MS was 741. Chemical shift values (δ) of Compound 5 measured by $^1$H NMR (300 MHz, CDCl$_3$) were 7.87(dd, 2H), 7.81(d, 2H), 7.80(dd, 2H), 7.54-7.46 (4H), 7.46-7.13(25H). Thus, the synthesis of Compound 5 was recognized.

(1-2-2. Manufacture of Organic EL Device Including Anode-side Hole Transport Material and Anode-Side Hole Transport Layer Doped with Electron Accepting Material)

An organic EL device according to an embodiment was manufactured by the following manufacturing method.

First, with respect to an ITO-glass substrate patterned and washed in advance, surface treatment using UV-Ozone (O$_3$) was conducted. The layer thickness of an ITO layer (first electrode) on a glass substrate was about 150 nm. After ozone treatment, the surface treated substrate was inserted in a glass bell jar type evaporator for forming an organic layer, and an anode-side hole transport layer, an intermediate hole transport layer, an emission layer-side hole transport layer, an emission layer and an electron transport layer were evaporated one by one with a vacuum degree of about 10$^{-4}$ to about 10$^{-5}$ Pa. The layer thickness of each of the anode-side hole transport layer, the intermediate hole transport layer and the emission layer-side hole transport layer was about 10 nm. The layer thickness of the emission layer was about 25 nm, and the layer thickness of the electron transport layer was about 25 nm. Then, the substrate was moved into a glass bell jar type evaporator for forming a metal layer, and an electron injection layer and a second electrode were evaporated with a vacuum degree of about 10$^{-4}$ to about 10$^{-5}$ Pa. The layer thickness of the electron injection layer was about 1 nm and the layer thickness of the second electrode was about 100 nm.

Here, the anode-side hole transport layer, the intermediate hole transport layer and the emission layer-side hole transport layer correspond to a hole transport layer with a stacked structure. The anode-side hole transport layer, the intermediate hole transport layer and the emission layer-side hole transport layer were manufactured in Examples and Comparative Examples using the materials shown in the following Table 1.

In Table 1, for example, the expression of "Compound 2-3, 4-15" means that Compound 2-3 as an anode-side hole transport material was doped with Compound 4-15 as an electron accepting material. The amount doped of the electron accepting material was about 3 wt % on the basis of the amount of the anode-side hole transport material.

In Table 1, Compounds 6-1, 6-2, and 6-3 refer to the following hole transport materials.

(6-1)

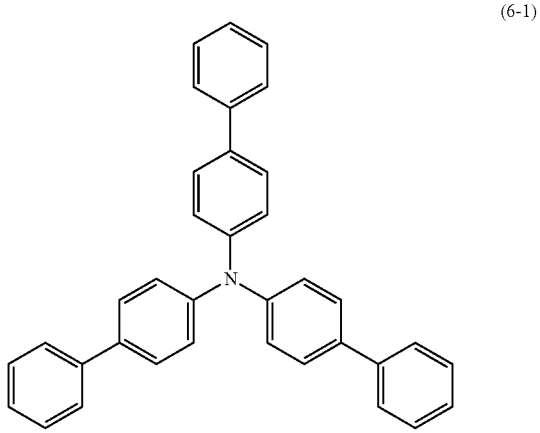

(6-2)

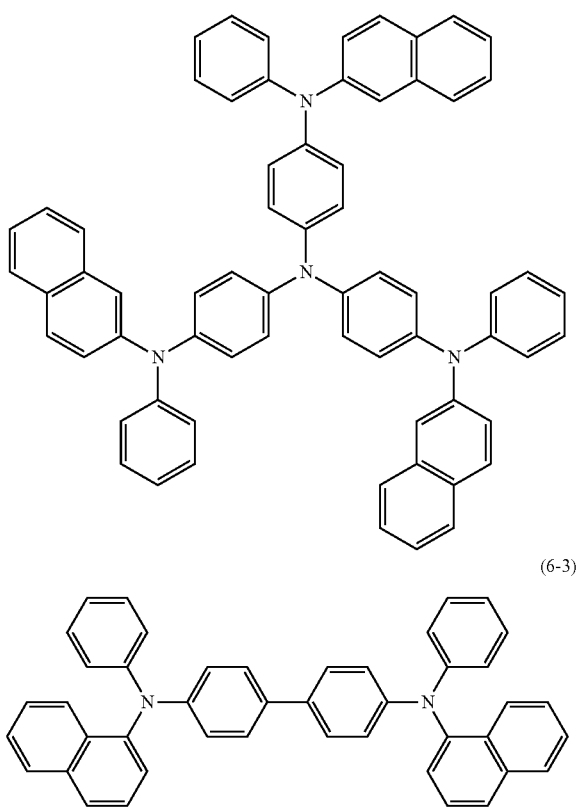

(6-3)

9,10-di(2-naphthyl)anthracene (ADN, Compound 3-2) was used as the host material of the emission layer, and 2,5,8,11-tetra-t-butylperylene (TBP) was used as the dopant material. 3 wt % of the dopant material on the basis of the amount of the host material was added. In addition, the electron transport layer was formed using Alq3, the electron injection layer was formed using LiF, and the second electrode was formed using aluminum (Al).

(1-2-3. Evaluation Results)

Then, the driving voltage, emission efficiency, and half life (emission life) of the organic EL device thus manufactured were evaluated. Evaluation results are shown in the following Table 2. The driving voltage and the emission efficiency in each Example and Comparative Example were obtained by measuring at current density of about 10 mA/cm$^2$. The half life was obtained by measuring a time period for decreasing luminance to half from the initial luminance of about 1,000 cd/m$^2$.

The measurement was conducted using a source meter of 2400 series of Keithley Instruments Co., a Color brightness photometer CS-200 (Konica Minolta holdings Co., Ltd., measurement angle of 1°), and a PC program LabVIEW8.2 (National instruments Co., Ltd. in Japan) in a dark room.

TABLE 1

|  | Anode-side hole transport layer | Intermediate hole transport layer | Emission layer-side hole transport layer |
|---|---|---|---|
| Example 1-1 | Compound 2-3, 4-15 | Compound 2-3 | Compound 1 |
| Example 1-2 | Compound 2-3, 4-15 | Compound 2-3 | Compound 5 |
| Example 1-3 | Compound 6-2, 4-15 | Compound 2-3 | Compound 1 |

TABLE 1-continued

|  | Anode-side hole transport layer | Intermediate hole transport layer | Emission layer-side hole transport layer |
|---|---|---|---|
| Example 1-4 | Compound 2-3, 4-15 | Compound 6-3 | Compound 1 |
| Comparative Example 1-1 | Compound 2-3, 4-15 | Compound 1 | Compound 2-3 |
| Comparative Example 1-2 | Compound 2-3 | Compound 2-3 | Compound 1 |
| Comparative Example 1-3 | Compound 2-3, 4-15 | Compound 2-3 | Compound 6-1 |

TABLE 2

|  | Voltage (V) | Emission efficiency (cd/A) | Emission life (h) |
|---|---|---|---|
| Example 1-1 | 6.1 | 7.7 | 3,800 |
| Example 1-2 | 6.4 | 7.6 | 3,700 |
| Example 1-3 | 6.3 | 7.6 | 3,100 |
| Example 1-4 | 6.3 | 7.7 | 2,900 |
| Comparative Example 1-1 | 6.3 | 7.3 | 2,000 |
| Comparative Example 1-2 | 7.4 | 6.9 | 2,100 |
| Comparative Example 1-3 | 6.4 | 7.3 | 2,300 |

Referring to Tables 1 and 2, it may be seen that the emission efficiency was improved, and the half life was increased for Examples 1-1 to 1-4, when compared to those of Comparative Examples 1-1 to 1-3. It may be seen that the emission efficiency and emission life of the organic EL device were improved by disposing the anode-side hole transport layer, the intermediate hole transport layer, and the emission layer-side hole transport layer between the first electrode and the emission layer.

For example, comparing Example 1-1 with Comparative Example 1-2, it may be seen that the properties of Example 1-1 were better. In Comparative Example 1-2, an electron accepting material (e.g., Compound 4-15) was not doped in the anode-side hole transport layer. Thus, it may be desirable for the electron accepting material to be doped in the anode-side hole transport layer.

In comparing Example 1-1 with Comparative Example 1-1, the properties of Example 1-1 were better. In Comparative Example 1-1, the compounds included in the intermediate hole transport layer and the emission layer-side hole transport layer were reversed compared to those in Example 1-1. Thus, it may be desirable that the emission layer-side hole transport layer (including the compound represented by Formula 1) be adjacent to the emission layer. In addition, by substituting the compounds included in the intermediate hole transport layer and the emission layer-side hole transport layer, remarkable difference of the properties could be obtained.

In comparing Examples 1-1 to 1-3 with Comparative Example 1-3, the properties of Examples 1-1 to 1-3 were better. In Comparative Example 1-3, the emission layer-side hole transport material included in the emission layer-side hole transport layer was Compound 6-1 instead of the compound represented by Formula 1. Thus, it may be desirable that the emission layer-side hole transport layer include the compound represented by Formula 1.

In comparing Examples 1-1 and 1-2 with Example 1-3, the properties of Examples 1-1 and 1-2 were better. In Example 1-3, the anode-side hole transport material included in the anode-side hole transport layer was a hole transport material not including a carbazolyl group, i.e., Compound 6-2, instead of the compound represented by Formula 2. Thus, in an implementation, it may be desirable that the anode-side hole transport material included in the anode-side hole transport layer be the compound represented by Formula 2.

In comparing Examples 1-1 and 1-2 with Example 1-4, the properties of Examples 1-1 and 1-2 were better. In Example 1-4, the intermediate hole transport material included in the intermediate hole transport layer was hole transport material not including a carbazolyl group, i.e., Compound 6-3, instead of the compound represented by Formula 2. Thus, in an implementation, it may be desirable that the intermediate hole transport material included in the intermediate hole transport layer be the compound represented by Formula 2.

As described above, the anode-side hole transport layer doped with the electron accepting material, the intermediate hole transport layer, and the emission layer-side hole transport layer including the compound represented by Formula 1 were stacked between the first electrode (anode) and the emission layer, and the emission efficiency and emission life of the organic EL device were improved.

It may be thought that the hole transport layer may be passivated from electrons not consumed in the emission layer-side hole transport layer, the diffusion of energy in an excited state generated from the emission layer into the hole transport layer may be prevented, and the charge balance of a whole device may be controlled by disposing the emission layer-side hole transport layer including the compound represented by Formula 1. It may be thought that the emission layer-side hole transport layer may help restrain diffusion of the electron accepting material included in the anode-side hole transport layer provided near the first electrode (anode) into the emission layer by disposing the emission layer-side hole transport layer including the compound represented by Formula 1.

<2-1. Configuration of Organic EL Device Including Anode-side Hole Transport Layer Mainly Including Electron Accepting Material>

Hereinafter, an organic EL device including an anode-side hole transport layer mainly including an electron accepting material will be explained referring to FIG. 1.

The organic EL device including the anode-side hole transport layer may include the electron accepting material included the above-mentioned anode-side hole transport material and may have the same general configuration, e.g., the same configuration of a substrate, the same configuration of a first electrode, the same configuration of an emission layer, the same configuration of an electron transport layer, the same configuration of an electron injection layer, the same configuration of a second electrode and the same method of manufacturing an organic EL device as those of the organic EL device described above, e.g., including the anode-side hole transport layer doped with the electron accepting material, and may have a different configuration of the hole transport layer. Thus, the configuration of the hole transport layer will be explained particularly, hereinafter.

(2-1-1. Configuration of Hole Transport Layer)

The hole transport layer 130 may include a hole transport material and may have a hole transporting function. The hole transport layer 130 may be formed, e.g., on the first electrode 120 to a layer thickness (total layer thickness of a stacked structure) within a range from about 10 nm to about 150 nm.

The hole transport layer 130 of the organic EL device 100 according to an embodiment may be formed as a multi layer by stacking from a first electrode 120, an anode-side hole transport layer 131, an intermediate hole transport layer 133 and an emission layer-side hole transport layer 135 one by one. In addition, the ratio of the thicknesses of the layers is not specifically limited.

(2-1-1-1. Configuration of Anode-side Hole Transport Layer)

The anode-side hole transport layer 131 may include an anode-side hole transport material and may be a layer doped with an electron accepting material. For example, the anode-side hole transport layer 131 may be formed on the first electrode 120.

The anode-side hole transport layer 131 may be formed by doping the electron accepting material and may help improve hole injection property from the first electrode 120. Thus, the anode-side hole transport layer 131 may be provided near the first electrode 120. For example, the anode-side hole transport layer 131 may be provided adjacent to (e.g., directly adjacent to or directly contacting) the first electrode 120.

The anode-side hole transport material included in the anode-side hole transport layer 131 may include suitable hole transport materials. Examples of the anode-side hole transport material included in the anode-side hole transport layer 131 may include 1,1-bis[(di-4-tolylamino)phenyl]cyclohexane (TAPC), a carbazole derivative such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), etc.

The electron accepting material included in the anode-side hole transport layer 131 may include suitable electron accepting materials. In an implementation, the electron accepting material included in the anode-side hole transport layer 131 may have a LUMO level within a range of about −9.0 eV to about −4.0 eV, e.g. about −6.0 eV to about −4.0 eV.

Examples of the electron accepting material having the LUMO level within a range of about −9.0 eV to about −4.0 eV may include a compound represented by one of the following Formulae 4-1 to 4-14.

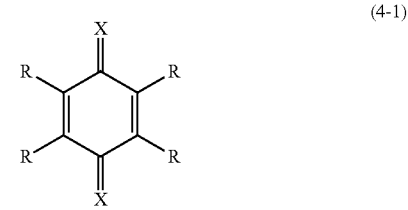

(4-1)

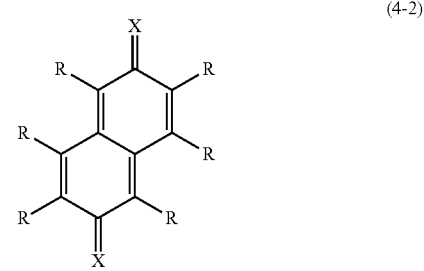

(4-2)

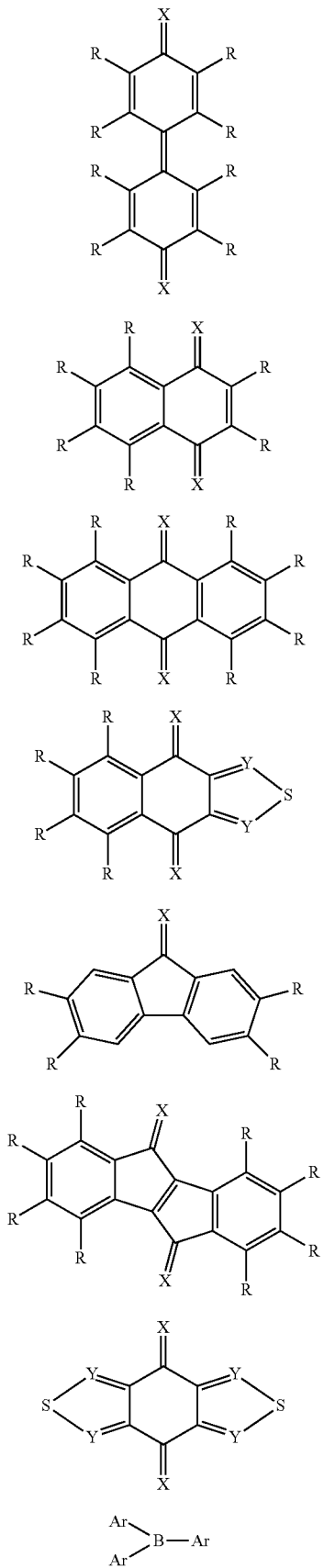

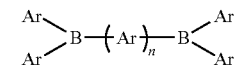
(4-11)

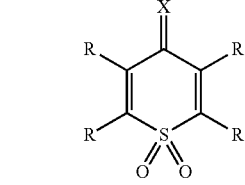
(4-12)

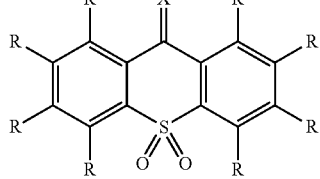
(4-13)

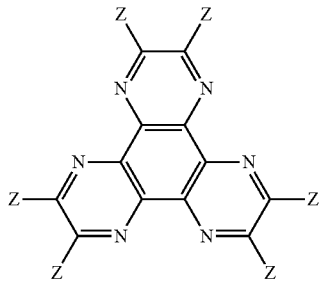
(4-14)

In the above Formulae 4-1 to 4-14, each R may independently be or include, e.g., a hydrogen atom, a deuterium atom, a halogen atom, a fluoroalkyl group having 1 to 50 carbon atoms, a cyano group, an alkoxy group having 1 to 50 carbon atoms, an alkyl group having 1 to 50 carbon atoms, an aryl group having 6 to 50 ring carbon atoms or a heteroaryl group having 5 to 50 ring carbon atoms.

Each Ar may independently be or include, e.g., an aryl group having 6 to 50 ring carbon atoms substituted with an electron withdrawing group or an unsubstituted aryl group having 6 to 50 ring carbon atoms or a substituted or unsubstituted heteroaryl group having 5 to 50 ring carbon atoms, Each Y may be, e.g., a methine group (—CH=) or a nitrogen atom (—N=), each Z may be, e.g., a pseudo-halogen atom or a sulfur (S) atom, n is an integer of 10 and less, and each X may be, e.g., a substituent represented by one of the following formulae X1 to X7.

X1

X2

X3

X4

-continued $$\begin{array}{c} RaO_2C\diagdown\phantom{xx}CO_2Ra \\ \diagdown\!\!\diagup \\ \| \end{array} \quad X5$$

$$\begin{array}{c} NC\diagdown\phantom{xx}CO_2Ra \\ \diagdown\!\!\diagup \\ \| \end{array} \quad X6$$

$$\begin{array}{c} NC\diagdown\phantom{xx}Ra \\ \diagdown\!\!\diagup \\ \| \end{array} \quad X7$$

In X1 to X7, each Ra may be or include, e.g., a hydrogen atom, a deuterium atom, a halogen atom, a fluoroalkyl group having 1 to 50 carbon atoms, a cyano group, an alkoxy group having 1 to 50 carbon atoms, an alkyl group having 1 to 50 carbon atoms, a substituted or unsubstituted aryl group having 6 to 50 ring carbon atoms, or a substituted or unsubstituted heteroaryl group having 5 to 50 ring carbon atoms.

Examples of the substituted or unsubstituted aryl group having 6 to 50 ring carbon atoms represented by R, Ar, and Ra may include a phenyl group, an 1-naphthyl group, a 2-naphthyl group, an 1-anthryl group, a 2-anthryl group, a 9-anthryl group, an 1-phenanthryl group, a 2-phenanthryl group, a 3-phenanthryl group, a 4-phenanthryl group, a 9-phenanthryl group, an 1-naphthacenyl group, a 2-naphthacenyl group, a 9-naphthacenyl group, an 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4''-t-butyl-p-terphenyl-4-yl group, a fluoranthenyl group, a fluorenyl group, etc.

Examples of the substituted or unsubstituted heteroaryl group having 5 to 50 ring carbon atoms represented by R, Ar, and Ra may include an 1-pyrrolyl group, a 2-pyrrolyl group, a 3-pyrrolyl group, a pyridinyl group, a 2-pyridinyl group, a 3-pyridinyl group, a 4-pyridinyl group, an 1-indolyl group, a 2-indolyl group, a 3-indolyl group, a 4-indolyl group, a 5-indolyl group, a 6-indolyl group, a 7-indolyl group, an 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, an 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, an 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, an 1-carbazolyl group, a 2-carbazolyl group, a 3-carbazolyl group, a 4-carbazolyl group, a 9-carbazolyl group, an 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, an 1-acridinyl group, a 2-acridinyl group, a 3-acridinyl group, a 4-acridinyl group, a 9-acridinyl group, an 1,7-phenanthroline-2-yl group, an 1,7-phenanthroline-3-yl group, an 1,7-phenanthroline-4-yl group, an 1,7-phenanthroline-5-yl group, an 1,7-phenanthroline-6-yl group, an 1,7-phenanthroline-8-yl group, an 1,7-phenanthroline-9-yl group, an 1,7-phenanthroline-10-yl group, an 1,8-phenanthroline-2-yl group, an 1,8-phenanthroline-3-yl group, an 1,8-phenanthroline-4-yl group, an 1,8-phenanthroline-5-yl group, an 1,8-phenanthroline-6-yl group, an 1,8-phenanthroline-7-yl group, an 1,8-phenanthroline-9-yl group, an 1,8-phenanthroline-10-yl group, an 1,9-phenanthroline-2-yl group, an 1,9-phenanthroline-3-yl group, an 1,9-phenanthroline-4-yl group, an 1,9-phenanthroline-5-yl group, an 1,9-phenanthroline-6-yl group, an 1,9-phenanthroline-7-yl group, an 1,9-phenanthroline-8-yl group, an 1,9-phenanthroline-10-yl group, an 1,10-phenanthroline-2-yl group, an 1,10-phenanthroline-3-yl group, an 1,10-phenanthroline-4-yl group, an 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, an 1-phenazinyl group, a 2-phenazinyl group, an 1-phenothiazinyl group, a 2-phenothiazinyl group, a 3-phenothiazinyl group, a 4-phenothiazinyl group, a 10-phenothiazinyl group, an 1-phenoxaziny group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, etc.

Examples of the substituted or unsubstituted fluoroalkyl group having 1 to 50 carbon atoms represented by R and Ra may include a perfluoroalkyl group such as a trifluoromethyl group, a pentafluoroethyl group, a heptafluoropropyl group and a heptadecafluorooctane group, a monofluoromethyl group, a difluoromethyl group, a trifluoroethyl group, a tetrafluoropropyl group, an octafluoropentyl group, etc.

Examples of the substituted or unsubstituted alkyl group having 1 to 50 carbon atoms represented by R and Ra may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, an 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, an aminomethyl group, an 1-aminoethyl group, a 2-aminoethyl group, a 2-aminoisobutyl group, an 1,2-diaminoethyl group, an 1,3-diaminoisopropyl group, a 2,3-diamino-t-butyl group, an 1,2,3-triaminopropyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyanopropyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, a cyclopropyl group, a cyclobutyl group, a cyclopentyl group, a cyclohexyl group, a 4-methylcyclohexyl group, an 1-adamantyl group, a 2-adamantyl group, an 1-norbornyl group, a 2-norbornyl group, etc.

The substituted or unsubstituted alkoxy group having 1 to 50 carbon atoms represented by R and Ra may be a group represented by —OY. Examples of Y may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, an 1-hydroxyethyl group, a 2-hydroxyethyl group, a 2-hydroxyisobutyl group, an 1,2-dihydroxyethyl group, an 1,3-dihydroxyisopropyl group, a 2,3-dihydroxy-t-butyl group, an 1,2,3-trihydroxypropyl group, a chloromethyl group, an 1-chloroethyl group, a 2-chloroethyl group, a 2-chloroisobutyl group, an 1,2-dichloroethyl group, an 1,3-dichloroisopropyl group, a 2,3-dichloro-t-butyl group, an 1,2,3-trichloropropyl group, a bromomethyl group, an 1-bromoethyl group, a 2-bromoethyl group, a 2-bromoisobutyl group, an 1,2-dibromoethyl group, an 1,3-dibromoisopropyl group, a 2,3-dibromo-t-butyl group, an 1,2,3-tribromopropyl group, an iodomethyl group, an 1-iodoethyl group, a 2-iodoethyl group, a 2-iodoisobutyl group, an 1,2-diiodoethyl group, an 1,3-diiodoisopropyl group, a 2,3-diiodo-t-butyl group, an 1,2,3-triiodopropyl group, an aminomethyl group, an 1-aminoethyl group, a 2-aminoethyl group, a 2-aminoisobutyl group, an 1,2-diaminoethyl group, an 1,3-diaminoisopropyl group, a 2,3-diamino-t-butyl group, an 1,2,3-triaminopropyl group, a cyanomethyl group, an 1-cyanoethyl group, a 2-cyanoethyl group, a 2-cyanoisobutyl group, an 1,2-dicyanoethyl group, an 1,3-dicyanoisopropyl group, a 2,3-dicyano-t-butyl group, an 1,2,3-tricyanopropyl group, a nitromethyl group, an 1-nitroethyl group, a 2-nitroethyl group, a 2-nitroisobutyl group, an 1,2-dinitroethyl group, an 1,3-dinitroisopropyl group, a 2,3-dinitro-t-butyl group, an 1,2,3-trinitropropyl group, etc.

Examples of the halogen atom represented by R and Ra may include fluorine (F), chlorine (Cl), bromine (Br), iodine (I), etc.

In an implementation, the electron accepting material may include one of the following Compounds 4-15 and 4-16. For example, the LUMO level of Compound 4-15 may be about −4.40 eV, and the LUMO level of Compound 4-16 may be about −5.20 eV.

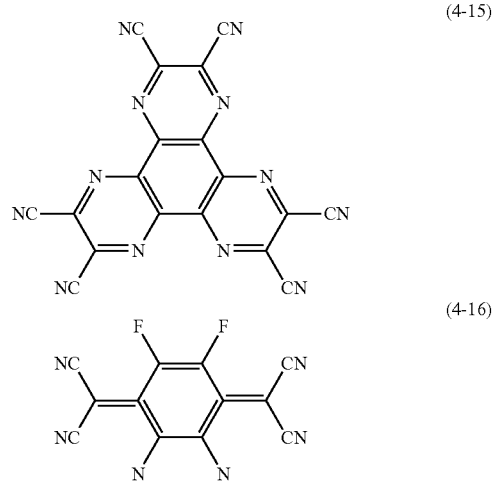

A doping amount of the electron accepting material may be a suitable amount capable of being doped into the anode-side hole transport layer 131. For example, the doping amount of the electron accepting material may be from about 0.1 wt % to about 50 wt % on the basis of the total amount of the anode-side hole transport material included in the anode-side hole transport layer 131, e.g. about 0.5 wt % to about 5 wt %.

(2-1-1-2. Configuration of Intermediate Hole Transport Layer)

The intermediate hole transport layer 133 may include an intermediate hole transport material. The intermediate hole transport layer 133 may be formed, e.g., on the anode-side hole transport layer 131.

The intermediate hole transport material included in the intermediate hole transport layer 133 may include suitable hole transport materials. In an implementation, the intermediate hole transport material may include hole transport materials mentioned above with respect to the anode-side hole transport material.

In an implementation, the hole transport material may include a compound represented by the following Formula 2.

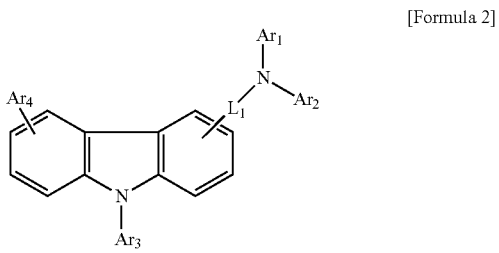

In the above Formula 2, $Ar_1$ to $Ar_3$ may each independently be or include, e.g., a substituted or unsubstituted aryl group having 6 to 50 ring carbon atoms or a substituted or unsubstituted heteroaryl group having 5 to 50 ring carbon atoms. $Ar_4$ may be or include, e.g., a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms. $L_1$ may be a direct linkage (e.g., single bond), a substituted or unsubstituted arylene group having 6 to 18 ring carbon atoms, or a substituted or unsubstituted heteroarylene group having 5 to 15 ring carbon atoms.

Examples of $Ar_1$ to $Ar_3$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In an implementation, $Ar_1$ to $Ar_3$ may include the phenyl group, the biphenyl group, the terphenyl group, the fluorenyl group, the carbazolyl group, the dibenzofuranyl group, etc.

Examples of $Ar_4$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In an implementation, $Ar_4$ may include the phenyl group, the biphenyl group, the terphenyl group, the fluorenyl group, the carbazolyl group, the dibenzofuranyl group, the methyl group, the ethyl group, etc.

Examples of $L_1$ (other than the direct linkage/single bond) may include a phenylene group, a biphenylene group, a terphenylene group, a naphthylene group, an anthrylene group, a phenanthrylene group, a fluorenylene group, an indenylene group, a pyrenylene group, an acetonaphthenylene group, a fluoranthenylene group, a triphenylenylene group, a pyridylene group, a furanylene group, a pyranylene group, a thienylene group, a quinolylene group, an isoquinolylene group, a benzofuranylene group, a benzothienylene group, an indolylene group, a carbazolylene group, a benzoxazolylene group, a benzothiazolylene group, a kinokisariren group, a benzoimidazolylene group, a pyrazolylene group, a dibenzofuranylene group, a dibenzothienylene group, etc. In an implementation, $L_1$ may include the direct linkage, the phenylene group, the biphenylene group, the terphenylene group, the fluorenylene group, the carbazolylene group or the dibenzofuranylene group.

In an implementation, the compound represented by Formula 2 may include one of the following Compounds 2-1 to 2-16.

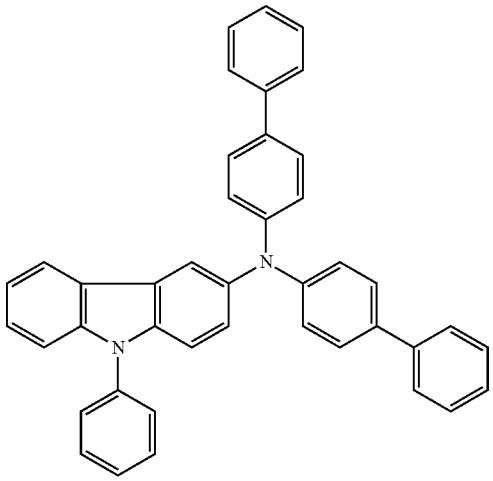

(2-1)

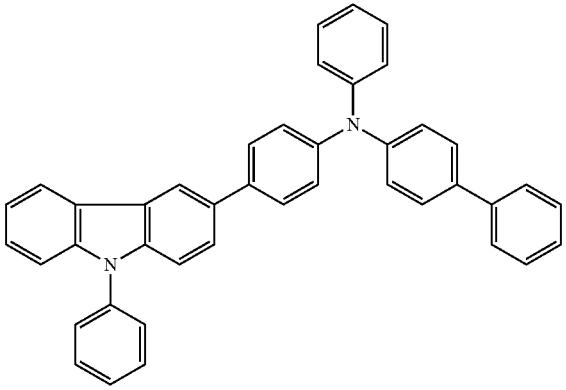

(2-2)

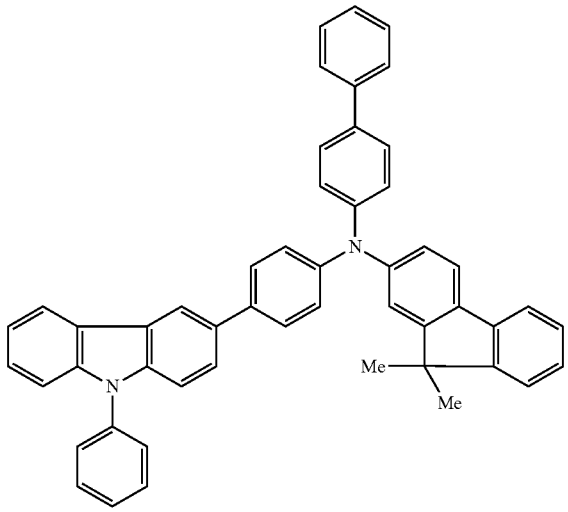

(2-3)

-continued
(2-4)
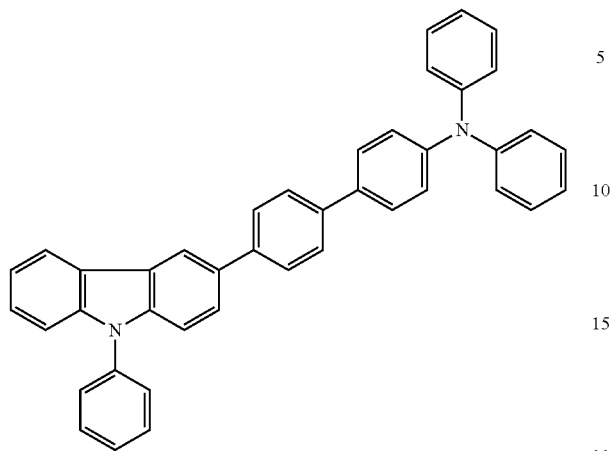
(2-7)
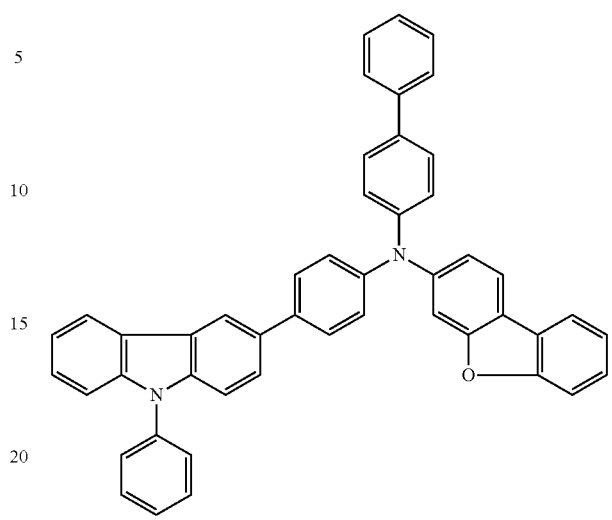
(2-5)
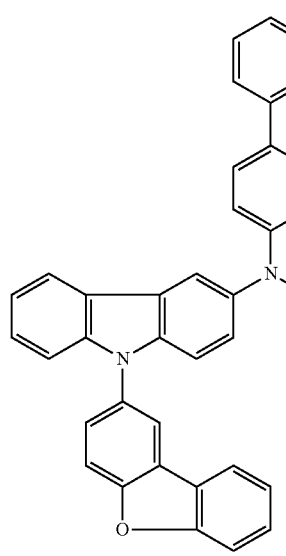
(2-8)
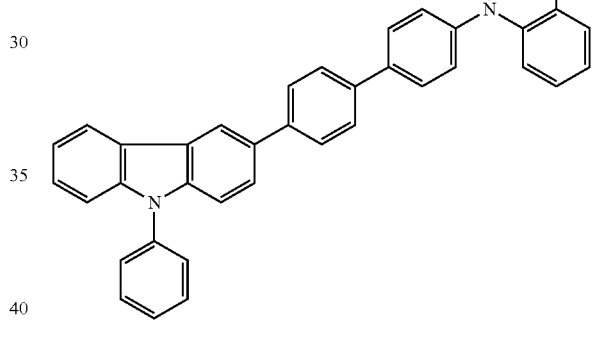
(2-6)
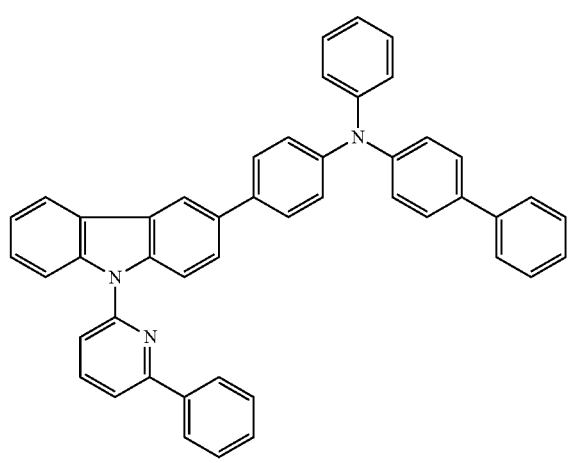
(2-9)
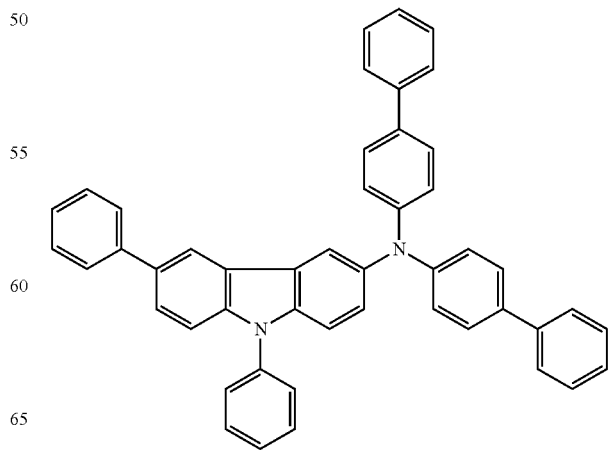

(2-10)
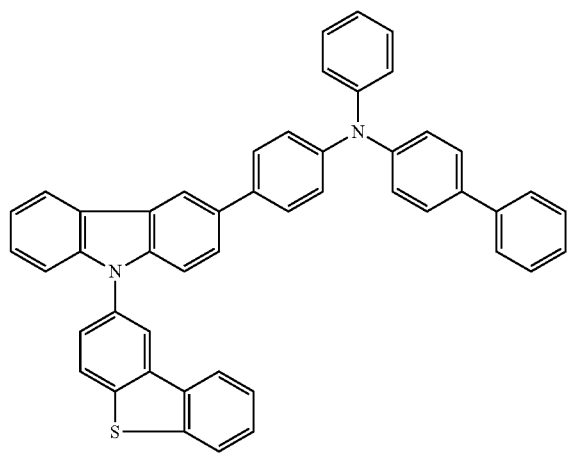
(2-11)
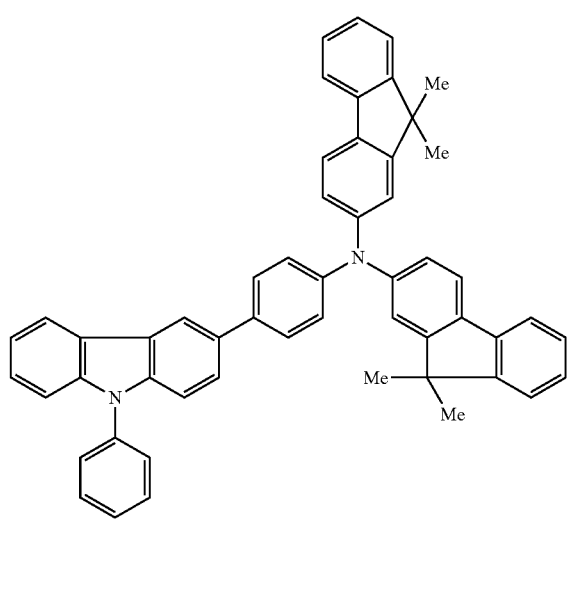
(2-12)
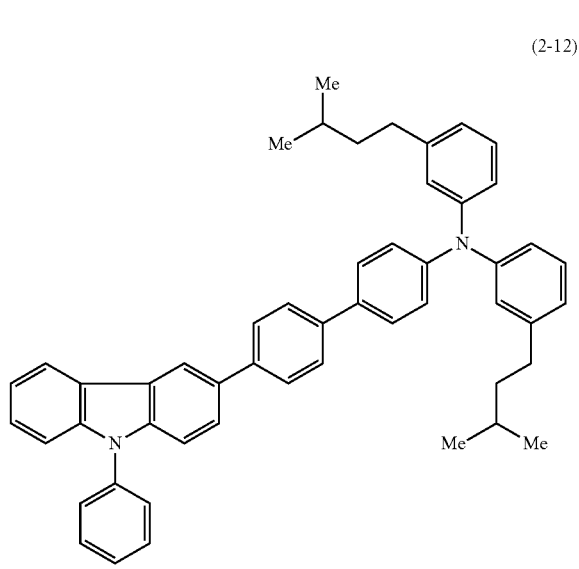
(2-13)
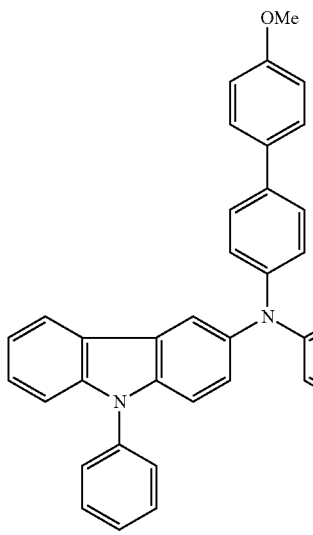
(2-14)
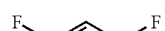
(2-15)
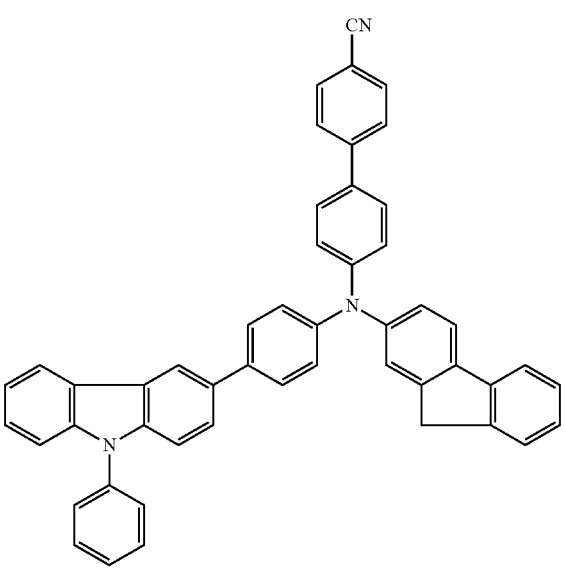

(2-16)

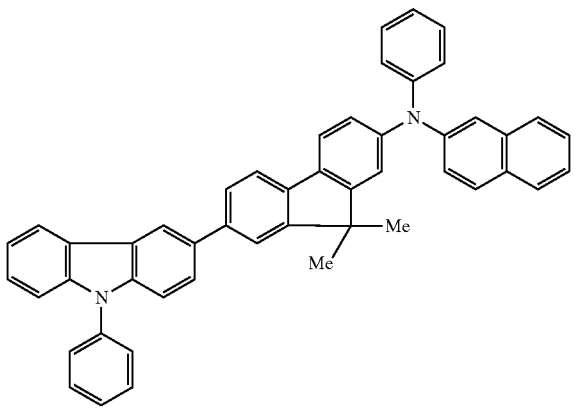

The intermediate hole transport layer 133 may include the compound represented by the above Formula 2 as the intermediate hole transport material and may help improve the hole transporting property of the hole transport layer 130. Thus, the emission efficiency of the organic EL device 100 may be improved.

The compound represented by Formula 2 may be included in the anode-side hole transport layer 131 as the anode-side hole transport material. In the case that the anode-side hole transport layer 131 includes the compound represented by Formula 2 as the anode-side hole transport material, the hole transporting property of the hole transport layer 130 may be improved. Thus, the emission efficiency of the organic EL device 100 may be improved.

In an implementation, in the case that the ratio included of a carbazole derivative (such as the compound represented by Formula 2) is high in the hole transport layer 130, the emission life of the organic EL device 100 may be improved.

The anode-side hole transport layer 131 may further include other hole transport materials as the anode-side hole transport materials in addition to the compound represented by Formula 2.

(2-1-1-3. Configuration of Emission Layer-side Hole Transport Layer)

The emission layer-side hole transport layer 135 may include a compound represented by the following Formula 1. The emission layer-side hole transport layer 135 may be formed, e.g., on the intermediate hole transport layer 133, adjacent to (e.g., directly adjacent to or directly contacting) the emission layer 140.

[Formula 1]

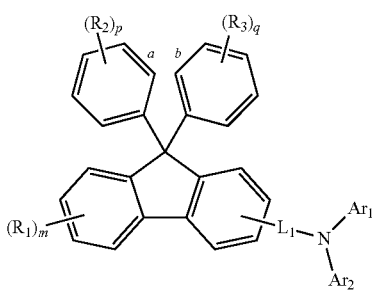

In Formula 1, $Ar_1$ and $Ar_2$ may each independently be or include, e.g., a substituted or unsubstituted aryl group having 6 to 50 ring carbon atoms or a substituted or unsubstituted heteroaryl group having 5 to 50 ring carbon atoms.

$R_1$ to $R_3$ may each independently be or include, e.g., a substituted or unsubstituted alkyl group having 1 to 20 carbon atoms, a substituted or unsubstituted aryl group having 6 to 50 ring carbon atoms, or a substituted or unsubstituted heterocyclic group having 3 to 50 ring carbon atoms. In an implementation, adjacent ones of $R_1$ to $R_3$ may be separate, or may be bound to form a ring.

In an implementation, m may be an integer of 0 to 4 and p and q may each independently be an integer of 0 to 5. $L_1$ may be, e.g., a direct linkage (e.g., a single bond), a substituted or unsubstituted arylene group having 6 to 18 ring carbon atoms, or a substituted or unsubstituted heteroarylene group having 5 to 15 ring carbon atoms. In an implementation, carbon atoms a and b may be separate from one another or may combined via a direct linkage.

Examples of $Ar_1$ and $Ar_2$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In an implementation, $Ar_1$ and $Ar_2$ may include the phenyl group, the biphenyl group, the terphenyl group, the fluorenyl group, the carbazolyl group and the dibenzofuranyl group.

Examples of $R_1$ to $R_3$ may include a methyl group, an ethyl group, a propyl group, an isopropyl group, a cyclopropyl group, a butyl group, an isobutyl group, a t-butyl group, a cyclobutyl group, a pentyl group, an isopentyl group, a neopentyl group, a cyclopentyl group, a hexyl group, a cyclohexyl group, a heptyl group, a cycloheptyl group, an octyl group, a nonyl group, a decyl group, etc., other than the particular examples of $Ar_1$ and $Ar_2$.

Substituent of $Ar_1$ and $Ar_2$ and $R_1$ to $R_3$ may include an alkyl group, an alkoxy group, an aryl group and a heteroaryl group. Examples of the aryl group and the heteroaryl group may be the same as described above. Examples of the alkyl group, the aryl group, and the heteroaryl group may be the same as described above. Examples of the alkoxy group may be an alkoxy group substituted with the alkyl group.

Examples of $L_1$ (other than the direct linkage/single bond) may include a divalent substituent of $Ar_1$ and $Ar_2$. Examples of $L_1$ other than the direct linkage may include a phenylene group, a biphenylene group, a terphenylene group, a naphthylene group, an anthrylene group, a phenanthrylene group, a fluorirane group, an indanediyl group, a pyrenediyl group, an acenaphthenediyl group, a fluoranthenediyl group, a triphenylenediyl group, a pyridinediyl group, a pyranediyl group, a quinolinediyl group, an isoquinolinediyl group, a benzofurandiyl group, a benzothiophenediyl group, an indolediyl group, a carbazolediyl group, a benzoxazolediyl group, a benzothiazolediyl group, a quinoxalinediyl group, a benzoimidazolediyl group, and a dibenzofurndiyl group. In an implementation, the phenylene group, the terphenylene group, the fluoriranediyl group, the carbazolediyl group and the dibenzofuranediyl group may be used.

In an implementation, the compound represented by Formula 1 may include one of the following Compounds 1 to 12.

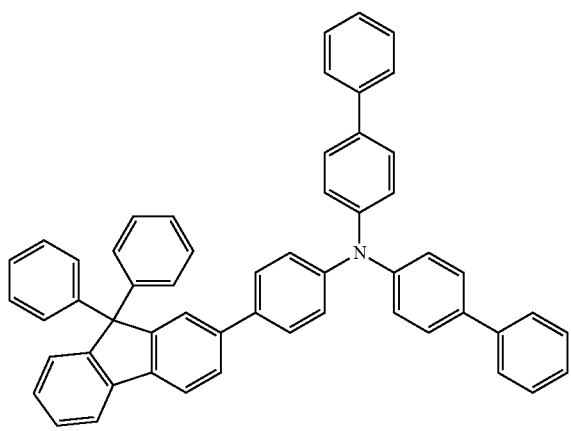
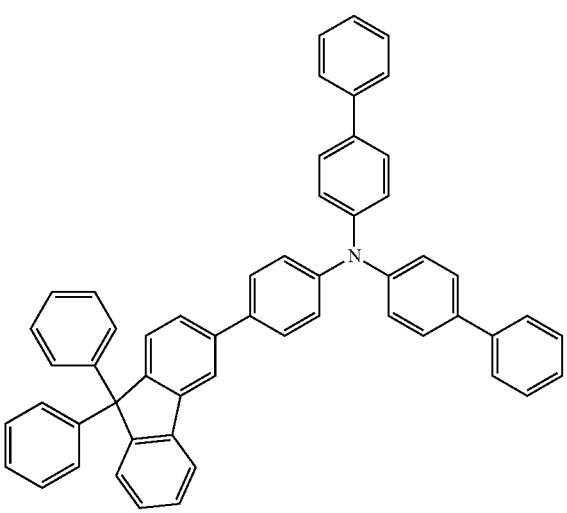
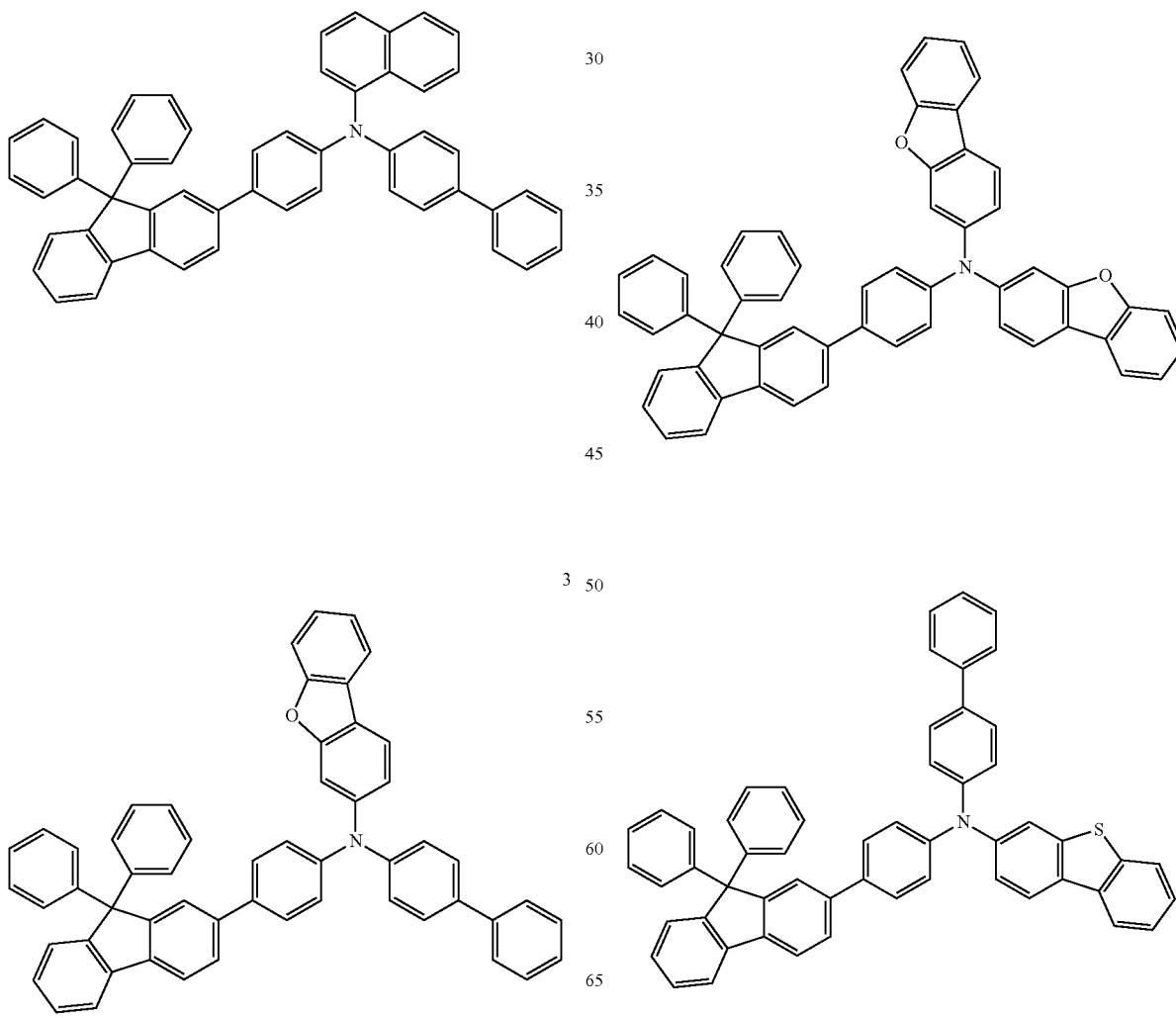

-continued

7
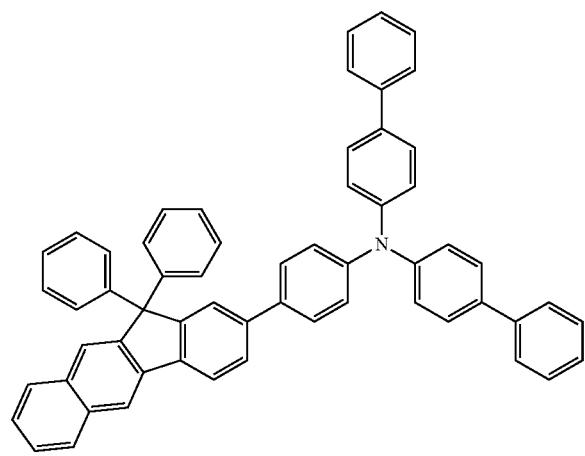

8
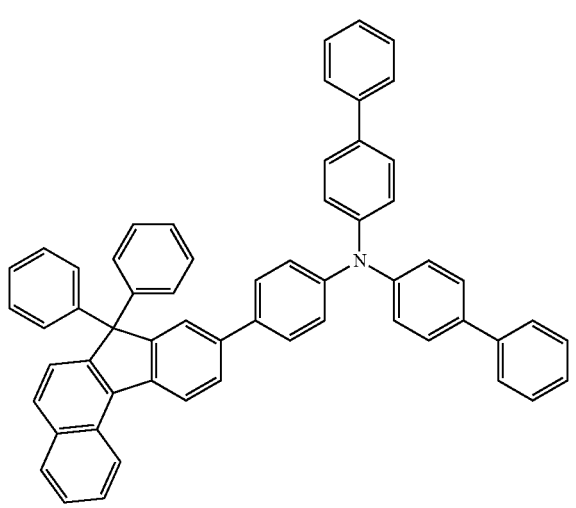

9
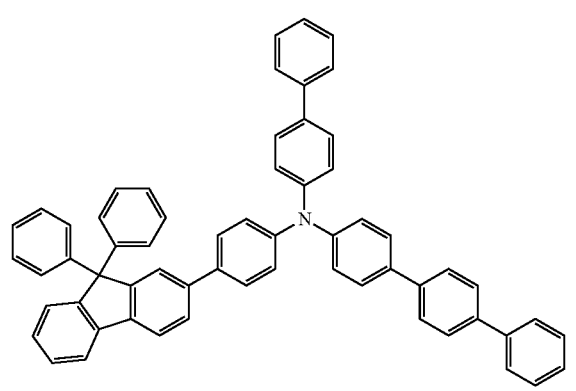

-continued

10
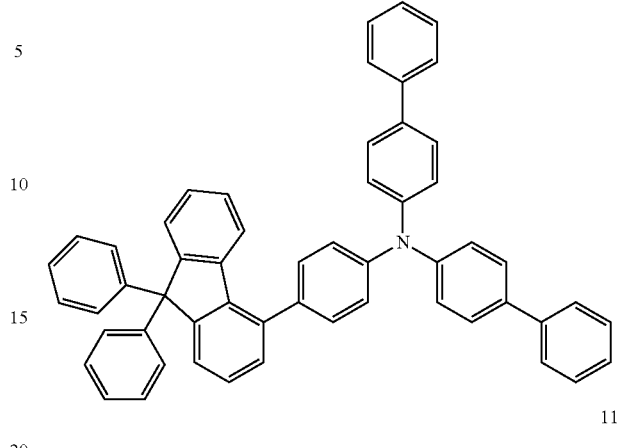

11

12

The emission layer-side hole transport layer 135 may include the compound represented by the above Formula 1 as the emission layer-side hole transport material and may passivate the hole transport layer 130 from electrons not consumed in the emission layer 140. In addition, the emission layer-side hole transport layer 135 may include the compound represented by the above Formula 1, and the diffusion of energy in an excited state generated in the emission layer 140 into the hole transport layer 130 may be reduced and/or prevented. Thus, according to this configuration, the emission layer-side hole transport layer 135 may help improve the current flow durability of the hole transport layer 130.

The emission layer-side hole transport layer 135 may be formed near the emission layer 140. For example, the emission layer-side hole transport layer 135 may be formed adjacent to (e.g., directly adjacent to or directly contacting) the emission layer 140 to help effectively prevent the diffusion of the electrons or the energy from the emission layer 140.

The emission layer-side hole transport layer 135 may include the compound represented by the above Formula 1, the charge balance of the whole organic EL device 100 may be controlled, and the diffusion of the electron accepting material doped in the anode-side hole transport layer 131 into the emission layer 140 may be restrained. Accordingly, the emission layer-side hole transport layer 135 may help improve the whole charge transport property of the hole transport layer 130.

The emission layer-side hole transport layer 135 may include the compound represented by the above Formula 1, and the charge transport property and current flow durability of the hole transport layer 130 may be improved. Thus, the emission efficiency and emission life of the organic EL device 100 may be improved.

As described above, the hole transport layer 130 including the anode-side hole transport layer 131, the intermediate hole transport layer 133 and the emission layer-side hole transport layer 135 may help improve the current flow durability and hole transport property of the organic EL device 100. Thus, the organic EL device 100 according to an embodiment may have improved emission efficiency and emission life.

<2-2. Examples>

Hereinafter, organic EL devices according to exemplary embodiments will be explained in particular referring to Examples and Comparative Examples. The following embodiments are only for illustration, and the organic EL devices according to exemplary embodiments are not limited thereto.

(2-2-1. Synthesis of Compounds)

Synthetic Example 1

Synthesis of Compound 1

Compound 1 was synthesized according to the following reaction scheme.

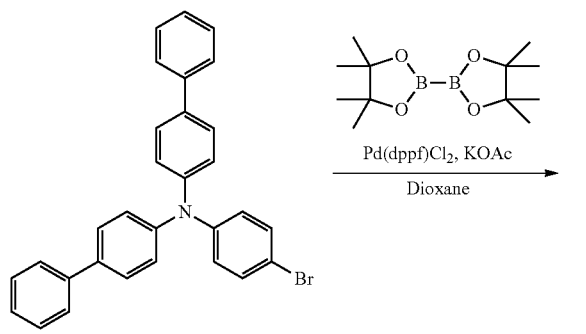

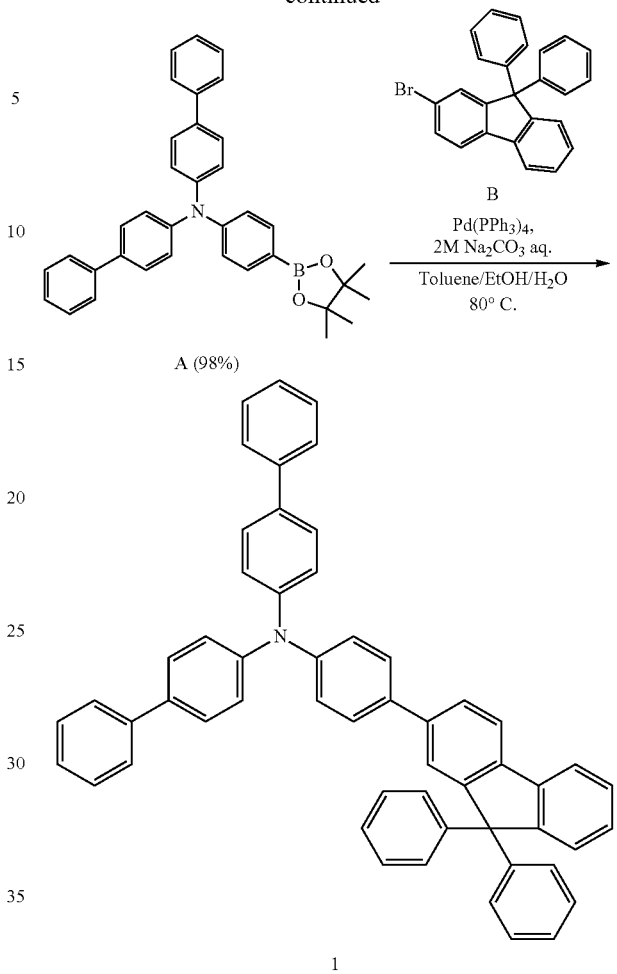

(Synthesis of Compound a in Formula 13)

Under an Ar atmosphere, 53.8 g of N-[1,1'-biphenyl]-4-yl-N-(4-bromophenyl)-[1,1'-biphenyl-4-amine, 6.46 g of [1,1'-bis(diphenylphosphino) ferrocene] dichloropalladium.$CH_2Cl_2$(Pd(dppf)$Cl_2$.$CH_2Cl_2$), 33.3 g of potassium acetate (KOAc), and 33.0 g of bis(pinacolato) diboron were added to a 2 L, flask, followed by degassing under vacuum in 750 mL of a dioxane solvent at about 100° C. for about 12 hours. After that, the solvents were distilled, $CH_2Cl_2$ and water were added, an organic phase was separated, magnesium sulfate and activated clay were added, filtering with suction was performed, and the solvents were distilled. The crude product thus obtained was separated by silica gel column chromatography (using a mixed solvent of dichloromethane and hexane) to produce 56.8 g (Yield 98%) of Compound A as a white solid (FAB-MS: $C_{36}H_{34}BNO_2$, measured value 523).

Synthesis of Compound 1

Under an Ar atmosphere, 1.66 g of Compound A, 1.52 g of Compound B, 0.11 g of tetrakis(triphenylphosphine) palladium(0) (Pd(PPh$_3$)$_4$) and 1.1 g of sodium carbonate were added to a 200 mL, three necked flask, followed by heating and stirring in a mixed solvent of 19 mL of EtOH and 9.0 L of water at about 80° C. for about 2 hours. After air cooling, water was added, an organic layer was separated, and solvents were distilled. The crude product thus obtained was separated by silica gel column chromatography (using a mixed solvent of toluene and hexane) and recrystallized using a mixed solvent of toluene and EtOH to produce 1.96 g (Yield 84%) of Compound 1 as a white solid. The molecular weight of Compound 1 ($C_{55}H_{39}N$) measured by FAB-MS was 713. The chemical shift values (δ) of Compound 1 measured by $^1$H NMR (300 MHz, $CDCl_3$) were 7.82-7.76(m, 2H), 7.62-7.56(m, 6H), 7.53-7.49(m, 5H), 7.47(d, 2H, J=6.0 Hz), 7.45-7.39(m, 4H), 7.37-7.29(m, 3H), 7.27-7.18(m, 17H). Thus, the synthesis of Compound 1 was recognized.

Synthetic Example 2

Synthesis of Compound 5

Compound 5 was synthesized according to the following reaction scheme.

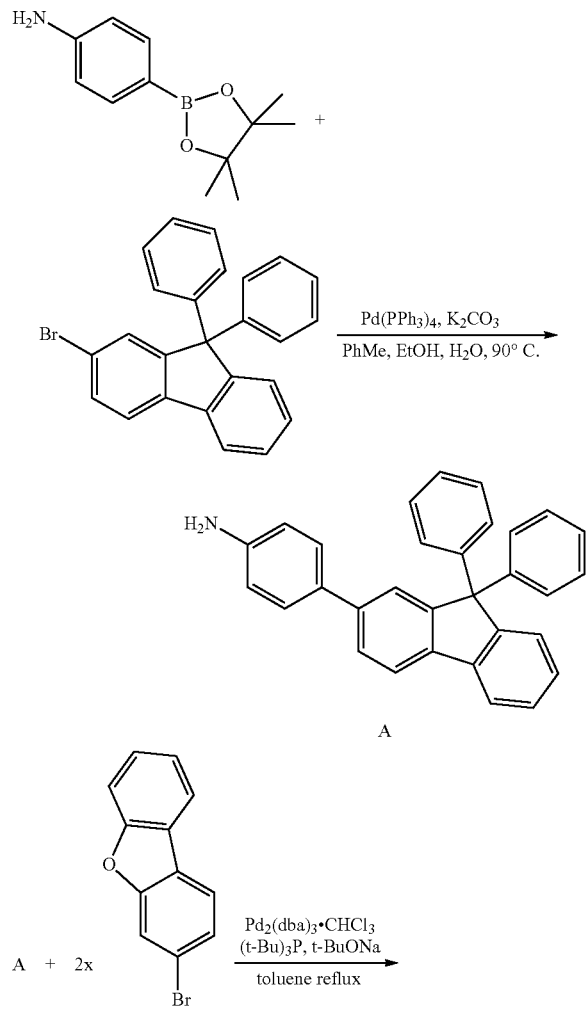

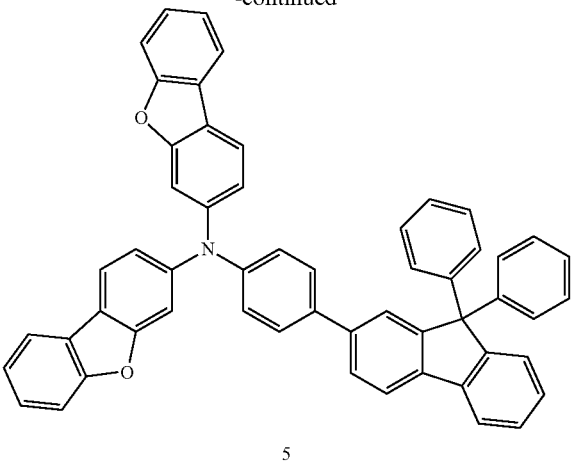

5

Synthesis of Compound A

Under an Ar atmosphere, 2.32 g of 4-(4,4,5,5-tetramethyl-1,3,2-dioxaborolan-2-yl)aniline, 4.00 g of 2-bromo-9,9-diphenylfluorene, 1.04 g of $Pd(PPh_3)_4$, and 2.79 g of potassium carbonate were added to a 500 mL, three necked flask, followed by heating and stirring in a mixed solvent of 200 mL of toluene, 32 mL of water and 12 mL of ethanol at about 90° C. for about 14 hours. After air cooling, water was added, an organic layer was separated, and the solvents were distilled. The crude product thus obtained was separated by silica gel column chromatography (using a mixed solvent of dichloromethane and hexane) and recrystallized using a mixed solvent of ethyl acetate and hexane to produce 2.18 g (Yield 53%) of Compound A as a white solid. (FAB-MS: $C_{31}H_{23}N$, measured value, 409)

Synthesis of Compound 5

Under an Ar atmosphere, 2.11 g of Compound A, 3.15 g of 3-bromodibenzofuran, 0.384 g of tris(dibenzylideneacetone)dipalladium.$CHCl_3$ ($Pd_2(dba)_3.CHCl_3$), 2.06 g of t-BuONa were added to a 200 mL, three necked flask, and 65 mL of dehydrated toluene and 0.56 mL of a 2 M $(t-Bu)_3P$/dehydrated toluene were added thereto, followed by heating, refluxing and stirring for about 7 hours. After air cooling, water was added, an organic layer was separated, and the solvents were distilled. The crude product thus obtained was separated by silica gel column chromatography (using a mixed solvent of dichloromethane and hexane) and recrystallized using a mixed solvent of methylene chloride and ethanol to produce 3.30 g (Yield 62%) of Compound 5 as a white solid. The molecular weight of Compound 5 ($C_{55}H_{35}NO_2$) measured by FAB-MS was 741. The chemical shift values (δ) of Compound 5 measured by $^1$H NMR (300 MHz, $CDCl_3$) were 7.87(dd, 2H), 7.81(d, 2H), 7.80(dd, 2H), 7.54-7.46(4H), 7.46-7.13(25H). Thus, the synthesis of Compound 5 was recognized.

(2-2-2. Manufacture of Organic EL Device Including Anode-side Hole Transport Material Mainly Including Electron Accepting Material)

An organic EL device according to an embodiment was manufactured by the following manufacturing method.

First, with respect to an ITO-glass substrate patterned and washed in advance, surface treatment using UV-Ozone ($O_3$) was conducted. The layer thickness of an ITO layer (first electrode) on a glass substrate was about 150 nm. After ozone treatment, the surface treated substrate was inserted in a glass bell jar type evaporator for forming an organic layer, and an anode-side hole transport layer, an intermediate hole transport layer, an emission layer-side hole transport layer, an emission layer and an electron transport layer were evaporated one by one with a vacuum degree of about $10^{-4}$ to about $10^{-5}$ Pa. The layer thickness of each of the anode-side hole transport layer, the intermediate hole transport layer and the emission layer-side hole transport layer was about 10 nm. The layer thickness of the emission layer was about 25 nm, and the layer thickness of the electron transport layer was about 25 nm. Then, the substrate was moved into a glass bell jar type evaporator for forming a metal layer, and the electron injection layer and the second electrode were evaporated with a vacuum degree of about $10^{-4}$ to about $10^{-5}$ Pa. The layer thickness of the electron injection layer was about 1 nm and the layer thickness of the second electrode was about 100 nm.

The anode-side hole transport layer, the intermediate hole transport layer, and the emission layer-side hole transport layer correspond to a hole transport layer with a stacked structure. The anode-side hole transport layer, the intermediate hole transport layer, and the emission layer-side hole transport layer were manufactured in the Examples and Comparative Examples using the materials shown in the following Table 3.

In Table 3, for example, the expression of "Compound 2-3, 4-15" means that Compound 2-3 as an anode-side hole transport material was doped with Compound 4-15 as an electron accepting material. The doping amount of the electron accepting material was about 3 wt % on the basis of the amount of the anode-side hole transport material.

In Table 3, Compounds 6-1, 6-2, and 6-3 refer to the following hole transport materials.

(6-1)

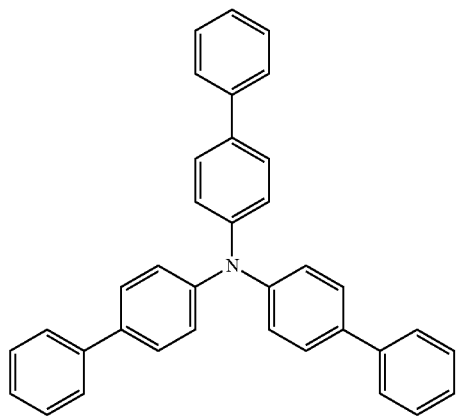

(6-2)

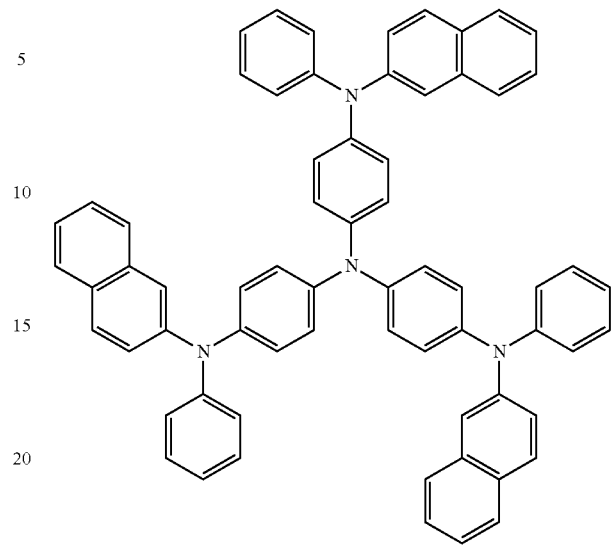

(6-3)

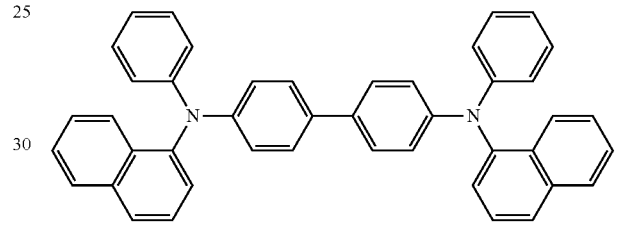

As the host material of the emission layer, 9,10-di(2-naphthyl)anthracene (ADN, Compound 3-2) was used, and as a dopant material, 2,5,8,11-tetra-t-butylperylene (TBP) was used. 3 wt % of the dopant material on the basis of the amount of the host material was added. In addition, the electron transport layer was formed using Alq3, the electron injection layer was formed using LiF, and the second electrode was formed using aluminum (Al).

(2-2-3. Evaluation Results)

Then, the driving voltage, emission efficiency, and half life (emission life) of the organic EL device thus manufactured were evaluated. Evaluation results are shown together in the following Table 4. The driving voltage and the emission efficiency in each Example and Comparative Example were obtained by measuring at a current density of about 10 mA/cm$^2$. The emission life was obtained by measuring a time period for decreasing luminance to half from the initial luminance of about 1,000 cd/m$^2$.

The measurement was conducted using a source meter of 2400 series of Keithley Instruments Co., a Color brightness photometer CS-200 (Konica Minolta holdings Co., Ltd., measurement angle of 1°), and a PC program LabVIEW8.2 (National instruments Co., Ltd. in Japan) in a dark room.

TABLE 3

|  | Anode-side hole transport layer | Intermediate hole transport layer | Emission layer-side hole transport layer |
|---|---|---|---|
| Example 2-1 | Compound 2-3, 4-15 | Compound 2-3 | Compound 1 |
| Example 2-2 | Compound 2-3, 4-15 | Compound 2-3 | Compound 5 |
| Example 2-3 | Compound 6-2, 4-15 | Compound 2-3 | Compound 1 |

TABLE 3-continued

|  | Anode-side hole transport layer | Intermediate hole transport layer | Emission layer-side hole transport layer |
| --- | --- | --- | --- |
| Example 2-4 | Compound 2-3, 4-15 | Compound 6-3 | Compound 1 |
| Comparative Example 2-1 | Compound 2-3, 4-15 | Compound 1 | Compound 2-3 |
| Comparative Example 2-2 | Compound 2-3 | Compound 2-3 | Compound 1 |
| Comparative Example 2-3 | Compound 2-3, 4-15 | Compound 2-3 | Compound 6-1 |

TABLE 4

|  | Voltage (V) | Emission efficiency (cd/A) | Emission life (h) |
| --- | --- | --- | --- |
| Example 2-1 | 6.1 | 7.7 | 3,800 |
| Example 2-2 | 6.4 | 7.6 | 3,700 |
| Example 2-3 | 6.3 | 7.6 | 3,100 |
| Example 2-4 | 6.3 | 7.7 | 2,900 |
| Comparative Example 2-1 | 6.3 | 7.3 | 2,000 |
| Comparative Example 2-2 | 7.4 | 6.9 | 2,100 |
| Comparative Example 2-3 | 6.4 | 7.3 | 2,300 |

Referring to the results in Tables 3 and 4, the emission efficiency was improved, and the half life was increased for Examples 2-1 to 2-4 with respect to Comparative Examples 2-1 to 2-3. It may be seen that the emission efficiency and emission life of the organic EL device may be improved by providing the anode-side hole transport layer, the intermediate hole transport layer, and the emission layer-side hole transport layer between the first electrode and the emission layer.

For example, in comparing Example 2-1 with Comparative Example 2-2, the properties of Example 2-1 were better. In Comparative Example 2-2, the electron accepting material (e.g., Compound 4-15) was not doped in the anode-side hole transport layer. It may be desirable that the electron accepting material be doped in the anode-side hole transport layer.

In comparing Example 2-1 with Comparative Example 2-1, the properties of Example 2-1 were better. In Comparative Example 2-1, the compound included in the intermediate hole transport layer and the emission layer-side hole transport layer were reversed relative to those of Example 2-1. It may be desirable that the emission layer-side hole transport layer including the compound represented by Formula 1 be adjacent to the emission layer. In addition, remarkably improved properties were obtained by changing the compound included in the intermediate hole transport layer and the emission layer-side hole transport layer.

In comparing Examples 2-1 to 2-3 with Comparative Example 2-3, the properties of Examples 2-1 to 2-3 were better. In Comparative Example 2-3, the emission layer-side hole transport material included in the emission layer-side hole transport layer was Compound 6-1, instead of the compound represented by Formula 1. It may be desirable that the emission layer-side hole transport layer be included in the compound represented by Formula 1.

In comparing Examples 2-1 and 2-2 with Example 2-3, the properties of Examples 2-1 and 2-2 were better. In Examples 2-3, the anode-side hole transport material included in the anode-side hole transport layer was Compound 6-2, instead of the compound represented by Formula 2. In an implementation, it may be desirable that the anode-side hole transport material included in the anode-side hole transport be was the compound represented by Formula 2.

If comparing Examples 2-1 and 2-2 with Example 2-4, the properties of Examples 2-1 and 2-2 were better. In Example 2-4, the intermediate hole transport material included in the intermediate hole transport layer was a hole transport material not including a carbazolyl group, i.e., Compound 6-3, instead of the compound represented by Formula 2. In an implementation, it may be desirable that the intermediate hole transport material included in the intermediate hole transport layer be the compound represented by Formula 2.

As explained above, the anode-side hole transport layer doped with the electron accepting material, the intermediate hole transport layer, and the emission layer-side hole transport layer including the compound represented by Formula 1 were stacked between the first electrode (anode) and the emission layer, and the emission efficiency and emission life of the organic EL device were improved.

It may be thought that the hole transport layer may be passivated from electrons not consumed in the emission layer-side hole transport layer, the diffusion of energy in an excited state generated from the emission layer into the hole transport layer may be prevented, and the charge balance of a whole device may be controlled by disposing the emission layer-side hole transport layer including the compound represented by Formula 1. It may be thought that the emission layer-side hole transport layer may help restrain the diffusion of the electron accepting material included in the anode-side hole transport layer provided near the first electrode (anode) into the emission layer by disposing the emission layer-side hole transport layer including the compound represented by Formula 1.

As described above, an anode side hole transport layer, an intermediate hole transport layer, and an emission layer side hole transport layer may be provided between an anode and an emission layer, and the emission efficiency and emission life of an organic EL device may increase.

By way of summation and review, a hole transport material or a hole transport layer may be included in an organic EL device. For example, a hole transport material may include a carbazolyl group and may be used in a hole transport layer. In addition, an electron accepting material may be added to a hole transport layer, and a hole transport layer may be formed of a stacked structure using a plurality of layers.

The embodiments may provide a device having satisfactory values for the emission efficiency and emission life of an organic EL device.

The embodiments may provide an organic EL device having improved emission efficiency and emission life.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic electroluminescent (EL) device, comprising:
an anode;
an emission layer;
an anode-side hole transport layer between the anode and the emission layer, the anode-side hole transport layer including an anode-side hole transport material and being doped with an electron accepting material;
an intermediate hole transport layer between the anode-side hole transport layer and the emission layer, the intermediate hole transport layer including an intermediate hole transport material; and
an emission layer-side hole transport layer between the intermediate hole transport layer and the emission layer, the emission layer-side hole transport layer being adjacent to the emission layer,
wherein the intermediate hole transport layer and the emission layer-side hole transport layer are in contact with each other,
wherein the emission layer-side hole transport layer includes an emission layer-side hole transport material represented by the following Formula 1:

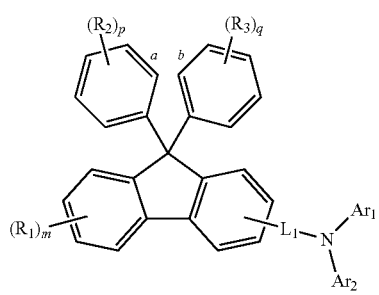

[Formula 1]

wherein, in Formula 1,
Ar$_1$ and Ar$_2$ are each independently a substituted or unsubstituted aryl group having 6 to 50 ring carbon atoms or a substituted or unsubstituted heteroaryl group having 5 to 50 ring carbon atoms,
R$_1$ to R$_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of R$_1$ to R$_3$ being separate or bound to form a ring,
m is an integer of 0 to 4,
p and q are each independently an integer of 0 to 5,
L$_1$ is a direct linkage, a substituted or unsubstituted arylene group having 6 to 18 ring carbon atoms, or a substituted or unsubstituted heteroarylene group having 5 to 15 ring carbon atoms, and
carbon atoms a and b are separate.

2. The organic EL device as claimed in claim 1, wherein the intermediate hole transport material includes a compound represented by the following Formula 2:

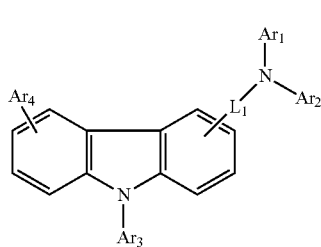

[Formula 2]

wherein, in Formula 2,
Ar$_1$ to Ar$_3$ are each independently a substituted or unsubstituted aryl group having 6 to 50 ring carbon atoms or a substituted or unsubstituted heteroaryl group having 5 to 50 ring carbon atoms,
Ar$_4$ is a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms, and
L$_1$ is a direct linkage, a substituted or unsubstituted arylene group having 6 to 18 ring carbon atoms, or a substituted or unsubstituted heteroarylene group having 5 to 15 ring carbon atoms.

3. The organic EL device as claimed in claim 2, wherein the anode-side hole transport material includes the compound represented by Formula 2.

4. The organic EL device as claimed in claim 1, wherein the electron accepting material has a lowest unoccupied molecular orbital (LUMO) level of about −9.0 eV to about −4.0 eV.

5. The organic EL device as claimed in claim 1, wherein the anode-side hole transport layer is adjacent to the anode.

6. The organic EL device as claimed in claim 1, wherein the emission layer includes a compound represented by the following Formula 3:

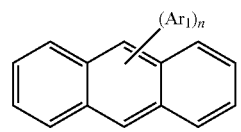

[Formula 3]

wherein, in Formula 3,
each Ar$_1$ is independently a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a substituted or unsubstituted heteroaryl group having 5 to 50 ring carbon atoms, a substituted or unsubstituted silyl group, a carboxyl group, a halogen atom, a cyano group, a nitro group, or a hydroxyl group, and
n is an integer of 1 to 10.

7. The organic EL device as claimed in claim 1, wherein the emission layer-side hole transport material represented by Formula 1 is one of the following Compounds 1 to 12:
1
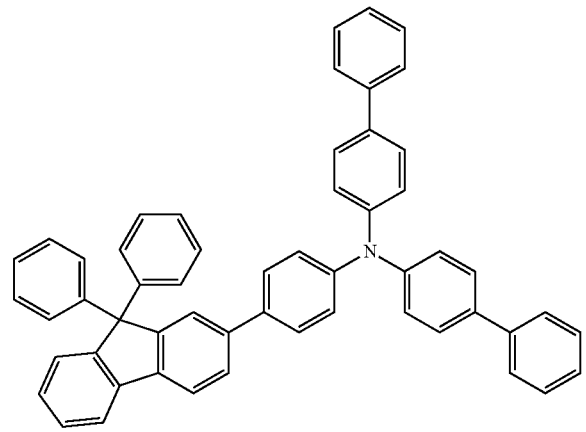
2
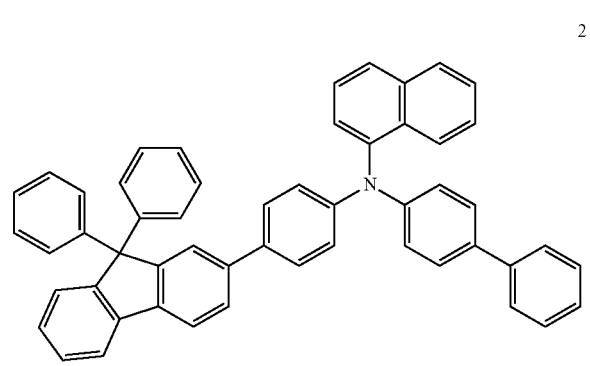
3
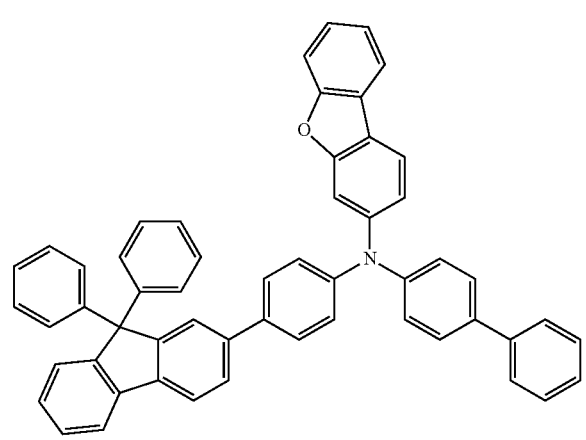
4
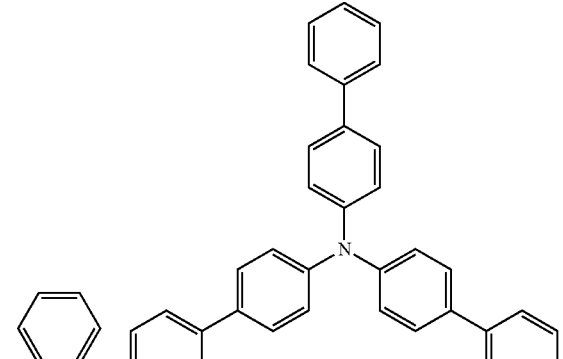
5
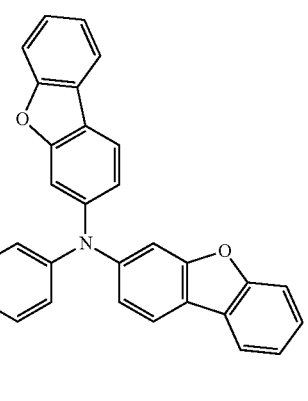
6
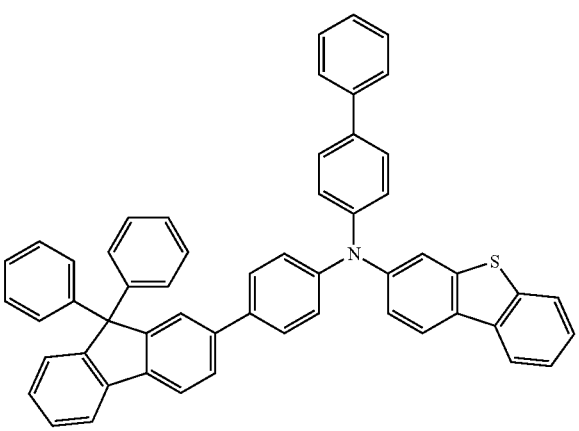

-continued

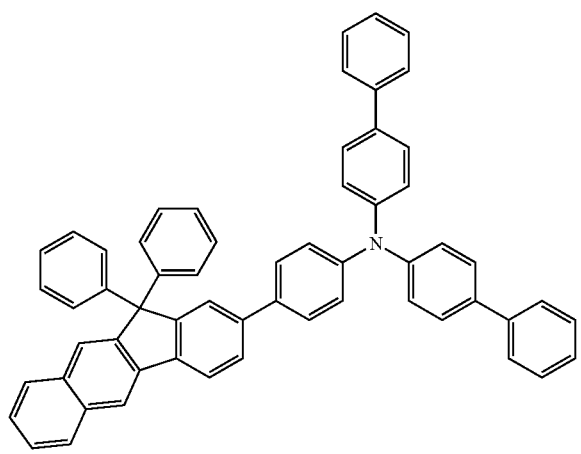

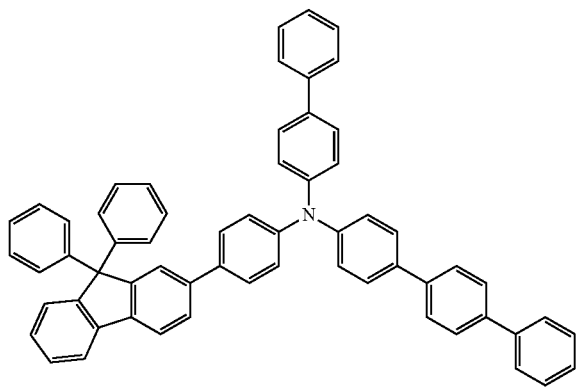

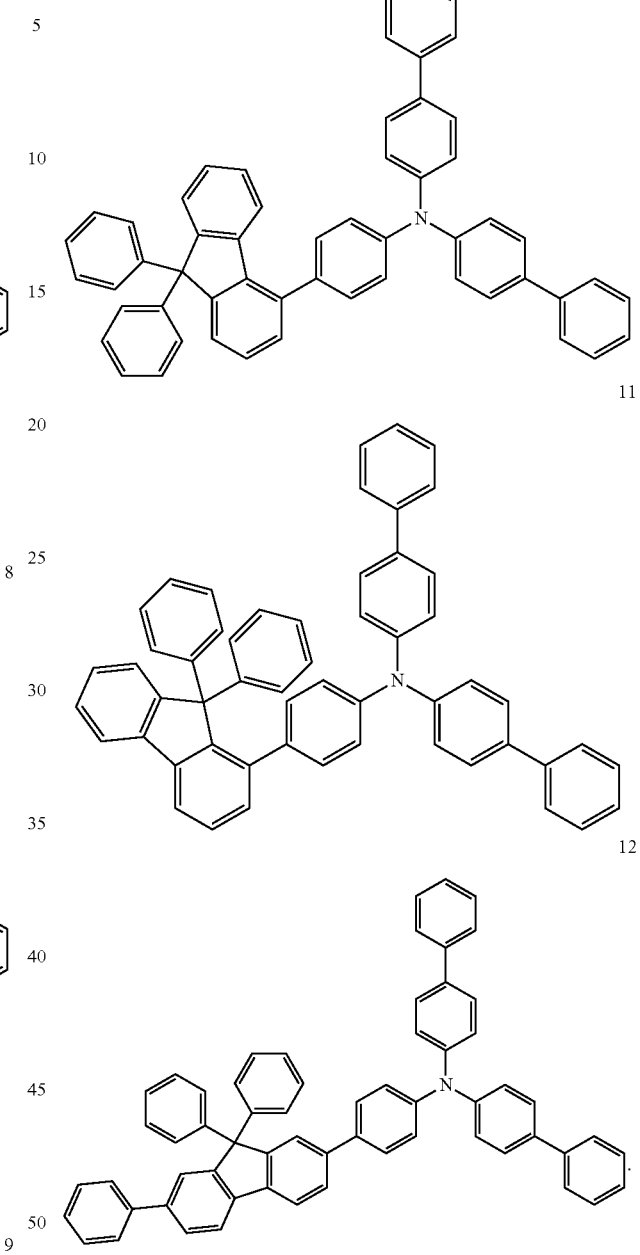

8. An organic electroluminescent (EL) device, comprising:
an anode;
an emission layer;
an anode-side hole transport layer between the anode and the emission layer, the anode-side hole transport layer including an electron accepting material;
an intermediate hole transport layer between the anode-side hole transport layer and the emission layer, the intermediate hole transport layer including an intermediate hole transport material; and
an emission layer-side hole transport layer between the intermediate hole transport layer and the emission layer, the emission layer-side hole transport layer being adjacent to the emission layer, wherein the intermediate hole transport layer and the emission layer-side hole transport layer are in contact with each other, wherein the emission layer-side hole transport layer includes an emission layer-side hole transport material represented by the following Formula 1:

[Formula 1]

wherein, in Formula 1,

Ar$_1$ and Ar$_2$ are each independently a substituted or unsubstituted aryl group having 6 to 50 ring carbon atoms or a substituted or unsubstituted heteroaryl group having 5 to 50 ring carbon atoms, R$_1$ to R$_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of R$_1$ to R$_3$ being separate or bound to form a ring, m is an integer of 0 to 4, p and q are each independently an integer of 0 to 5, L$_1$ is a direct linkage, a substituted or unsubstituted arylene group having 6 to 18 ring carbon atoms, or a substituted or unsubstituted heteroarylene group having 5 to 15 ring carbon atoms, and carbon atoms a and b are separate.

9. The organic EL device as claimed in claim 8, wherein the intermediate hole transport material includes a compound represented by the following Formula 2:

[Formula 2]

wherein, in Formula 2,

Ar$_1$ to Ar$_3$ are each independently a substituted or unsubstituted aryl group having 6 to 50 ring carbon atoms or a substituted or unsubstituted heteroaryl group having 5 to 50 ring carbon atoms, Ar$_4$ is a hydrogen atom, a deuterium atom, a halogen atom, a substituted or unsubstituted aryl group having 6 to 50 ring carbon atoms, a substituted or unsubstituted heteroaryl group having 5 to 50 ring carbon atoms, or a substituted or unsubstituted alkyl group having 1 to 50 carbon atoms, and L$_1$ is a direct linkage, a substituted or unsubstituted arylene group having 6 to 18 ring carbon atoms, or a substituted or unsubstituted heteroarylene group having 5 to 15 ring carbon atoms.

10. The organic EL device as claimed in claim 8, wherein the electron accepting material has a lowest unoccupied molecular orbital (LUMO) level of about −9.0 eV to about −4.0 eV.

11. The organic EL device as claimed in claim 8, wherein the anode-side hole transport layer is adjacent to the anode.

12. The organic EL device as claimed in claim 8, wherein the emission layer includes a compound represented by the following Formula 3:

[Formula 3]

wherein, in Formula 3, each Ar$_1$ is independently a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a substituted or unsubstituted heteroaryl group having 5 to 50 ring carbon atoms, a substituted or unsubstituted silyl group, a carboxyl group, a halogen atom, a cyano group, a nitro group, or a hydroxyl group, and n is an integer of 1 to 10.

13. The organic EL device as claimed in claim 8, wherein the emission layer-side hole transport material represented by Formula 1 is one of the following Compounds 1 to 12:

1

2
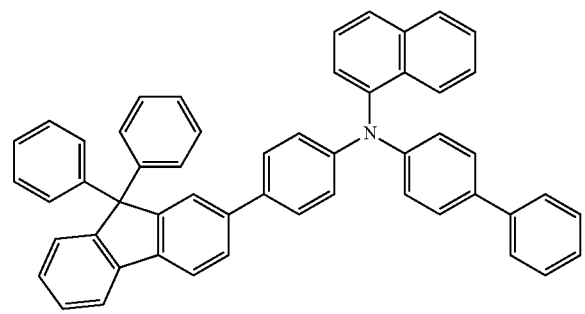
3
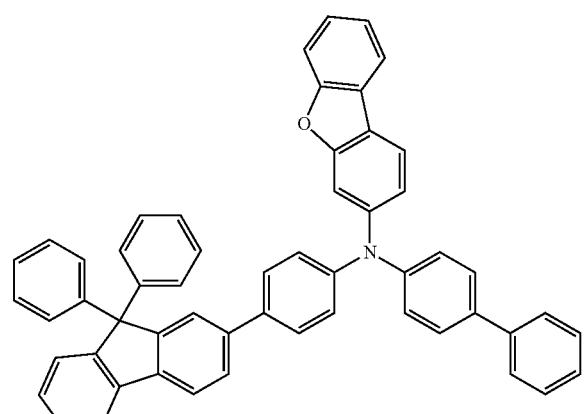
4
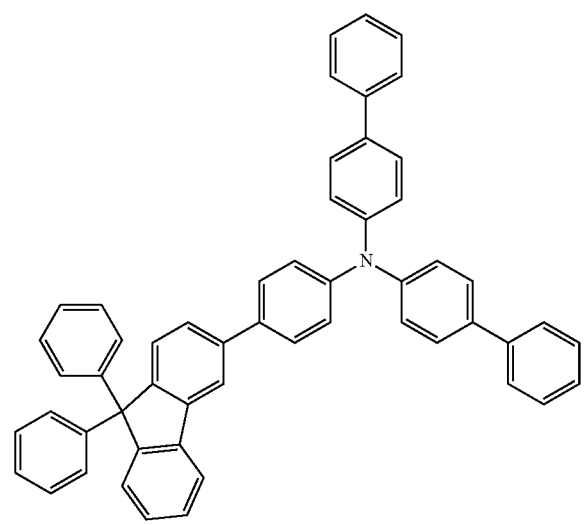
5
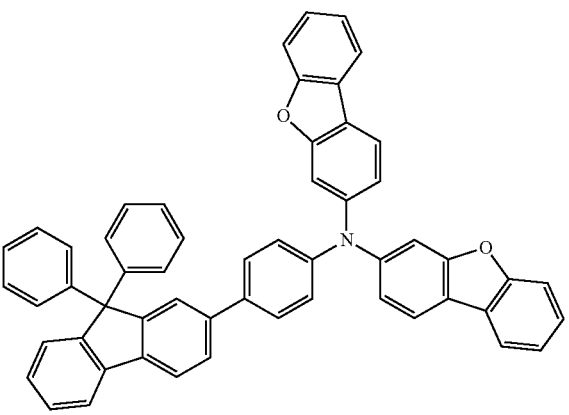
6
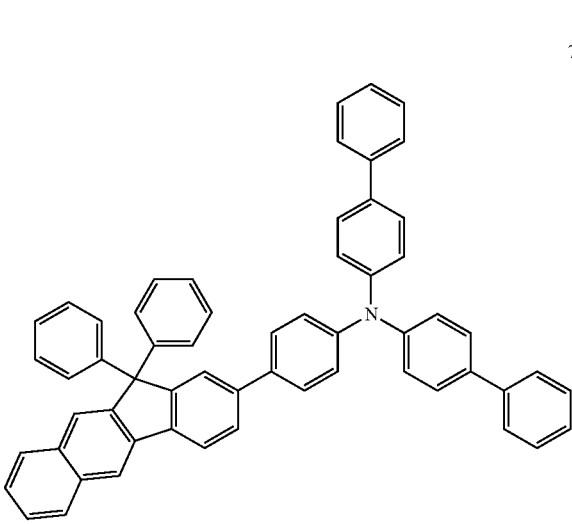
7

8
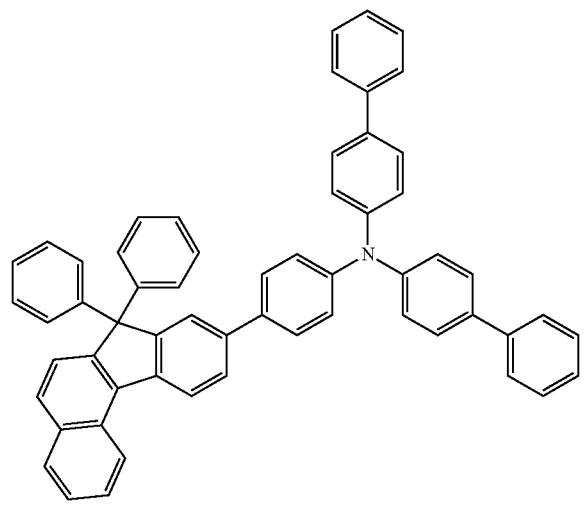
9
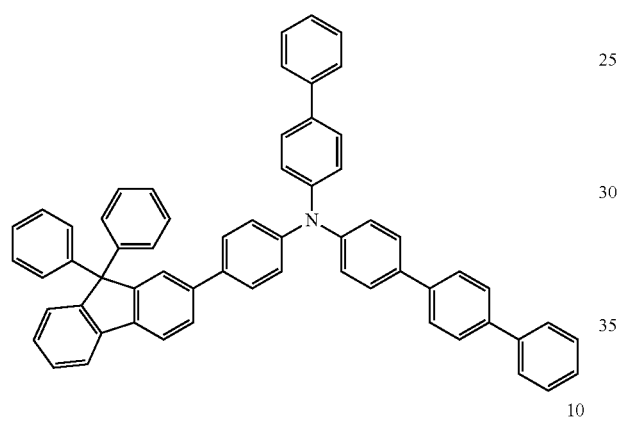
10
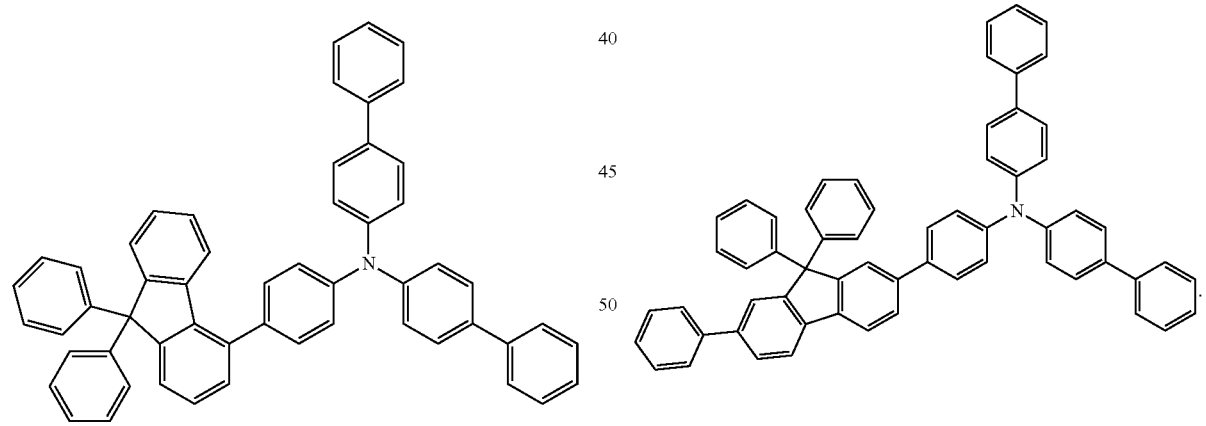
11
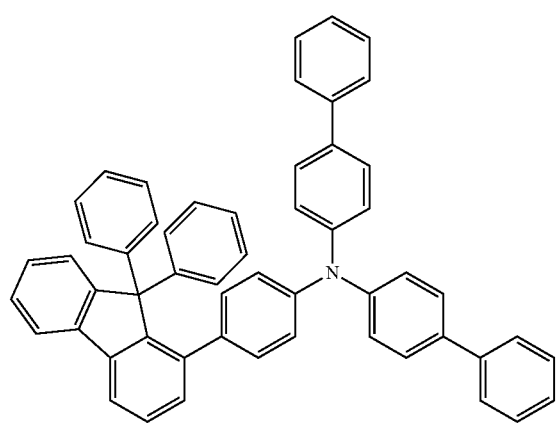
12
* * * * *

(12) EX PARTE REEXAMINATION CERTIFICATE (11520th)
United States Patent
Sasaki et al.

(10) Number: US 9,893,293 C1
(45) Certificate Issued: May 29, 2019

(54) ORGANIC ELECTROLUMINESCENT DEVICE

(71) Applicant: SAMSUNG DISPLAY CO., LTD., Yongin-si, Gyeonggi-do (KR)

(72) Inventors: Ikuo Sasaki, Yokohama (JP); Xiulan Jin, Yokohama (JP); Masatsugu Ueno, Yokohama (JP); Koushin Matsuoka, Yokohama (JP)

(73) Assignee: SAMSUNG DISPLAY CO., LTD., Samsung-ro, Giheung-gu, Yongin-si, Gyeonggi-do (KR)

Reexamination Request:
No. 90/014,200, Sep. 11, 2018

Reexamination Certificate for:
Patent No.: 9,893,293
Issued: Feb. 13, 2018
Appl. No.: 14/937,314
Filed: Nov. 10, 2015

(30) Foreign Application Priority Data

Dec. 2, 2014 (JP) .................. 2014-244485
Dec. 2, 2014 (JP) .................. 2014-244490

(51) Int. Cl.
*C09K 11/00* (2006.01)
*H01L 51/00* (2006.01)
(Continued)

(52) U.S. Cl.
CPC .......... *H01L 51/006* (2013.01); *C07C 211/43* (2013.01); *C07C 211/44* (2013.01); *C07C 211/49* (2013.01); *C07C 211/61* (2013.01); *C07D 401/14* (2013.01); *C07D 403/10* (2013.01); *C09K 11/025* (2013.01); *C09K 11/06* (2013.01); *H01L 51/0058* (2013.01); *H01L 51/0061* (2013.01); *H01L 51/0072* (2013.01); *H01L 51/5064* (2013.01);
(Continued)

(58) Field of Classification Search
None
See application file for complete search history.

(56) References Cited

To view the complete listing of prior art documents cited during the proceeding for Reexamination Control Number 90/014,200, please refer to the USPTO's public Patent Application Information Retrieval (PAIR) system under the Display References tab.

*Primary Examiner* — Ling X Xu

(57) ABSTRACT

An organic EL device including an anode; an emission layer; an anode-side hole transport layer between the anode and the emission layer, the anode-side hole transport layer including an anode-side hole transport material and being doped with an electron accepting material; an intermediate hole transport layer between the anode-side hole transport layer and the emission layer, the intermediate hole transport layer including an intermediate hole transport material; and an emission layer-side hole transport layer between the intermediate hole transport layer and the emission layer, the emission layer-side hole transport layer being adjacent to the emission layer, wherein the emission layer-side hole transport layer includes an emission layer-side hole transport material represented by the following Formula 1:

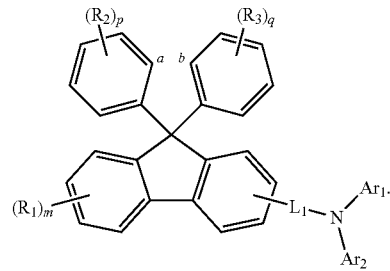

[Formula 1]

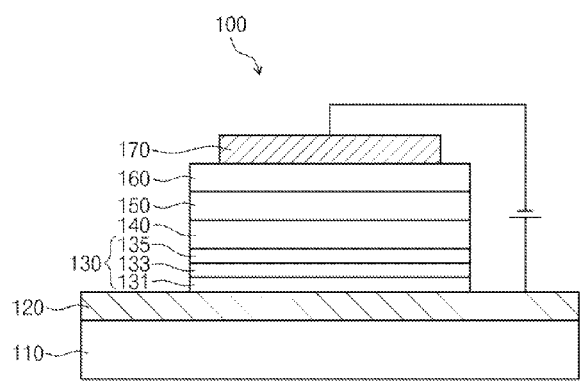

(51) Int. Cl.
*C07C 211/61* (2006.01)
*C09K 11/06* (2006.01)
*C09K 11/02* (2006.01)
*H01L 51/50* (2006.01)
*C07D 403/10* (2006.01)
*C07C 211/43* (2006.01)
*C07C 211/49* (2006.01)
*C07D 401/14* (2006.01)
*C07C 211/44* (2006.01)

(52) U.S. Cl.
CPC .......... *C09K 2211/1014* (2013.01); *C09K 2211/1088* (2013.01); *H01L 51/0054* (2013.01); *H01L 51/0073* (2013.01); *H01L 51/0074* (2013.01); *H01L 51/506* (2013.01); *H01L 51/5012* (2013.01); *H01L 2251/308* (2013.01); *H01L 2251/552* (2013.01)

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 2, 7, 9 and 13 are cancelled.

Claims 1, 3, and 8 are determined to be patentable as amended.

Claims 4-6 and 10-12, dependent on an amended claim, are determined to be patentable.

1. An organic electroluminescent (EL) device, comprising:
   an anode;
   an emission layer;
   an anode-side hole transport layer between the anode and the emission layer, the anode-side hole transport layer including an anode-side hole transport material and being doped with an electron accepting material;
   an intermediate hole transport layer between the anode-side hole transport layer and the emission layer, the intermediate hole transport layer including an intermediate hole transport material; and
   an emission layer-side hole transport layer between the intermediate hole transport layer and the emission layer, the emission layer-side hole transport layer being adjacent to the emission layer,
   wherein the intermediate hole transport layer and the emission layer-side hole transport layer are in contact with each other,
   wherein the emission layer-side hole transport layer includes an emission layer-side hole transport material
   [represented by the following Formula 1:

[Formula 1]

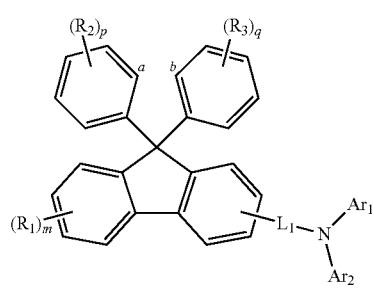

wherein, in Formula 1,
$Ar_1$ and $Ar_2$ are each independently a substituted or unsubstituted aryl group having 6 to 50 ring carbon atoms or a substituted or unsubstituted heteroaryl group having 5 to 50 ring carbon atoms,
$R_1$ to $R_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of $R_1$ to $R_3$ being separate or bound to form a ring,
m is an integer of 0 to 4,
p and q are each independently an integer of 0 to 5,
$L_1$ is a direct linkage, a substituted or unsubstituted arylene group having 6 to 18 ring carbon atoms, or a substituted or unsubstituted heteroarylene group having 5 to 15 ring carbon atoms, and
carbon atoms a and b are separate], *the emission layer-side hole transport material being one of the following Compounds 1 to 3, 5 to 9, and 12:*

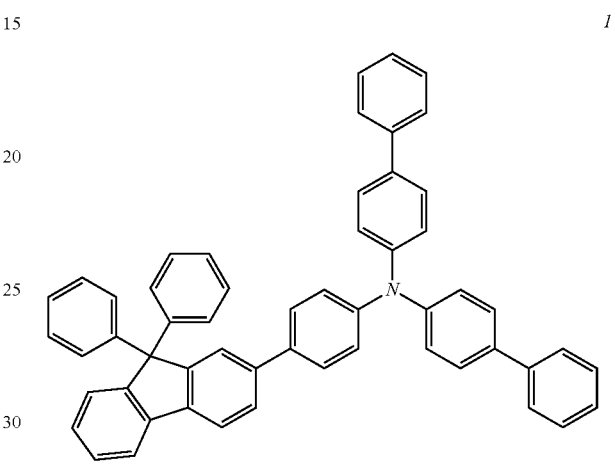

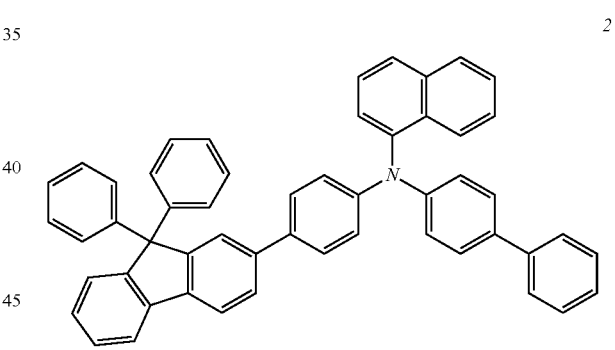

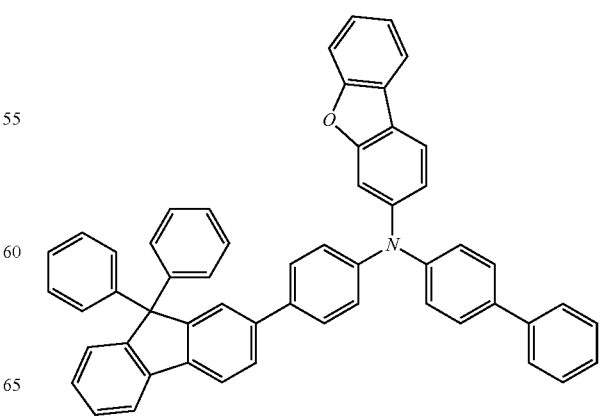

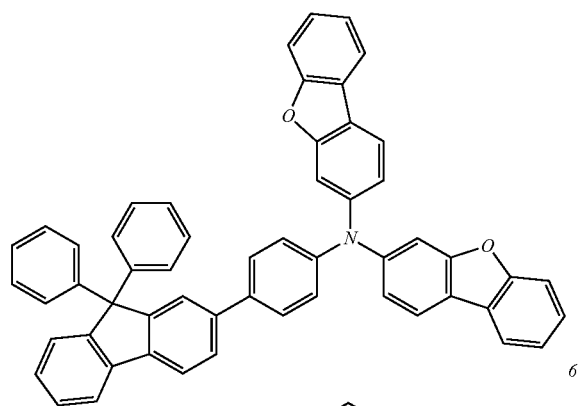
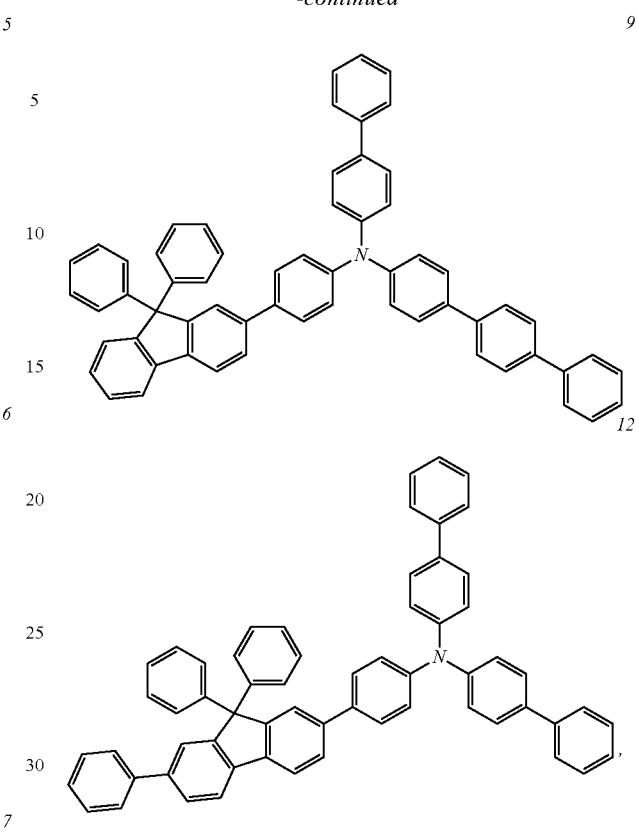
and
wherein the intermediate hole transport material is one of the following Compounds 2-2, 2-4 to 2-10, 2-12 to 2-14, and 2-16:
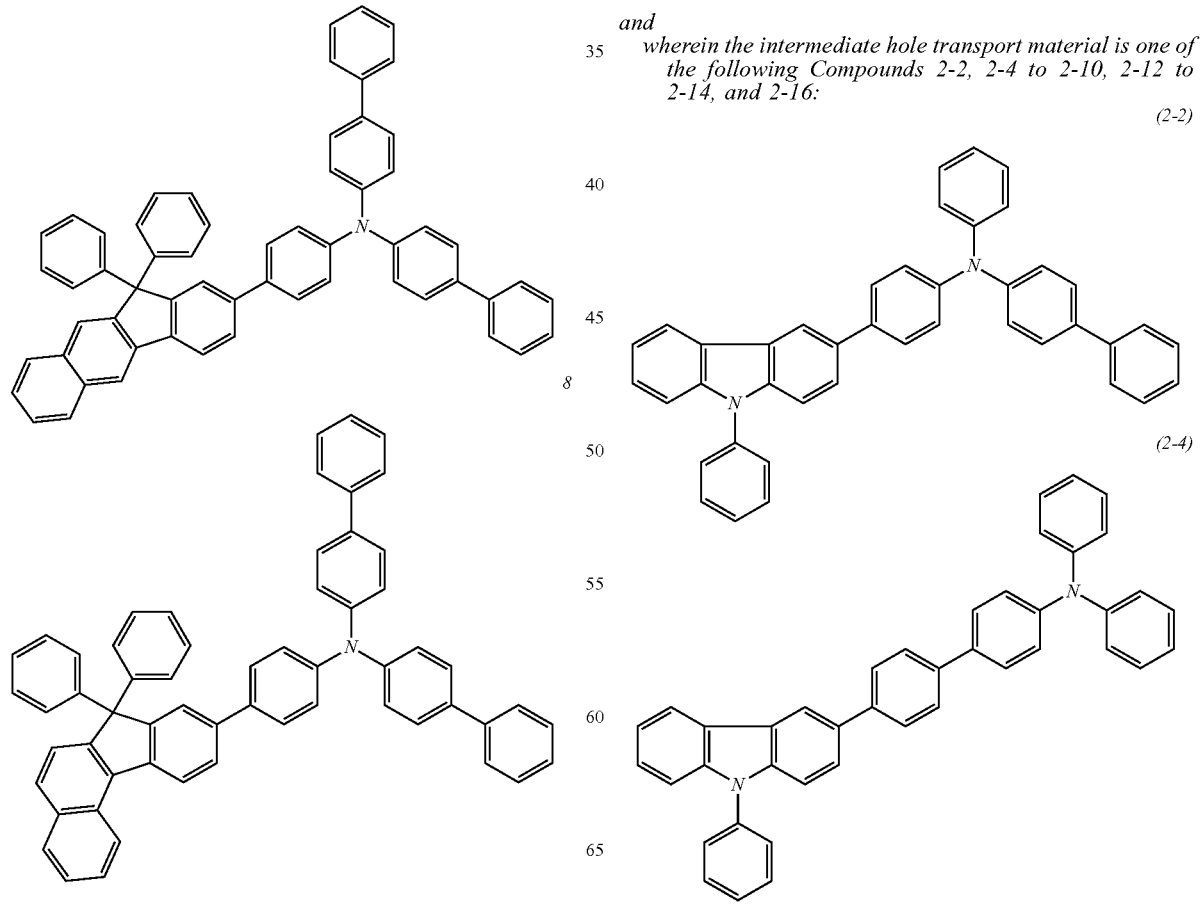

(2-5)
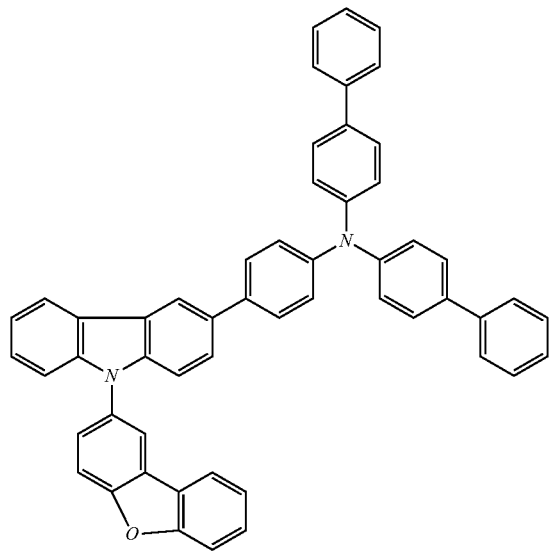
(2-6)
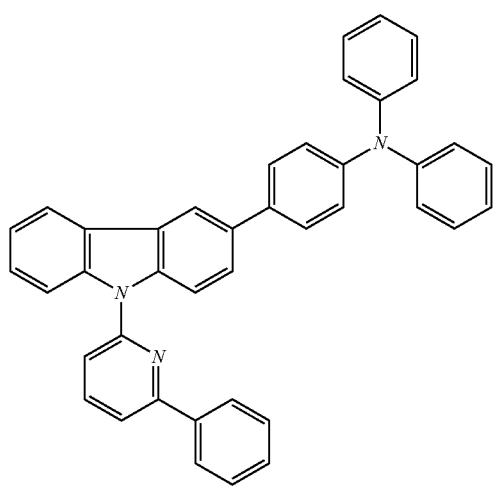
(2-7)
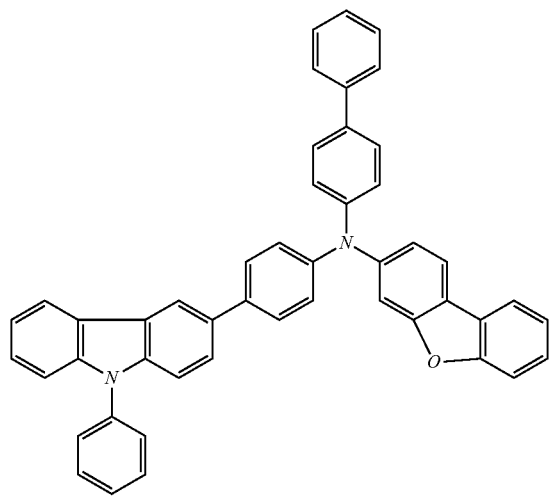
(2-8)
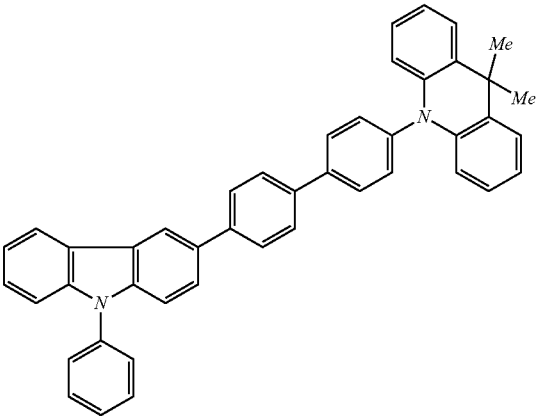
(2-9)
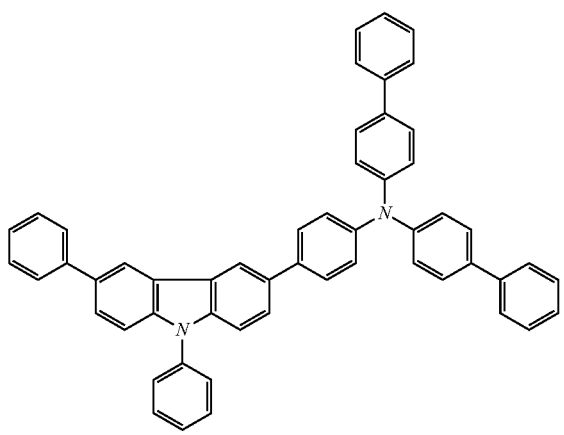
(2-10)
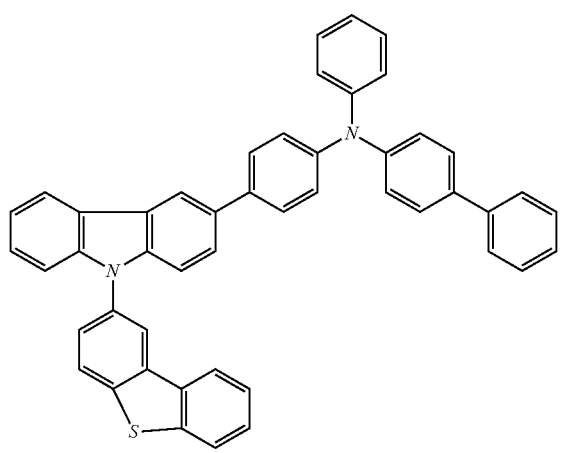

(2-12)

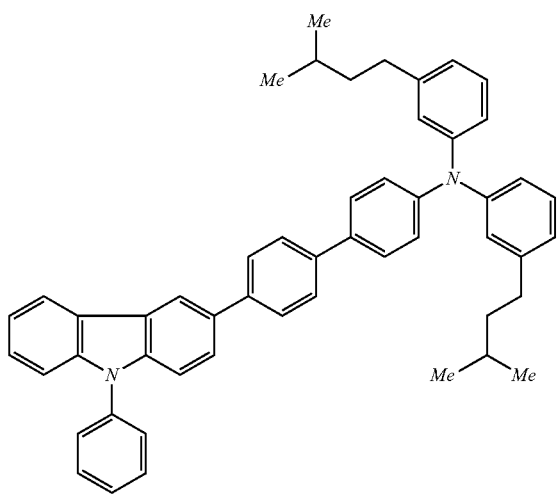

(2-13)

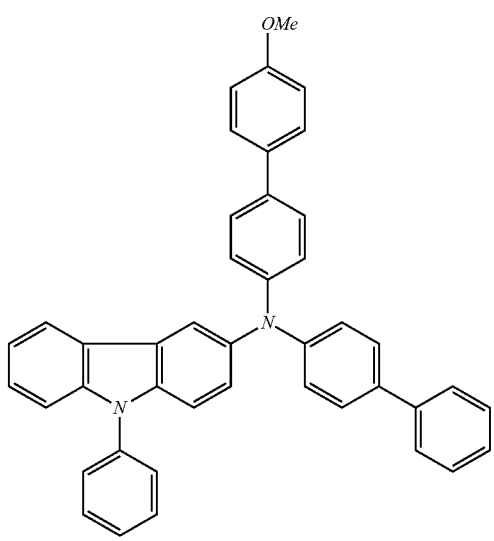

(2-14)

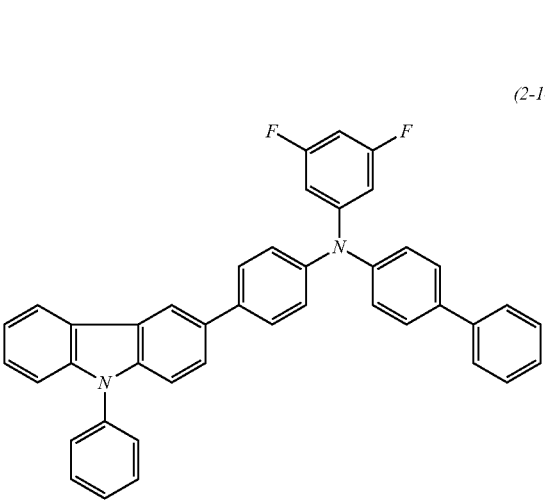

(2-16)

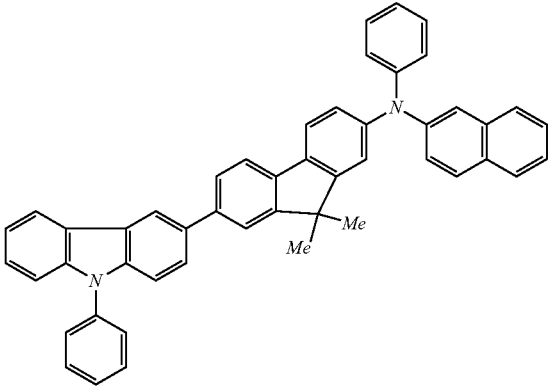

3. The organic EL device as claimed in claim [2] *1*, wherein the anode-side hole transport material includes [the compound represented by Formula 2] *one of Compounds 2-2, 2-4 to 2-10, 2-12 to 2-14, and 2-16*.

8. An organic electroluminescent (EL) device, comprising:
an anode;
an emission layer;
an anode-side hole transport layer between the anode and the emission layer, the anode-side hole transport layer including an electron accepting material;
an intermediate hole transport layer between the anode-side hole transport layer and the emission layer, the intermediate hole transport layer including an intermediate hole transport material; and
an emission layer-side hole transport layer between the intermediate hole transport layer and the emission layer, the emission layer-side hole transport layer being adjacent to the emission layer,
wherein the intermediate hole transport layer and the emission layer-side hole transport layer are in contact with each other,
wherein the emission layer-side hole transport layer includes an emission layer-side hole transport material [represented by the following Formula 1:

[Formula 1]

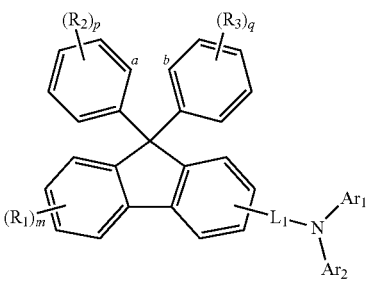

wherein, in Formula 1,
$Ar_1$ and $Ar_2$ are each independently a substituted or unsubstituted aryl group having 6 to 50 ring carbon atoms or a substituted or unsubstituted heteroaryl group having 5 to 50 ring carbon atoms,
$R_1$ to $R_3$ are each independently a substituted or unsubstituted alkyl group having 1 to 20 carbon atoms, a substituted or unsubstituted aryl group having 6 to 50 ring carbon atoms, a substituted or unsubstituted heterocyclic group having 3 to 50 ring carbon atoms, adjacent ones of $R_1$ to $R_3$ being separate or bound to form a ring, m is an integer of 0 to 4, p and q are each independently an integer of 0 to 5, $L_1$ is a direct linkage, a substituted or unsubstituted arylene group having 6 to 18 ring carbon atoms, or a substituted or unsubstituted heteroarylene group having 5 to 15 ring carbon atoms, and carbon atoms a and b are separate], *the emission layer-side hole transport material being one of the following Compounds 1 to 3, 5 to 9, and 12:*

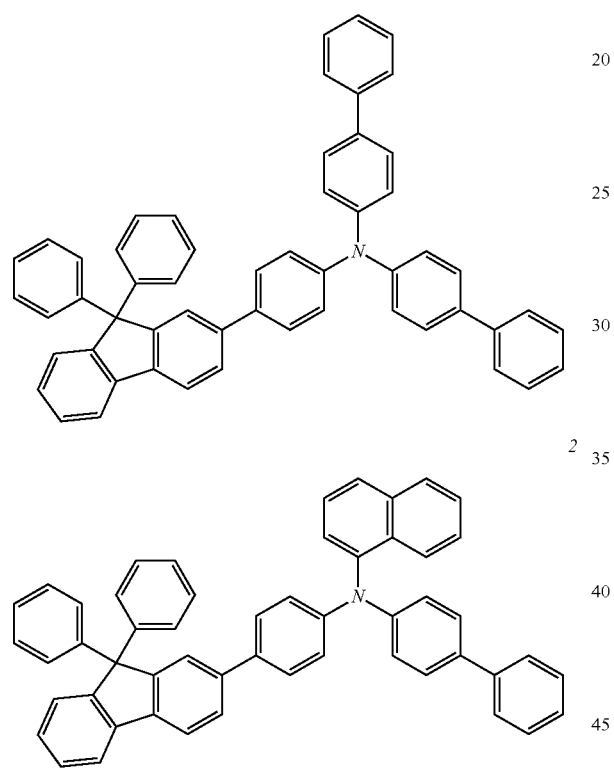

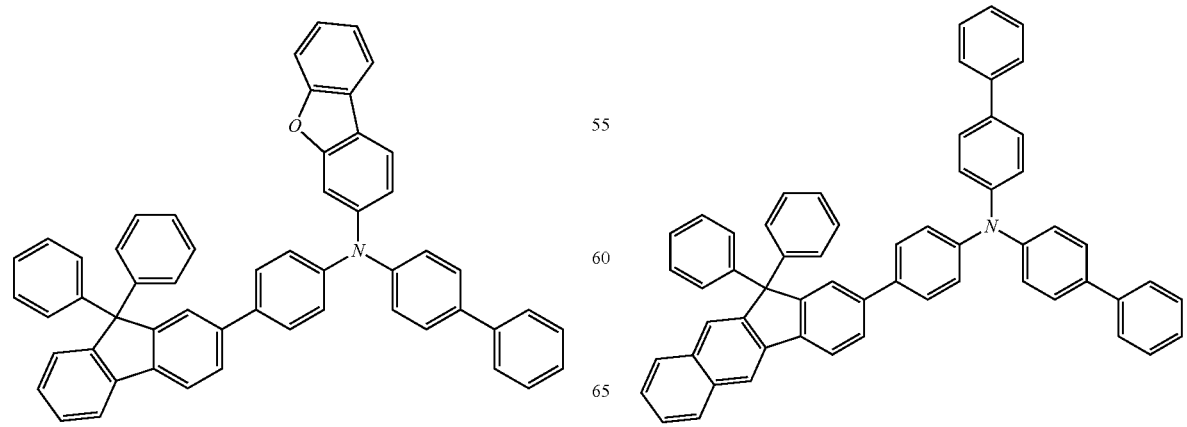

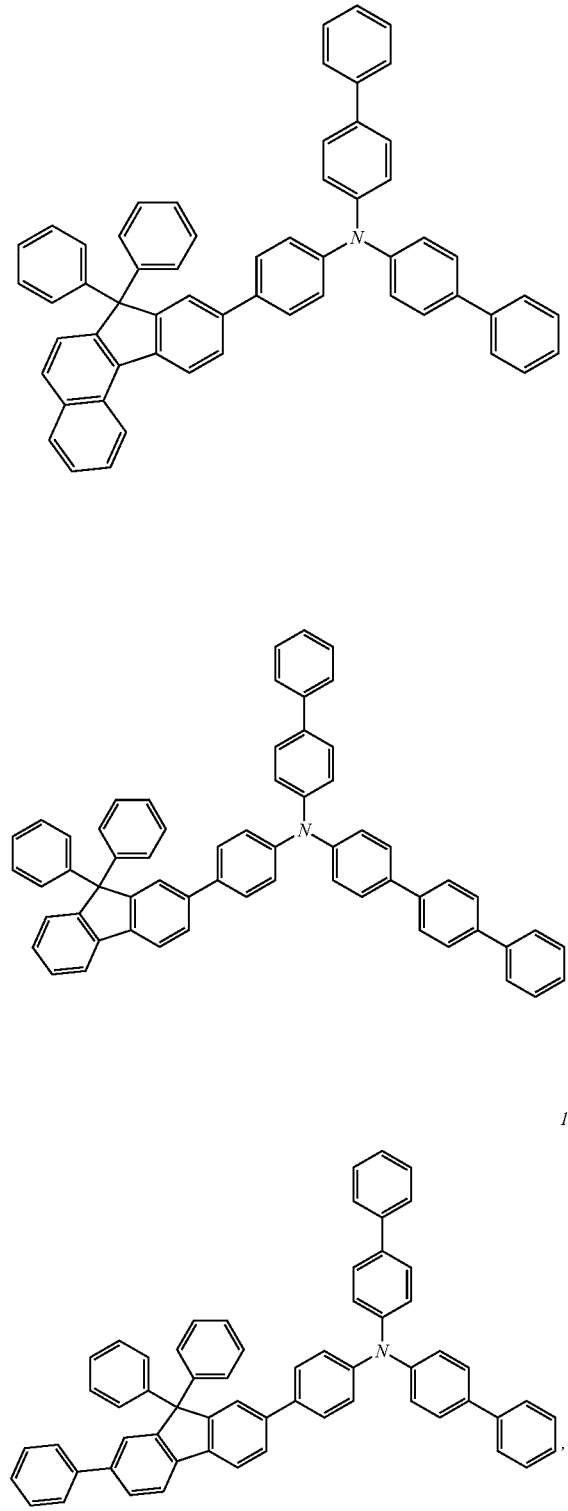
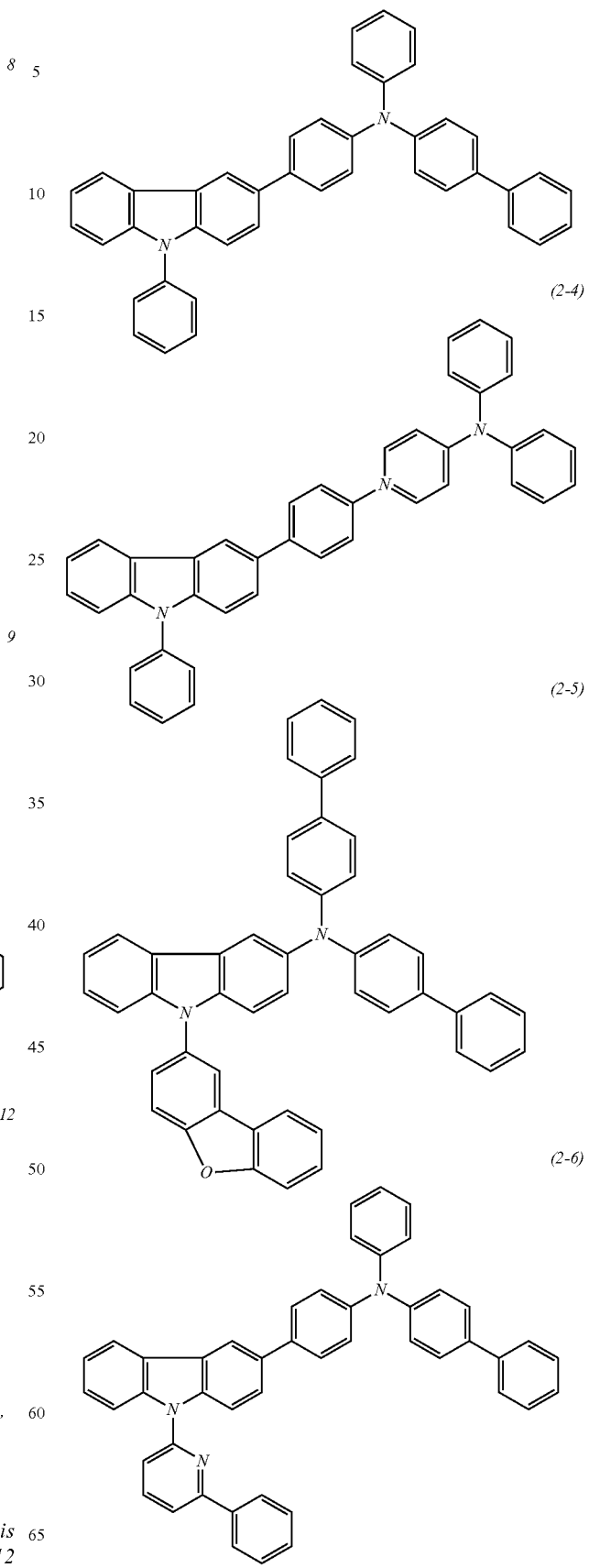
and wherein the intermediate hole transport material is one of the following Compounds 2-2, 2-4 to 2-10, 2-12 to 2-14, and 2-16:

(2-7)
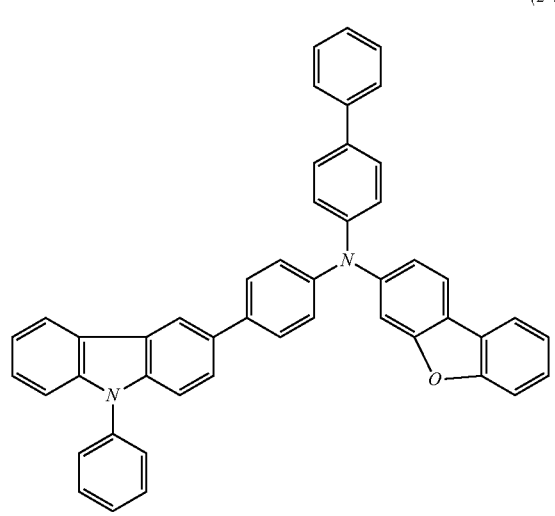
(2-10)
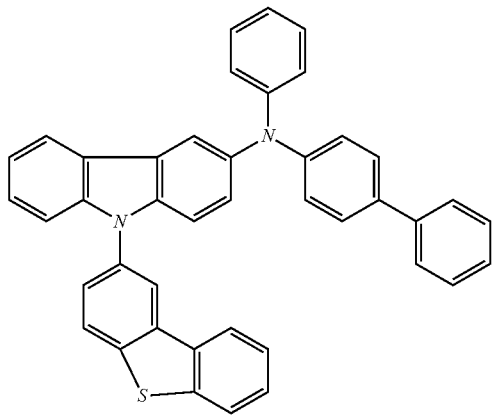
(2-8)
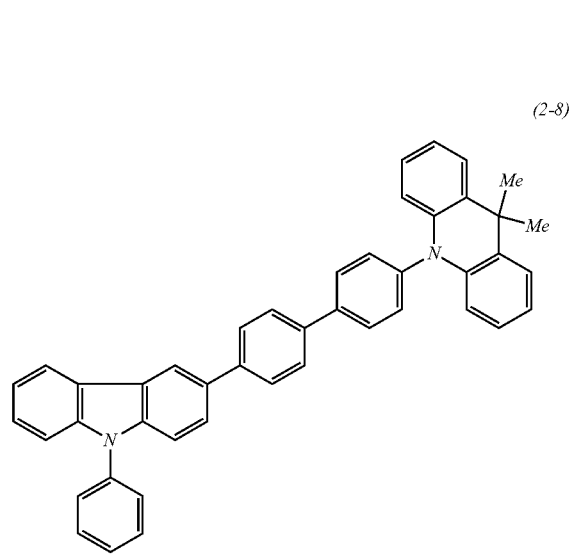
(2-12)
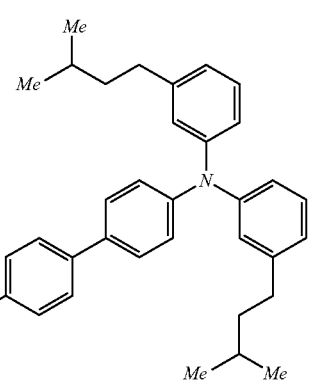
(2-9)
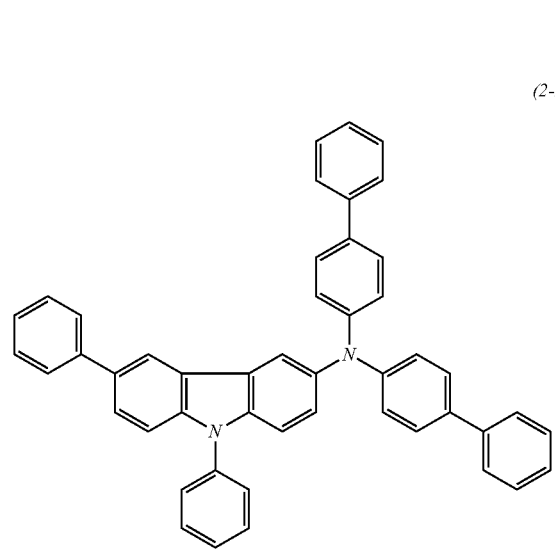
(2-13)
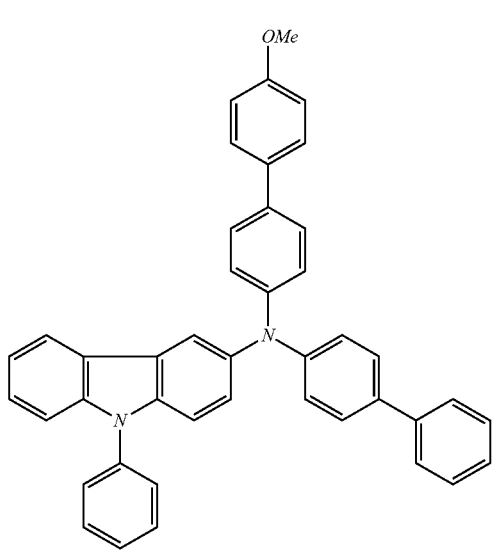

-continued
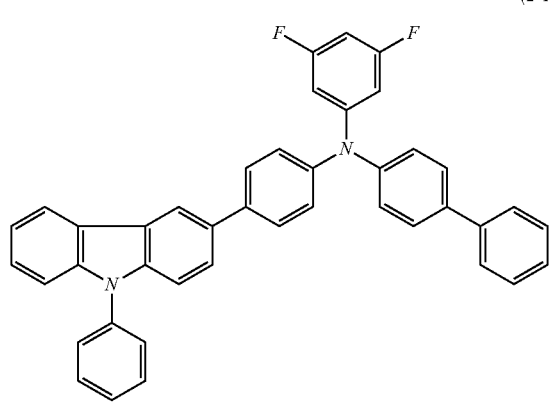
(2-14)
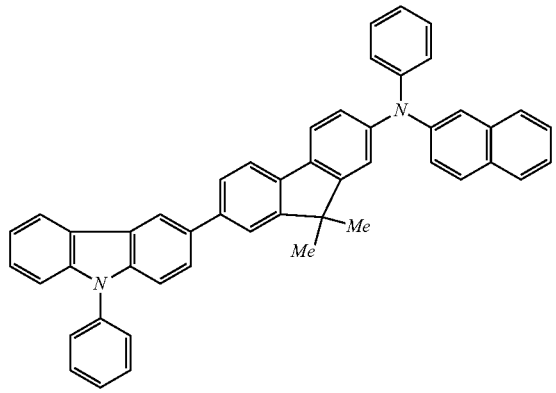
(2-16)
* * * * *